United States Patent [19]

Henderson

[11] Patent Number: 5,604,091

[45] Date of Patent: Feb. 18, 1997

[54] METHODS FOR PROTEIN BINDING ENZYME COMPLEMENTATION

[75] Inventor: Daniel R. Henderson, Benicia, Calif.

[73] Assignee: Microgenics Corporation, Concord, Calif.

[21] Appl. No.: 268,711

[22] Filed: Jun. 30, 1994

Related U.S. Application Data

[63] Continuation of Ser. No. 841,125, Feb. 25, 1992, abandoned, which is a continuation of Ser. No. 788,370, Oct. 22, 1985, Pat. No. 5,120,653, which is a continuation-in-part of Ser. No. 721,267, Apr. 8, 1985, Pat. No. 4,708,929, which is a continuation-in-part of Ser. No. 666,080, Oct. 29, 1984, abandoned, which is a continuation-in-part of Ser. No. 585,356, Mar. 1, 1984, abandoned.

[51] Int. Cl.$^6$ .................... G01N 33/535; G01N 33/542; G01N 33/569

[52] U.S. Cl. .................. 435/5; 435/7.6; 435/7.8; 435/7.9; 435/18; 435/172.3; 435/207; 436/501; 436/512; 436/537; 436/544; 530/309; 530/324; 530/807; 930/240; 935/47

[58] Field of Search .................. 435/5, 7.6, 7.9, 435/18, 172.3, 975, 207, 7.8; 436/537, 544, 512, 501; 530/309, 324, 807; 930/240; 935/47

[56] References Cited

U.S. PATENT DOCUMENTS

| | | | |
|---|---|---|---|
| 4,378,428 | 3/1983 | Farina et al. | 435/7 |
| 4,708,929 | 11/1987 | Henderson | 435/7 |
| 4,745,055 | 5/1988 | Schenk et al. | 435/7 |

FOREIGN PATENT DOCUMENTS

| | | |
|---|---|---|
| 0062277 | 10/1982 | European Pat. Off. . |
| 0300487 | 1/1989 | European Pat. Off. . |
| 0327312 | 8/1989 | European Pat. Off. . |
| 86/02666 | 5/1986 | WIPO . |
| 90/05749 | 5/1990 | WIPO . |
| 90/13569 | 11/1990 | WIPO . |

OTHER PUBLICATIONS

Daniel R. Henderson et al., Clin. Chem. 32/9 1637–1641 (1986).
Rose et al. *Methods in Enzymology* 101: 167–182 (1983).
Ngo et al. in *Immunoenzyme techniques* p. 281 (1985).
Senmetto (ed) 4th (ed), *Manual of Clinical Microbiology*, pp. 823–832, (1985).

*Primary Examiner*—David Saunders
*Attorney, Agent, or Firm*—Luann Cserr

[57] ABSTRACT

This invention relates to improved methods and novel compositions for enzyme complementation assays for qualitative and quantitative determination of a suspected analyte in a sample. The use of enzyme-acceptor and enzyme-donor polypeptides prepared by recombinant DNA techniques, DNA synthesis or chemical polypeptide synthesis techniques which are capable of interacting to form an active enzyme complex having catalytic activity characteristic of β-galactosidase is described. Both homogeneous and heterogeneous assays utilizing these polypeptides are described.

12 Claims, 30 Drawing Sheets

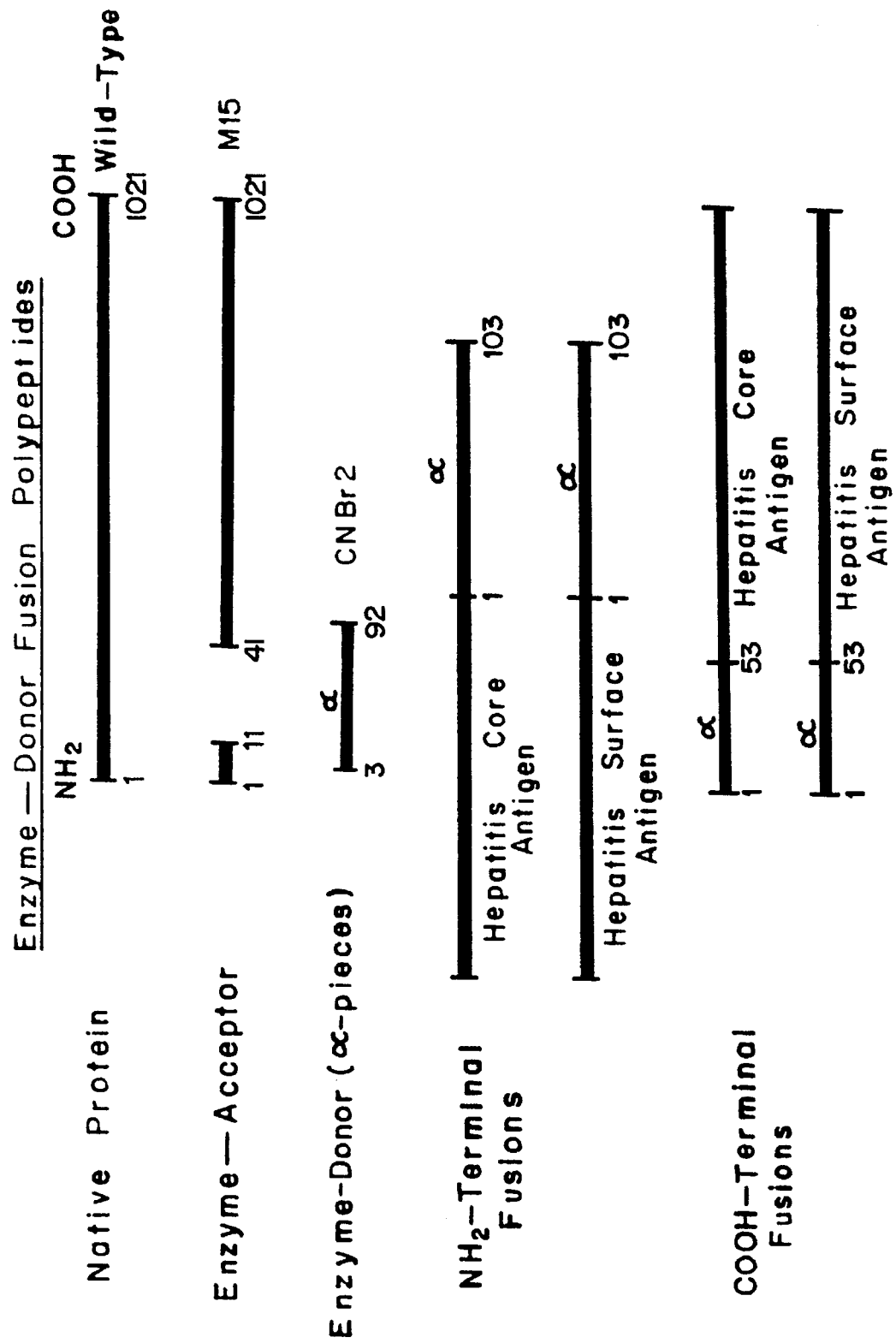

DNA AND AMINO ACID SEQUENCES OF ALPHA-PIECE CLONES:

THE N-TERMINUS OF ALL CLONES IS:
(EXCEPT p148)

```
Met Asp Pro Arg Ala Ser Ser Asn Ser Leu Ala Val Val Leu Gln Arg Arg Asp Trp Glu Asn Pro
ATG GAT CCC CGG GCG AGC TCG AAT TCA CTG GCC GTC GTT TTA CAA CGT CGT GAC TGG GAA GGC CCT

Gly Val Thr Glu Leu Asn Arg Leu Ala Ala His Pro Pro Phe Ala Ser Trp Arg Asn Ser Glu Glu Ala Arg Thr       (47 amino acids)
GGC GTT ACC CAA CTT AAT CGC CTT GCA GCA CAT CCC CCT TTC GCC AGC TGG CGT AAT AGC GAA GAG GCC CGC ACC
```

THE FOLLOWING SEQUENCES OF EACH CLONE ARE:

M9:
```
Asp Arg Pro Ser Gln Leu Leu Cys*Gly Val Lys*Tyr Arg Thr Asp Ala -  (17 amino acids)
GAT CGC CCT TCC CAA CAG TTG CTA TGC GGT GTG AAA TAC CGC ACA GAT GCG TAA
```

B9:
```
Asp Arg Pro Ser Gln Leu Leu Cys*Gly Ser Leu Cys*Gly Val Lys*Tyr Thr Asp Ala -   (19 amino acids)
GAT CGC CCT TCC CAA CAG TTG CGC AGC CTA TGC GGT GTG AAA TAC AGT CGC ACA GAT GCG TAA
```

M6:
```
Asp Arg Pro Ser Gln Leu Leu Arg Ser Leu Asn Gly Leu Glu Leu Cys*Gly Val Lys*Tyr Arg Thr Asp Ala -  (23 amino acids)
GAT CGC CCT TCC CAA CAG TTG CGC AGC CTG AAT GGC CTG GAA TTA TGC GGT GTG AAA TAC CGC ACA GAT GCG TAA
```

P6:
```
Met Arg Cys*Glu Val Val Arg His Pro Ile Arg Arg Arg Cys*Val Arg Lys*Tyr Arg Ile Arg Ser Ala Ser Leu Thr Asp Ser Leu
ATG CGG TGT GAA GTA GTT CGG ATA CCG CAC AGA TGC GTA AGA AAA TAC AGG ATC AGG CGC TCG TCC TCC GTC CTC ACT GAC TCG CTG

Arg Ser Val Val Arg Leu Arg Arg Ala Val Ser Ala His Ser Lys*Ala Val Ile Arg Leu Ser Thr Glu Ser Gly Asp Asn Ala
CGC TCG GTC GTT CGG CTG CGG CGA GCG GTA GCG TCA GCT CAC TCA AAG GCG GTA ATA CGG TTA TCC ACA GAA TCA GGG GAT AAC GCA

Gly Lys*Asn Met  -  (60 amino acids)
GGA AAG ATG TGA
```

FIG. 4A p125:

Asp Arg Pro Ser Gln Gln Leu Arg Ser Leu Cys*Leu Ala Arg Phe Gly Asp Asp Gly Glu Asn Leu — (22 amino acids)
GAT CGC CCT TCC CAA CAG TTG CGC AGC CTC TGC CTC GCG CGT TTC GGT GAT GAC GGT GAA ACC CTC TGA p148:

Met Asp Pro Leu Glu Pro Thr Cys*Ser Pro Ser Leu Ala Val Val Leu Gln Arg Arg Glu Asp Trp Glu Asn Pro Gly Val
ATG GAT CCT CTA GAG CCT ACC TCG AGC CCA AGC TTG GCA GTC GTC CTT TTA CAA CGT CGT GAA GAC TGG GAA ACC CCT GGC GTT

Thr Gln Leu Asn Arg Leu Ala Ala His Pro Pro Phe Ala Ser Trp Arg Asn Ser Glu Glu Ala Arg Thr Asp Arg Pro Ser Gln
ACC CAA CTT AAT CGC CTT GCA GCA CAT CCC CCT TTC GCC AGC TGG CGT AAT AGC GAA GAG GCC CGC ACC GAT CGC CCT TCC CAA

Gln Leu Arg Ser Leu Asn Gly Glu Trp Arg Leu Met Arg Tyr Phe Leu Leu Ser His Leu Cys*Gly Ile Ser Arg His Trp
CAG TTG CGC AGC CTG AAT GGC GAA CGG CTG ATG CGG TAT TTT CTC CTT AGC CTA TGC GGT ATT TCA CAC CGC ATA TGG

Cys*Thr Ser Leu Ile Cys*Ser Asp Ala Asp — (95 amino acids)
TGC ACT AGT ACA ATC TGC TCT GAT GCC GAC TAG

| CLONES | TOTAL AMINO ACIDS | POSITION OF CYS* | POSITION OF LYS* |
|---|---|---|---|
| M9 | 64 | 56 | 58 |
| B9 | 66 | (56) | (54) |
| M6 | 58 | 58 | 60 |
| P6 | 70 | 62 | 64 |
| p125 | 107 (60) | 50,56 | 60,90,105 |
| p148 | 69 | 58 | — |
|  | 95 (95 amino acids) | 8,77,85,91 | — |

FIG. 4B

Enzyme-Acceptor Mutants (α-Region) of β-galactosidase

```
Met Asp Pro Arg Ala Ser Ser Asn Ser Leu Ala
ATG GAT CCC CGG GCG AGC TCG AAT TCA CTG GGC
             10                          20
Val Val Leu Gln Arg Arg Asp Trp Glu Asn Pro Gly Val Thr Glu Leu Asn Arg Leu Ala Ala His Pro Pro Phe Ala
GTC GTT TTA CAA CGT CGT GAC TGG GAA AAC CCT GGC GTT ACC CAA CTT AAT CGC CTT GCA GCA CAT CCC CCT TTC GCC
                                                                                30
Pvu II Site
Ser Trp Arg Asn Ser Glu Glu Ala Arg Thr Asp Arg Pro Ser Gln Gln Leu Arg Ser Leu Asn Gly Leu Arg Phe
AGC TGG CGT AAT AGC GAA GAG GCC CGC ACC GAT CGC CCT TCC CAA CAG TTG CGC AGC CTG AAT GGC GAA TTG GGC TTT
                40                                          50                                      60
```

FIG. 5A

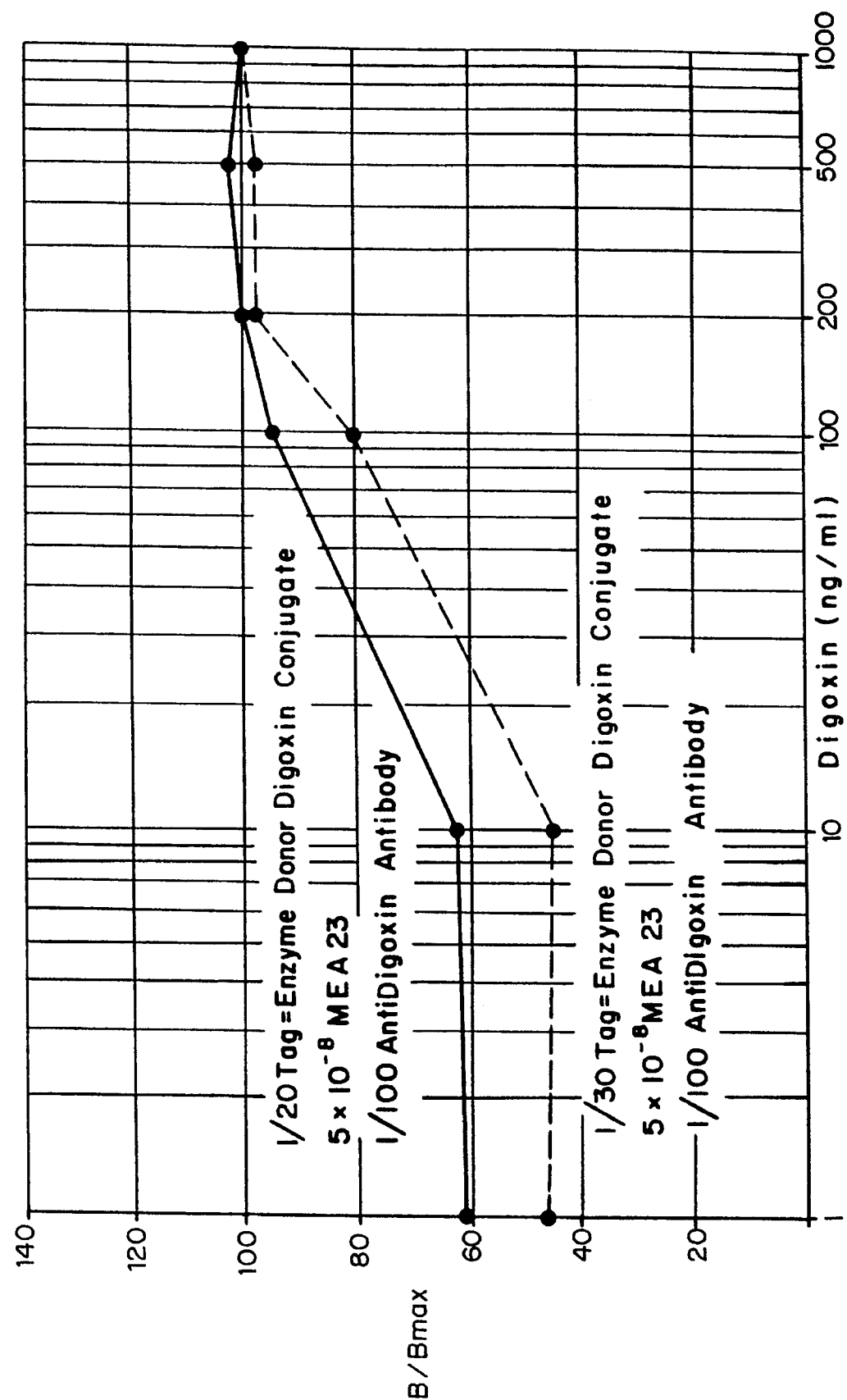

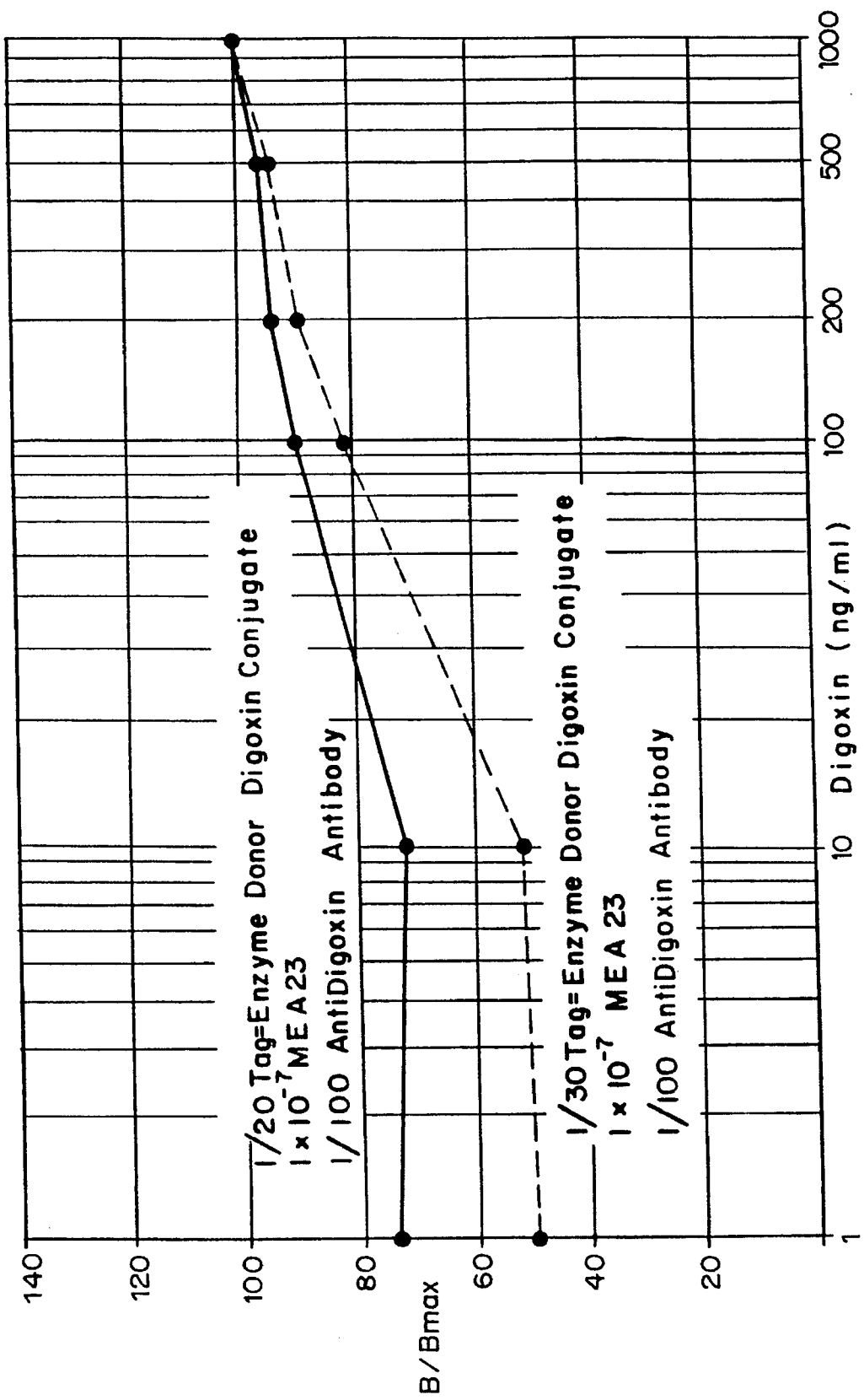

```
ED 1                 Met Asp Pro Ser Gly Asn Pro Tyr Gly Ile Asp Pro Thr Gln Ser Ser Pro Gly Asn Ile Asp Pro Arg Ala Ser Ser
N-terminal                BamHI                                   Cla I                                                    Sma I           Sst I            Encore
fragment             GAT CCC AGC GGC AAC CCA TAT GGT ATC GAT CCG ACT CAG AGC TCT CCT GGC AAC ATC GAT CCG CGG GCG AGC TCG A
                      GG TCG CCG TTG GGT ATA CCA TAG CTA GGC TGA GTC TCG AGA GGA CCG TTG TAG CTA GGC CGC CGC TCG AGC TTA A Gly Leu Glu Ser Arg Ser Ala Gly Met Pro Leu Glu - - -
                               Bgl II Ed 1 (&ED 3)              Bgl I  Xho I   Xba I       Pst I  Sph I                  Xho I              Sal I
C-terminal                  GGC CTC GAG TCT AGA TCT GCA GGC ATG CCC CTC GAG TAA TAG TGA G
fragment             C TTA CCG GAG CTC AGA TCT AGA CGT CCG TAC GGG GAG CTC ATT ATC ACT CAG CT Met Asp Pro Ser Gly Asp Pro Arg Ala Cys Ser
ED 3                      Bam HI                Sph I        Sma I                     Eco RI
N-terminal           GAT CCC AGC GGC GAT CCG CGG GCA TGC TCG
fragment              GG TCG CCG CTA GGC GCC CGT ACG AGC TTA A
```

FIG. 12

ED3
Ser Leu Ala Val Val Leu Gln Arg Arg Asp Trp Glu Asn Pro Gly Val Thr Gln Leu Asn Arg Leu Ala Ala His Pro Pro
Phe Ala Ser Trp Arg Asn Ser Glu Ala Arg Thr Asp Arg Pro Ser Gln Leu Arg Ser Leu Asn Gly Leu Glu Ser
Arg Ser Ala Gly Met Pro Leu Glu
                                 Asp Pro Ser Gly Asp Pro Arg Ala Cys Ser Asn
                                                          *

ED3A
Ser Leu Ala Val Val Leu Gln Arg Arg Asp Trp Glu Asn Pro Gly Val Thr Gln Leu Asn Arg Leu Ala Ala His Pro Pro
Phe Ala Ser Trp Arg Asn Ser Glu Glu Ala Arg Thr
                                                Cys Ile Thr Asp
                                                *

FIG. 14

AMINO ACID SEQUENCES

```
                                                           -5
                                      Met Asp Pro Ser Gly Asp Pro
 *              5                    10                  15                  20                   25
Arg Ala Cys Ser Asn Ser Leu Ala Val Val Leu Gln Arg Arg Asp Trp Glu Asn Pro Gly Val Thr Glu Leu Asn
                30                   35                  40                  45                   50
Arg Leu Ala Ala His Pro Pro Phe Ala Ser Trp Arg Asn Ser Glu Glu Ala Arg Thr Asp Arg Pro Ser Gln Gln
                55                   60                  65
Leu Arg Ser Leu Asn Gly Leu Glu Ser Arg Ser Ala Gly Met Pro Leu Glu  -
```

```
                                                          -5
                                      Met Asp Pro Ser Gly Asn Ile Asp Pro
   -20                 -15                 -10                   0
Met Asp Pro Ser Gly Asn Pro Tyr Gly Ile Asp Pro Thr Glu Ser Ser Pro Gly Asn Ile Asp Pro
                5                    10                  15                  20                   25
Arg Ala Ser Ser Asn Ser Leu Ala Val Val Leu Gln Arg Arg Asp Trp Glu Asn Pro Gly Val Thr Glu Leu Asn
                30                   35                  40                  45                   50
Arg Leu Ala Ala His Pro Pro Phe Ala Ser Trp Arg Asn Ser Glu Glu Ala Arg Thr Asp Cys Pro Ser Gln Gln
                55                   60                  65
Leu Arg Ser Leu Asn Gly Leu Glu Ser Arg Ser Ala Gly Met Pro Leu Glu  -
```

AMINO ACID SEQUENCES

```
                                                      -5                              0
                                        Met Asp Pro Ser Gly Asp Pro
            5              10              15              20              25
Arg Ala Ser Ser Asn Ser Leu Ala Val Val Leu Gln Arg Arg Asp Trp Glu Asn Pro Gly Val Thr Glu Leu Asn
            30              35    *         40              45              50
Arg Leu Ala Ala His Pro Pro Phe Ala Ser Trp Arg Asn Cys Glu Glu Ala Arg Thr Asp Arg Pro Ser Gln Gln
            55              60              65
Leu Arg Ser Leu Asn Gly Leu Glu Ser Arg Ser Ala Gly Met Pro Leu Glu –
```

```
                                                      -5                              0
                                        Met Asp Pro Ser Gly Asp Pro
   *        5              10              15              20              25
Arg Ala Cys Ser Asn Ser Leu Ala Val Val Leu Gln Arg Arg Asp Trp Glu Asn Pro Gly Val Thr Glu Leu Asn
            30              35              40              45    *         50
Arg Leu Ala Ala His Pro Pro Phe Ala Ser Trp Arg Asn Ser Glu Glu Ala Arg Thr Asp Cys Pro Ser Gln Gln
            55              60              65
Leu Arg Ser Leu Asn Gly Leu Glu Ser Arg Ser Ala Gly Met Pro Leu Glu –
```

FIG. 15E

AMINO ACID SEQUENCES

ED8

```
                                                       -5
                                   Met Asp Pro Ser Gly Asp Pro
                                                              0
               5                  10                 15       *  20                25
Arg Ala Ser Ser Asn Ser Leu Ala Val Val Leu Gln Arg Arg Asp Trp Glu Asn Pro Cys Val Thr Glu Leu Asn
              30                  35                 40                            45                50
Arg Leu Ala Ala His Pro Pro Phe Ala Ser Trp Arg Asn Ser Glu Glu Ala Arg Thr Asp Arg Pro Ser Gln Gln
              55                  60                 65
Leu Arg Ser Leu Asn Gly Leu Glu Ser Arg Ser Ala Gly Met Pro Leu Glu —
```

```
                                                       -5
                                   Met Asp Pro Ser Gly Asp Pro
                                                              0
  *            5                  10                 15          20                25
Arg Ala Lys Ser Asn Ser Leu Ala Val Val Leu Gln Arg Arg Asp Trp Glu Asn Pro Gly Val Thr Glu Leu Asn
              30                  35                 40                            45                50
Arg Leu Ala Ala His Pro Pro Phe Ala Ser Trp Arg Asn Ser Glu Glu Ala Arg Thr Asp Arg Pro Ser Gln Gln
              55                  60                 65
Leu Arg Ser Leu Asn Gly Leu Glu Ser Arg Ser Ala Gly Met Pro Leu Glu —
```

AMINO ACID SEQUENCES

```
            -20                  -15                  -10                  -5                   0
            Met Asp Pro Ser Gly Asn Pro Tyr Gly Ile Asp Pro Thr Glu Ser Ser Pro Gly Asn Ile Asp Pro
             5                   10                   15                   20                   25
Arg Ala Ser Ser Asn Ser Leu Ala Val Val Leu Gln Arg Arg Asp Trp Glu Asn Pro Gly Val Thr Glu Leu Asn
             30                   35                   40      *            45                   50
Arg Leu Ala Ala His Pro Pro Phe Ala Ser Trp Arg Asn Ser Glu Glu Ala Arg Thr Asp Lys Pro Ser Gln Gln
             55                   60                   65
Leu Arg Ser Leu Asn Gly Leu Glu Ser Arg Ser Ala Gly Met Pro Leu Glu -
```

```
                                                                                        -5                   0
                                                                    Met Asp Pro Ser Gly Asp Pro
             5                   10                   15                   20                   25
Arg Ala Ser Ser Asn Ser Leu Ala Val Val Leu Gln Arg Arg Asp Trp Glu Asn Pro Gly Val Thr Glu Leu Asn
             30                   35      *            40                   45                   50
Arg Leu Ala Ala His Pro Pro Phe Ala Ser Trp Arg Asn Lys Glu Glu Ala Arg Thr Asp Arg Pro Ser Gln Gln
             55                   60                   65
Leu Arg Ser Leu Asn Gly Leu Glu Ser Arg Ser Ala Gly Met Pro Leu Glu -
```

AMINO ACID SEQUENCES

ED17

```
                                                              -5            0
                                        Met Asp Pro Ser Gly Asp Pro
       *           5                 10               15              20           25
Arg Ala Lys Ser Asn Ser Leu Ala Val Val Leu Gln Arg Arg Asp Trp Glu Asn Pro Gly Val Thr Glu Leu Asn
                  30                 35               40        *     45               50
Arg Leu Ala Ala His Pro Pro Phe Ala Ser Trp Arg Asn Ser Glu Glu Ala Arg Thr Asp Lys Pro Ser Gln Gln
                  55                 60               65
Leu Arg Ser Leu Asn Gly Leu Glu Ser Arg Ser Ala Gly Met Pro Leu Glu -
```

FIG. 15 I

METHODS FOR PROTEIN BINDING ENZYME COMPLEMENTATION

This is a continuation of U.S. Ser. No. 841,125 (now abandoned) filed Feb. 25, 1992, which is a continuation of U.S. Ser. No. 788,370 (now U.S. Pat. No. 5,120,653) filed Oct. 22, 1985, which is a continuation-in-part of U.S. Ser. No. 721,267 (now U.S. Pat. No. 4,708,929) filed Apr. 8, 1985, which is a continuation-in-part of U.S. Ser. No. 666,080 (now abandoned) filed Oct. 29, 1984, which is a continuation-in-part of U.S. Ser. No. 585,356 (now abandoned filed Mar. 1, 1984.

TABLE OF CONTENTS

1. Field of the Invention
2. Background of the Invention
   2.1. Immunoassay Systems
   2.2. Enzyme Immunoassay Systems
   2.3. Complementation and β-galactosidase
   2.4. Hepatitis B Virus Surface Antigen
3. Summary of the Invention
4. Brief Description of the Figures
5. Detailed Description of the Invention
   5.1. Enzyme-donors
      5.1.1. Enzyme-donors: Improved Coupling Chemistries
      5.1.2. Enzyme-donors: Fusion Proteins
   5.2. Enzyme-acceptors
   5.3. Analytes
   5.4. Enzyme Substrates
   5.5. Analyte-binding Proteins
6. Examples: Preparation of Enzyme-donors and Enzyme acceptors by Recombinant Methods
   6.1. Enzyme-donors
      6.1.1. p125 Enzyme-donor
      6.1.2. H, B, M and P Series Enzyme-donors
      6.1.3. p148 Enzyme-donor
      6.1.4. Enzyme-donor 3
      6.1.5. Enzyme-donor 3A
      6.1.6. ED Enzyme-donor Series
   6.2. Enzyme-acceptors
      6.2.1 Comparison of Complementation Efficiency
7. Example: Enzyme Immunoassay for Thyroxine
   7.1. Preparation of Enzyme-acceptor
   7.2. Preparation of Enzyme-donors
   7.3. Thyroxine Immunoassay
8. Example: Hepatitis B Virus Surface Antigen Assay
   8.1. N-terminal Fusion
   8.2. C-terminal Fusion
   8.3. Enzyme Immunoassay For HBV-SAg
9. Example: Hepatitis B Virus Core Antigen Assay
10. Example: Immunoassay for Human Chorionic Gonadotropin
    10.1. Preparation of Human Chorionic Gonadotropin Enzyme-donor Fusion Peptides by Recombinant Methods
    10.2. Human Chorionic Gonadotropin Assay
11. Example: Assay for Biotin
12. Example: Heterogeneous Complementation Assay for Biotin
    12.1. Inhibition of CNBr2-biotin Complementation Activity by Avidin-agarose
    12.2. Competition of Biotin with CNBr2-biotin Conjugate for Immobilized Avid in
13. Example: Enzyme Immunoassay for Digoxin
    13.1. Preparation of digoxin-H6 Conjugate
    13.2. Immunoassay for Digoxin
    13.3. Mechanism of Digoxin Immunoassay
       13.3.1. Effect of Anti-digoxin Antibody on Complementation Using a Variety of Enzyme-acceptors
14. Example: Effect of a Second Antibody on the Digoxin Enzyme Immunoassay
    14.1. Attachment of Whole Secondary Antibody
       14.1.1. Dose Response: EA14 and Digoxin-P6
    14.2. Attachment of Fragment of Secondary Antibody
    14.3. Inhibition of Complementation by Analyte-specific Antibodies: A Comparison of ED-Digoxin Conjugates
15. Improved Thyroxine and Digoxin Assays Utilizing Secondary Antibody
16. Comparison of Performance of Genetically Engineered and Chemically Synthesized Enzyme-donors in Digoxin Immunoassay
17. Deposit of Microorganism

1. FIELD OF THE INVENTION

This invention relates to improved methods and novel compositions for qualitative and quantitative analysis of analytes by enzyme complementation assays. More specifically, the invention relates to altered enzymes, derived both by recombinant DNA techniques and chemical polypeptide synthesis techniques, and methods for use of such enzymes in homogeneous and heterogeneous enzyme immunoassays. Also encompassed are recombinant DNA-derived and chemically synthesized enzymes and methods for use of such enzymes in homogeneous and heterogeneous receptor-ligand complementation assays.

2. BACKGROUND OF THE INVENTION

2.1 Immunoassay Systems

The prior art teaches many immunoassays based on the pioneering development of radioimmunoassay (RIA) by Yalow and Berson, 1960, J. Clin. Invest., 39:1157). RIAs are characterized by competing fixed amounts of radiolabeled analytes with unknown quantities of unlabeled analytes for fixed amounts of specific antibody. The amount of radioactive analyte either bound to antibody or free in solution is quantitated in an appropriate counter and the concentration of non-radioactive analyte determined. Improvements on this general scheme have included: (1) substitution of the radioactive tracer with enzyme or fluorescent tracers, (2) substitution of polyclonal animal antibodies with monoclonal antibodies, (3) improved methods of signal detection including spectrophotometers, fluorometers, fluorescence polarizers and particle counters, and (4) the introduction of homogeneous assays not requiring physical separation of bound tracer from free tracer. Separation of bound tracer from free tracer frequently requires solid supports such as plastic, paper, glass or acrylamide. Customarily antibody is bound to the solid phase whereas tracers and unknowns are free in solution. The bound/free separation is accomplished by one or more washes of the solid phase. The residual bound activity is then measured. These assays are known collectively as heterogeneous immunoassays. In comparison, homogeneous assays obviate the need for the imprecise and time-consuming separation steps.

Commercialization of immunoassays has seen a shift in usage from radioimmunoassays, to enzyme-linked immunosorbent assays (ELISA), to homogeneous assays. This shift is due to the commercial demands of speed, simplicity, automation and absence of radioactivity. Homogeneous assays consist of several types: (1) nephelometry, (2) particle counting, (3) fluorescent quenching, (4) fluorescence polarization, and (5) enzyme assays.

The first nephelometer to measure light dispersion to quantitate immune reactions was devised in the late 1960s. These early nephelometers were improved ten years later with new chemistries, lower angles for measuring dispersion angles and the ability to measure the rate of the antigen-antibody reaction during the first seconds after mixing the reactants (Ritchie, Alper and Graves, 1969, Arthritis Rheum. 12:693; Deaton et al., 1976, Clin. Chem. 22:1465). These assays are of extremely poor sensitivity and are applicable to determinations of analytes at concentrations greater than $10^{-8}$M, e.g., serum IgE, IgA and IgM levels. In homogeneous particle counting assays, polystyrene particles 0.8 μm in diameter (latex particles) are coated by antibodies. Antigen concentrations can be determined by the concentration of latex particles agglutinated as determined by an instrument capable of distinguishing agglutinated versus non-agglutinated particles (Cambiaso et al., 1977, J. Immunol. Meth. 18:33). Homogeneous fluorescent quenching assays label either antigens or antibodies with a fluorophor. Analyte-antibody-fluorophor complexes yield significantly less fluorescence compared to the antigen-fluorophor or antibody-fluorophor alone (Ullman et al., 1979, J. Biol. Chem. 251:4172; U.S. Pat. Nos. 3,998,943; 3,996,345; 4,174,384; 4,161,515; 4,208,479 and 4,160,016). All these assays involve various methods of quenching fluorescence such that the amount of quenching is related to the amount of the unknown analyte or antibody in the sample. These assays are of low sensitivity (analytes at fluid concentrations greater than $10^{-10}$M). The low sensitivity is due to endogenous serum fluorescence and the use of fluorescence in a static non-enzymatically amplified manner. Fluorescence polarization assays are based on the free rotation of antigen-fluorophor in solution which is significantly reduced by antibody binding to the antigen-fluorophor and have found considerable commercial success with low molecular weight (under 1000 daltons molecular weight) analytes (Dandliker et al., 1973, Immunochemistry 10:219).

The various immunoassay methods each possess commercial advantages and disadvantages. RIAs are sensitive and easy to set-up but require radioactivity, separation steps and expensive instrumentation. Heterogeneous assays with enzymes or fluorophores eliminate radioactivity and some instrumentation but require separation steps. From a commercial viewpoint it is desirable to eliminate separation steps for several reasons. Separations (1) are labor intensive, (2) are time consuming, (3) require additional equipment, (4) increase variability in results, and (5) preclude high levels of automation. Despite the many commercial advantages of homogeneous immunoassays only three systems, the enzyme-labeled system of Rubenstein et al., U.S. Pat. No. 3,817,837, the substrate-labeled system of Burd et al., 1977, Clin. Chem. 23:1402, and fluorescence polarization (Dandliker et. al., 1973, Immunochemistry) have found commercial success. Yet these three assay systems are limited to small (less than 1000) molecular weight analytes and analytes found in concentrations greater than $10^{-10}$M.

2.2 Enzyme Immunoassay Systems

Enzyme immunoassays have been a very successful type of homogeneous immunoassay. Several variants of homogeneous enzyme immunoassays have found commercial success (1) the enzyme labeled analyte system; and (2) the substrate labeled analyte system. In the enzyme labeled analyte system the enzymatic activity of the label is decreased when specific antibody binds the analyte-enzyme complex. Analyte to be measured competes with a fixed amount of specific antibody for a fixed amount of the analyte. Enzyme activity is directly proportional to the unknown analyte concentration. The following patents have been issued based on this immunoassay system: U.S. Pat. Nos. 3,817,837; 3,852,157; 3,875,011; 3,966,556; 3,905,871; 4,065,354; 4,043,872; 4,040,907; 4,039,385; 4,046,636; 4,067,774; 4,191,613 and 4,171,244. Commercialization of this technology has been limited to low molecular weight analytes and low sensitivity (analytes smaller than 1000 daltons MW at concentrations greater than $10^{-10}$M).

The substrate-labeled fluorescent immunoassay involves covalent coupling of the analyte to a fluorogenic substrate for an enzyme. This analyte-substrate conjugate is not fluorescent. In the absence of antibody the analyte-fluorogenic substrate is hydrolyzed by an enzyme yielding a fluorescent molecular species. In the presence of specific antibody, access to the substrate by the enzyme is curtailed yielding decreased fluorescence (Burd et al., 1977, Clin. Chem. 23:1402; Burd et al., Anal. Biochem. 77:56; and Kohen, Hollander and Bognolaski, 1979, J. Steroid Blochem. 11:161). Commercialization of this assay system has been limited to low molecular weight analytes due to steric considerations, and to analytes at concentrations in fluids greater than $10^{-10}$M due to considerations analogous to those for the fluorescence quenching assays described above.

Numerous homogeneous enzyme immunoasays have been described which have encountered limited commercialization.

U.S. Pat. No. 4,134,792 describes an immunoassay technique utilizing an enzyme modulator such as an enzyme inhibitor or an allosteric effector as a label. When specific antibody binds to an enzyme modulator-labeled analyte, the enzyme modulator can no longer inhibit the activity of the enzyme. Thus, competition of the enzyme modulator-labeled analyte by free analyte restores inhibition of the enzyme modulator. Other patents in this field include: U.S. Pat. Nos. 3,935,074; 4,130,462; 4,160,645 and 4,193,983.

U.S. Pat. Nos. 4,213,893 and 4,318,983 describe enzyme-immunoasays employing cofactor-apoenzyme systems. In particular, U.S. Pat. No. 4,318,983 issued to Hornby et al. (Mar. 9, 1982) describes a method employing flavin adenine dinucleotide (FAD)-labeled conjugates and apoenzymes with which FAD acts as a prosthetic group. U.S. Pat. No. 4,213,893 issued to Corrico et al. (Jul. 22, 1980) describes specific FAD-labeled conjugates, e.g., FAD-labeled thyroxine, which are suitable for use in the Hornby et al. method. FAD-labeled conjugates are monitored by measuring holoenzyme activity generated by incubation of such conjugate with an apoenzyme that requires FAD for catalytic activity. An analyte is covalently coupled to FAD such that the labeled cofactor retains its reactivity with dehydrogenase enzymes. The amount of reduced FAD formed by the dehydrogenase activity is decreased in the presence of antibody specific for the analyte. The fluorometrically monitored appearance of reduced FAD is directly proportional to the amount of analyte (Kohen et al., 1978, in Enzyme-labeled Immunoassay for Hormones and Drugs, S.B. Pal, ed., Walter deGuiter, Berlin and New York, pp. 67–79). A similar system for biotin and 2,4-dinitrofluorobenzene analytes using lactic dehydrogenase and diaphorase has been described (Carrico et al., 1976, Anal. Biochem. 72:271). Both systems suffer from interference from endogenous cofactors and enzymes that are common in serum samples to be analyzed.

Several enzymes have been observed to reform from peptide fragments but only a few regain enzymatic activity including, e.g., ribonuclease A (Richards and Vithayathil, 1959, J. Biol. Chem. 234:1459), staphlococcal nuclease (Light et al., 1974, J. Biol. Chem. 249:2285), and β-galactosidase (Langley and Zabin, 1976, Biochemistry 15:4866). Proteolysis of bovine pancreatic ribonuclease by subtilisin yields two components, a peptide (S-peptide) and a protein (S-protein). Neither S-peptide nor S-protein alone shows appreciable ribonuclease activity. When these components are mixed in molar equivalents, almost the full enzymatic activity is recovered. S-peptide and S-protein reassociate very rapidly and strongly with a $Keq=5\times10^{-9}M$ (Richards and Vithayathil, 1959, Supra). Staphlococcal nuclease shows reconstruction of biologically active enzyme from inactive peptide fragments. Nuclease-T-(6–48), including amino acids 6–48 of the full 149 amino acid staphlococcal nuclease structure, reassociates with Nuclease-T-(50–149) to form active Nuclease-T1 with a first order rate constant of 0.03–0.05/S with little temperature variability (Light, supra). As discussed in greater detail infra (Section 2.3), polypeptide fragments (e.g., M15) from deletion routants of E. coli are known which regain enzymatic activity when combined with small peptide fragments derived from thermally or cyanogen bromide treated β-galactosidase enzyme. One cyanogen bromide-generated fragment is called CNBr2; another is called CNBr24.

More recently, an immunoassay based on the reassociation of such polypeptide fragments was described by Farina and Golke (U.S. Pat. No. 4,378,428 issued Mar. 29, 1983) and by Gonelli et al. (1981, Blochem. and Biophys. Res. Commun. 102:917–923). All experimental examples disclosed therein were based on reassociation of S-peptide/S-protein to generate ribonuclease catalytic activity. An analyte was covalently attached to a small 10 subtilisin cleavage peptide of ribonuclease, i.e., the S-peptide (amino acids 1–20). This was coupled to an analyte and combined with S-protein (amino acids 21–124) to reform active ribonuclease. Antibody specific for the analyte inhibits the reformation of ribonuclease activity. This assay is limited due to the presence of endogenous ribonuclease activity in all non-autoclaved biological solutions.

Other equally serious faults never addressed by this system include the inability to adjust the equilibrium constant of the associating polypeptides, and an inability to create immunoreactive polypeptides which could couple to large molecular weight proteins while still capable of reforming active enzyme. All polypeptides utilized were non-novel catalytically inactive peptides capable of reassociation to form active ribonuclease.

More significant disadvantages with the chemistries proposed by Farina and Golke (U.S. Pat. No. 4,378,428) to attach an analyte to CNBr2 or M15 have been discovered. Attaching an analyte through the available $NH_2$, COOH, and SH groups on either of the polypeptides have, in all cases tested, yielded polypeptides incapable of complementation. Coupling M15 which has many amino, carboxylic acid and sulfhydryl functionalities, inactivated M15 in all cases, even with carefully controlled conditions. Kinetics indicate a single hit to be sufficient to inactivate activity. CNBr2 contains no internal lysines, a single sulfhydryl group and several carboxylic acid groups. In agreement with Langley (Ph.D. thesis entitled "The Molecular Nature of β-galactosidase α-complementation", UCLA, 1975) coupling to the N-terminal α-amino group inactivates complementation activity of CNBr2. In the preparation of CNBr2 (Langley, Fowler and Zabin, 1975, J. Biol. Chem. 250:2587), the sulfhydryl at position 76 is reduced and alkylated with iodoacetic acid prior to the cyanogen bromide cleavage. If the sulfhydryl is not alkylated CNBr2 activity can be retained early in the steps of purification but is lost prior to purification to homogeneity. Also, if the sulfhydryl is alkylated with a maleimide derivative of an analyte instead of iodoacetic acid, insolubility of the conjugate prevents purification. Finally, in all cases tested, coupling to a COOH moiety of CNBr2 inactivated complementation activity. Therefore, it appears to be difficult to use CNBr2 and M15 to prepare appropriate immunoreactive and complementing reagents.

2.3 Complementation and β-Galactosidase

The enzyme β-galactosidase has found wide use in enzyme-linked immunosorbent assays (ELISA) (Engvall and Perimann, 1971, Immunochemistry 8:871) and homogeneous substrate labeled assays (Burd et al., 1977, Clin. Chem. 23:1402). In addition, β-galactosidase forms the basis of a widespread genetic system for DNA cloning and DNA sequencing (Messing, 1983, Methods in Enzymology 101:20).

β-galactosidase is a tetrameric protein having a molecular weight (MW) equal to 540,000 daltons. The four identical monomers consist of 1021 amino acids, each with a MW of 116,000 daltons. The monomeric protein, as shown in FIG. 1, is divided into three regions; (1) the N-terminal proximal segment (the α-region), (2) a middle region, and (3) a C-terminal distal segment (the ω-region).

Mutant polypeptides derived from β-galactosidase are known which can complement or spontaneously restore enzyme activity when added to extracts of appropriate β-galactosidase negative routants. This phenomenon is known as intracistronic complementation. An example of α-complementation is provided by the M15/CNBr2 complement at ion system. The M15 mutant polypeptide lacks amino acids 11–41 of β-galactosidase and exists in solution as an enzymatically inactive dimer. A polypeptide derived from β-galactosidase by cyanogen bromide (CNBr) cleavage, the CNBr2 peptide (CNBr2), consists of amino acids 3–92. CNBr2, when mixed with the dimer M15, promotes spontaneous reconstruction of the β-galactosidase tetramer with full enzymatic activity (Langley and Zabin, 1976, Biochemistry 15:4866). The M15 peptide is known as an α-acceptor and CNBr2 as an α-donor. While this represents a well-studied complementing system, CNBr2 can serve as α-donor for the M112 dimer, a deletion of amino acids 23–31 within β-galactosidase (Lin, Villarejo and Zabin, 1970, Biochem. Biophys. Res. Common. 40:249; Celeda and Zabin, 1979, Blochem. 18:404; Welphy, Fowler and Zabin, 1981, J. Biol. Chem. 256:6804; Langley et al., 1975, Proc. Natl. Acad. Sci. USA 72:1254). Other α-donors include a polypeptide derived by autoclaving β-galactosidase. This peptide, however, has not been purified and its sequence is unknown. α-acceptors other than M15 and M112 have not been described. In the example of complementation of M15 by CNBr2, amino acid sequences 3–10 and 42–96 are both present in duplicate in the enzymatically active complex.

Intracistronic complementation also occurs at the C-terminus of β-galactosidase (the ω-region). The best known sequence data available is for the X90 ω-acceptor peptide that deletes the last 10 amino acids, 1011–1021. The X90 peptide exists as a monomer and can be complemented by CNBr24, a cyanogen bromide digestion product of β-galactosidase consisting of amino acids 990–1021 to reform enzymatically active tetrarner (Welphy et al., 1980, Biochem. Biophys. Res. Common. 93:223).

2.4 Hepatitis B Virus Surface Antigen

DNA from Hepatitis B virus (HBV) has been cloned and propagated in *E. coli* both as a series of fragments and as entire linear molecules after joining to plasmid or lambdoid phage vectors (Burrell et al., 1979, Nature (London) 279:43–47; Charnay et al., 1979, Proc. Natl. Acad. Sci. USA 76:2222–2226; Sninskey et al., 1979, Nature (London) 279:346–468). Subsequently, the surface antigen of HBV (HBV-SAg) has been cloned and expressed in *E. coli* (McKay et al., 1981, Proc. Natl. Acad. Sci. USA 78:4510–4514), yeast (Valenzuela et al., 1982, Nature 298:347); and mammalian cells (Dubois et al., 1980, Proc. Natl. Acad. Sci. USA 77:4549–4553).

3. SUMMARY OF THE INVENTION

The present invention provides improved methods and novel compositions for enzyme complementation assays for quantitative analysis of analytes of both high and low molecular weight (150–30,000 daltons MW), in high ($10^{-15}$M) sensitivity. The assays are capable of automation.

According to the present invention, polypeptides are produced by recombinant DNA techniques or by chemical polypeptide synthesis techniques. [As used herein the term "polypeptide" is inclusive of peptides and proteins.] The polypeptides themselves are enzymatically inactive; however, when reacted together in aqueous medium they associate to form a catalytically active enzyme via a phenomenon known as complementation. β-galactosidase is a favored enzyme because it has several substrates, detectable using spectrophotometric and fluorometric methods, has shown utility in previous commercial immunoassays, can be measured at extremely low concentrations and is well characterized genetically. By creating enzymatic activity from insignificant background a high signal-to-noise ratio can be achieved. The novel polypeptides used in the improved assays of the present invention encompass (a) fusion proteins in which analyte is fused to polypeptide, the product of recombinant genes containing sequences coding for analyte and polypeptide; (b) polypeptides genetically engineered for optimal coupling with analytes; (c) polypeptides chemically synthesized for optimal coupling with analytes; and (d) polypeptides genetically engineered or chemically synthesized for improved stability to such environmental factors as oxidation, heat, pH, enzymatic degradation and the like.

Thus methods are described for creating an immunoassay based upon the use of recombinant DNA techniques of chemical polypeptide synthesis techniques to provide appropriate polypeptides that (1) are capable of complementation, (2) can be systematically adjusted as to their equilibrium constant of reassociation, (3) are capable of interacting with specific binding proteins, and (4) can, by interaction with specific binding proteins, control the formation of active enzyme having the activity characteristic of β-galactosidase.

The genetically engineered and chemically synthesized polypeptides of this invention offer distinct advantages over other complementing enzyme systems. Polypeptides produced by recombinant DNA techniques can be made in large quantity at low cost, can be easily purified to homogeneity and can be made of any size and sequence. Chemically synthesized polypeptides, particularly those that are relatively small in amino acid length, can be made in large yield in unlimited sequence variation. Either preparative technique provides for manipulation of amino acid sequence, leading to polypeptides of improved coupling chemistries, enzymatic reaction kinetics, enzymatic assay sensitivity and/or stability.

The present invention also entails kits for carrying out an assay according to the methods of the invention.

4. BRIEF DESCRIPTION OF THE FIGURES

The invention may be more fully understood by reference to the following detailed description of the invention, examples of specific embodiments of the invention and to the appended drawings in which:

FIG. 1 schematically represents the β-galactosidase polypeptide, together with deletion routants M15, M112 and X90, known in nature. Also represented are selected cyanogen bromide (CNBr) cleavage peptides CNBr2, CNBr2/3-41, and CNBr24.

FIG. 2 (A through D) (not drawn to scale) represents the construction of various recombinant plasmids containing an analyte coupling domain.

FIG. 3 schematically represents N-terminus and C-terminus fusion proteins comprising α-donor domains and a protein domain composed of the Hepatitis B Virus Surface Antigen (HBV-SAg) or the HBV core antigen.

FIG. 4 represents the DNA and amino acid sequences of exemplary novel polypeptide enzyme-donors prepared as described in Section 6.1 of the detailed description. In FIG. 4 * indicates amino acids having reactive groups available for coupling to analytes.

FIG. 5 schematically represents novel polypeptide enzyme-acceptors which represent deletions introduced into the α-region of the β-galactosidase gene together with the native β-galactosidase gene DNA and amino acid sequences. Also shown for comparison are known deletion routants M15 and M112.

FIG. 6 graphically represents a competitive binding curve for a homogeneous assay for biotin wherein the analyte-binding protein is avidin.

FIG. 7 graphically represents a competitive binding curve (dose response curve) for an assay for biotin wherein the analyte-binding protein is avidin.

FIG. 8 graphically represents a competitive binding curve demonstrating inhibition of complementation of enzyme-donor CNBr2 and enzyme-acceptor EA23 wherein the analyte-binding protein is agarose-immobilized avidin.

FIG. 9 (A and B) graphically represents the effects of various combinations of concentrations of enzyme-acceptor EA23 and enzyme-donor digoxin conjugate on enzyme immunoassay for digoxin. FIG. 9A represents the dose-response curves obtained with EA23 fixed at $5 \times 10^{-8}$M and enzyme-donor conjugate at 1:20 and 1:30 dilutions. FIG. 9B represents the dose-response curves obtained with EA23 fixed at $1 \times 10^{-7}$M and enzyme-donor conjugate at 1:20 and 1:30 dilutions.

FIG. 10 graphically represents dose-response curves for an immunoassay for digoxin wherein a secondary antibody, goat anti-rabbit antibody, is utilized to enhance the inhibitory effects of antibody interaction with enzyme-donor conjugate on the complementation process.

FIG. 11 (not drawn to scale) is a diagrammatic representation of plasmid p169, indicating various genetic regions and restriction enzyme cleavage sites.

FIG. 12 represents the nucleotide sequence of portions of genes coding for ED1 and ED3. Relevant amino acid sequences and restriction enzyme cleavage sites are indicated. The asterisk on the Cys residue of the ED3 N-terminal fragment indicates an analyte coupling residue.

FIG. 14 represents the amino acid sequence of ED3 and ED3A. The asterisks over the Cys residues indicate an analyte coupling residue.

FIG. 15 represents the amino acid sequences of the ED enzyme donor series wherein FIGS. 15A, 15B, 15C, 15D, 15E, 15F, 15G, 15H and 15I represent the amino acid sequence of ED3, ED4, ED5, ED7, ED8, ED13, ED14, ED15 and ED17, respectively. The asterisks over certain residues indicates an analyte coupling residue.

Figure 17:
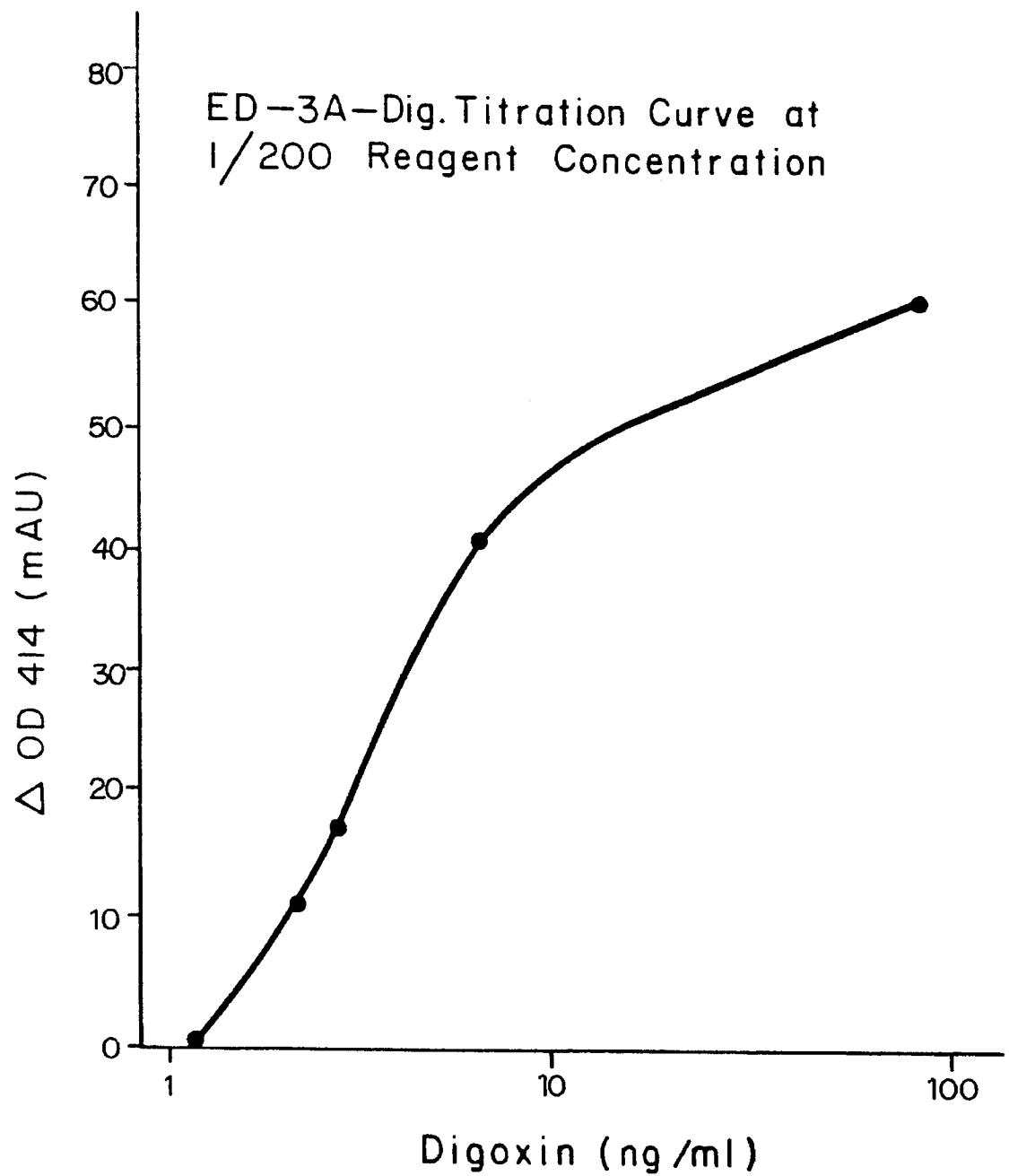

FIG. 17 graphically represents a titration curve for digoxin using digoxin-ED3A in a digoxin enzyme immunoassay.

Figure 18:
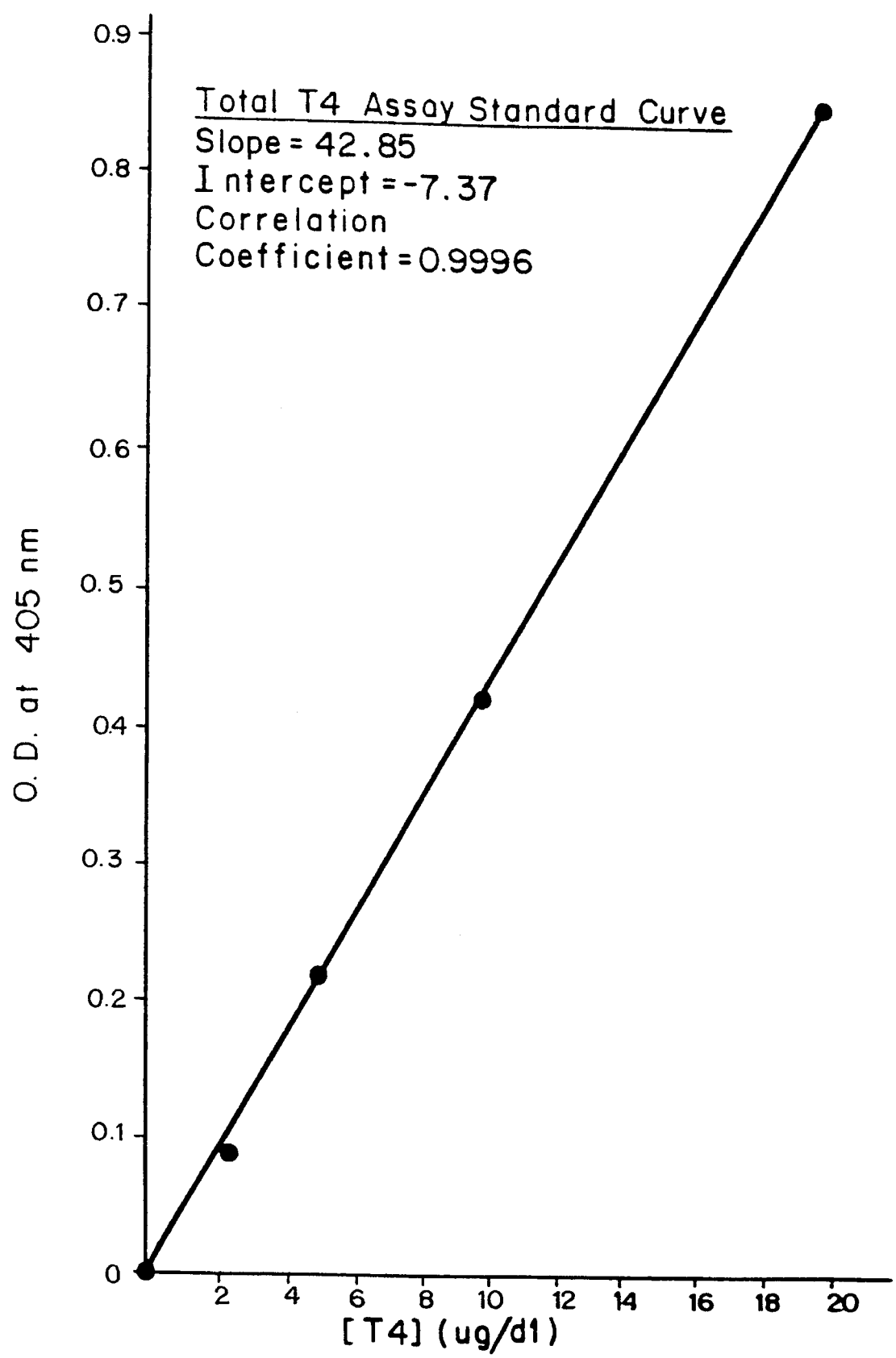

FIG. 18 graphically represents a standard curve from a thyroxine (T4) assay employing ED4-T4, EA22 and secondary antibody.

Figure 19:
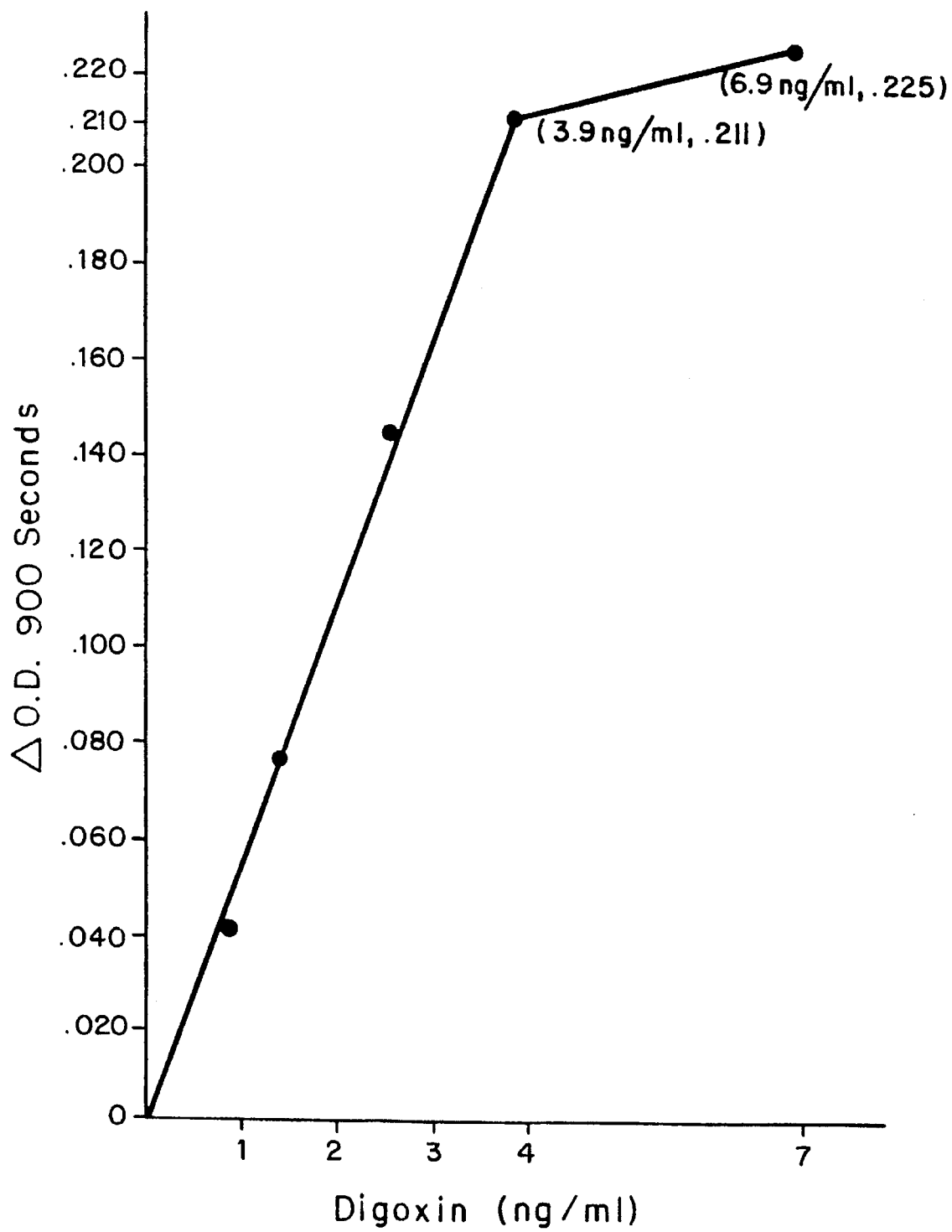

FIG. 19 graphically represents a standard curve from a digoxin assay employing ED5-digoxin, EA22 and secondary antibody.

Figure 20:
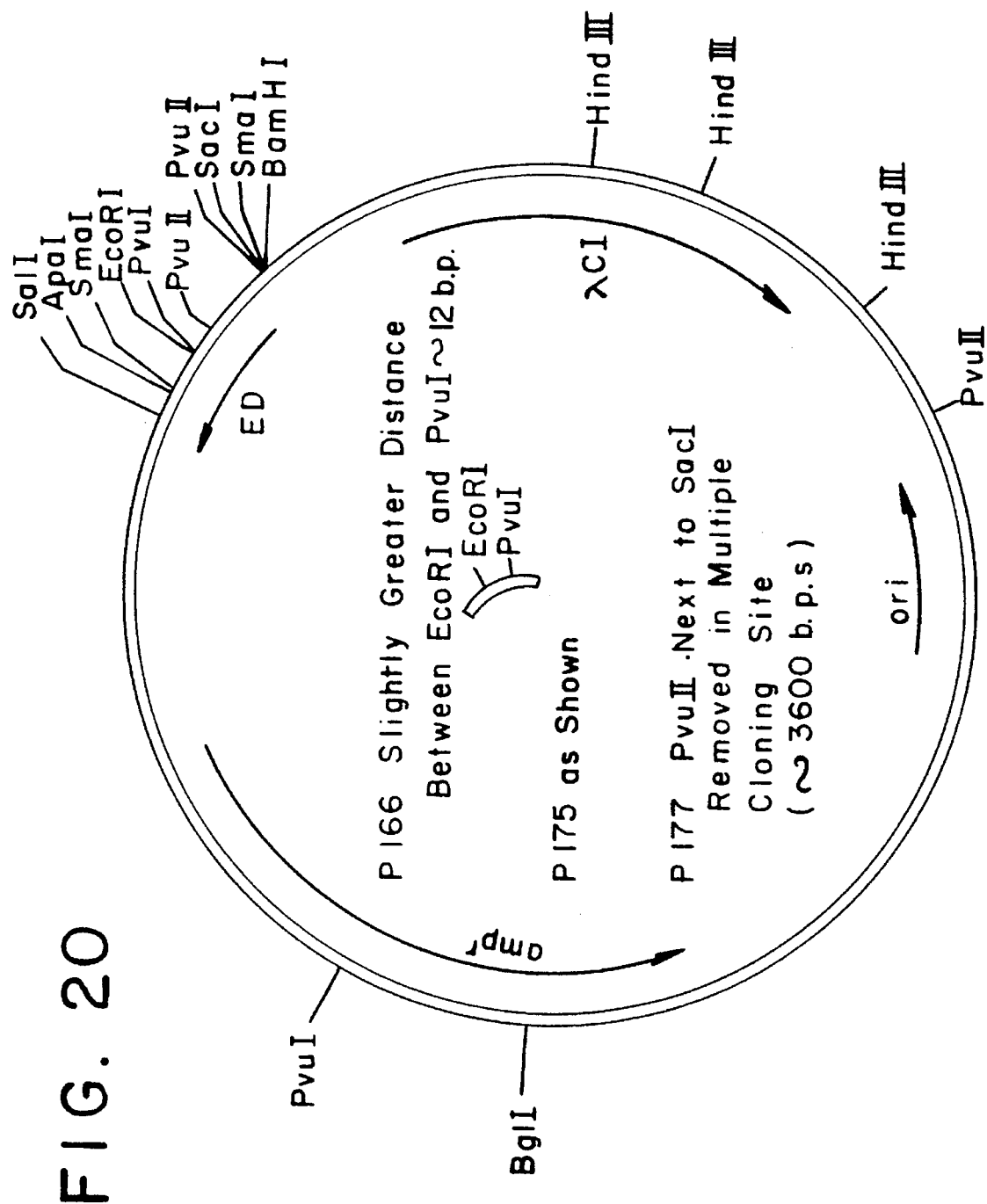

FIG. 20 (not drawn to scale) is a diagrammatic representation of plasmids p166, p175, p177, indicating various genetic regions and restriction enzyme cleavage sites.

Figure 21:
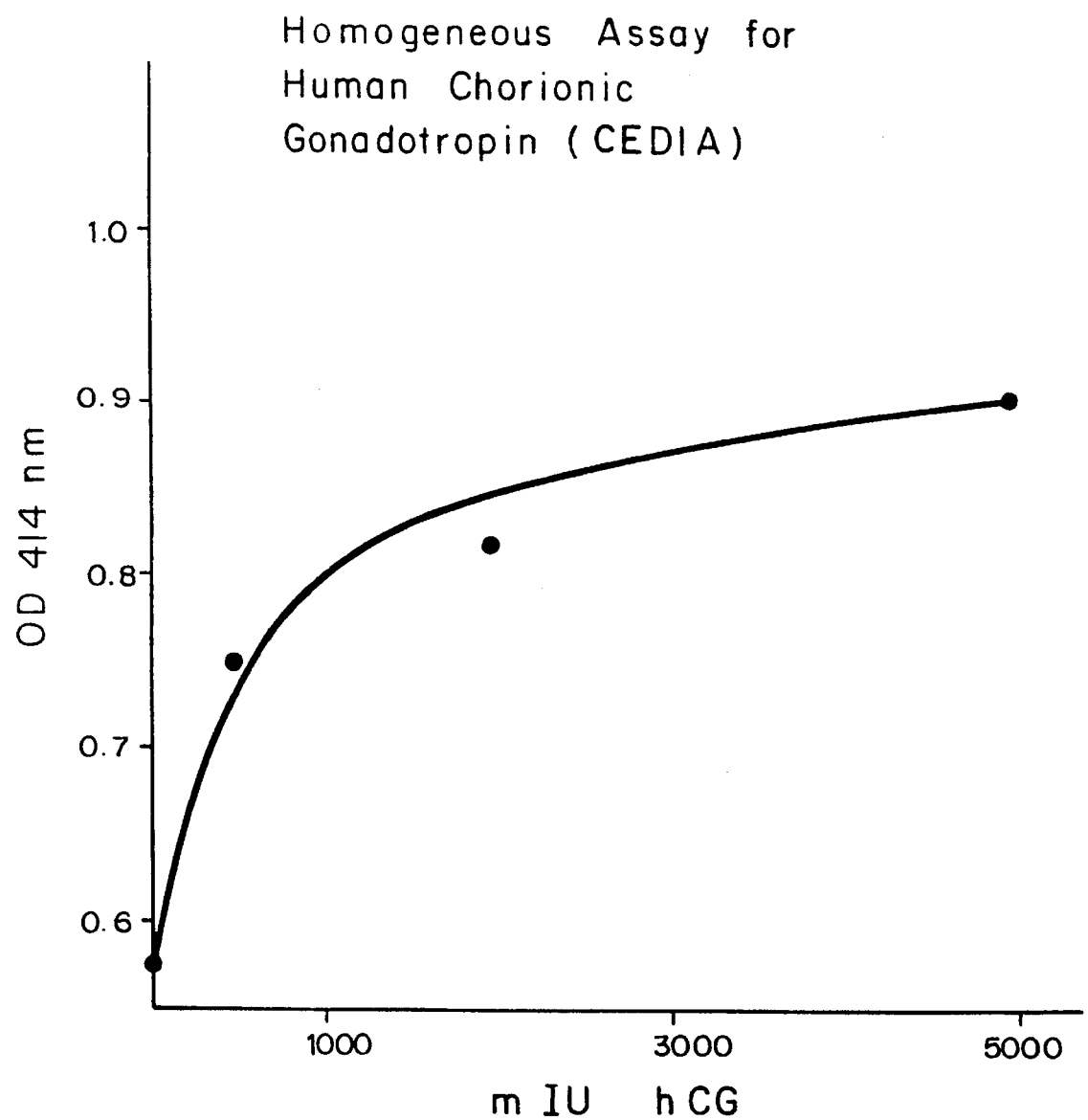

FIG. 21 graphically represents a dose response curve for a homogeneousassay for human chorionic gonadotropin.

5. DETAILED DESCRIPTION OF THE INVENTION

The present invention comprises improved assays for a variety of analytes employing enzymatically inactive polypeptides prepared using recombinant DNA techniques or chemical polypeptide synthesis techniques which when incubated together in aqueous medium form an active β-galactosidase enzyme complex by the process of complementation. According to the methods of the present invention, recombinant DNA techniques may be used to prepare one or both polypeptides required for complementation. The two polypeptides are termed (1) an enzyme-acceptor and (2) an enzyme-donor. DNA synthesis techniques are applied to the preparation of gene sequences coding for polypeptides of a variety of lengths. Enzyme donors and enzyme acceptors are prepared by those techniques. Chemical polypeptide synthesis techniques are generally applied to the preparation of polypeptides that are relatively short in amino acid length. For this reason, chemical techniques are best suited for the synthesis of enzyme-donors of the β-galactosidase system, since the enzyme-donors of this system are typically short in amino acid sequence compared to the enzyme-acceptors. Of course, this is not to say that functional enzyme-acceptors cannot be prepared by peptide synthesis techniques.

As defined herein, an enzyme-acceptor is an enzymatically inactive polypeptide produced by a deletion mutant of the β-galactosidase gene which when combined with an enzyme-donor is capable of forming active β-galactosidase by the process of complementation. All enzyme-acceptors constructed herein are deletions within the α-region of the β-galactosidase gene encoding the N-terminus of the β-galactosidase protein. Some of these enzyme-acceptors have been further manipulated through removal of exposed cysteine residues to provide for greater stability.

As defined herein, an enzyme-donor is an enzymatically inactive polypeptide comprised of two domains: (a) an α-donor domain containing a protein sequence capable of combining with an enzyme-acceptor to form active enzyme; and (2) an analyte domain capable of interacting with an analyte-binding protein. The analyte domain is either (1) an analyte-coupling domain or (2) a protein domain.

As defined herein, an analyte-coupling domain comprises amino acids inserted or substituted into the polypeptide to provide convenient sites for the covalent coupling of analytes. The chemical coupling sites are most frequently sulfhydryl or amino groups associated with cystine or lysine residues, but can be any appropriate chemically reactive group of any amino acid which is capable of binding to analyte without interfering with (a) the process of complementation or (b) interaction of the analyte with an analyte-binding protein. The location of the chemically reactive group can be altered to meet the steric hindrance requirements of the assay.

As defined herein, a protein domain comprises a protein antigen or an immunoreactive group of an antigen (epitope). For example, antigens such as tumor, bacterial, fungal, viral, parasitic, mycoplasmal, histo-compatability, differentiation and other cell membrane antigens, pathogen surface antigens, toxins, allergens, drugs and any biologically active molecules including but not limited to gonadotropin hormone, follicle stimulating hormone, thyroid stimulating hormone, ferritin, or any other antigenic molecule corresponding to or analogous to an analyte are possible. As defined herein, enzyme-donors wherein the analyte domain is a protein domain are also termed "fusion proteins". While all the enzyme-donors constructed by genetic engineering represent gene fusions encoding fusion proteins with α-donor domains and analyte domains, the term "fusion protein" as defined herein is applicable only to those enzyme-donors comprised of an α-donor domain and a protein domain specifying immunoreactive epitopes of a protein antigen. [It is of course, possible for the protein domain to comprise a nonimmunoreactive protein or fragment thereof capable of interacting with an analyte binding protein other than an antibody.] The protein domain of fusion proteins obviates the need to covalently couple an analyte to the analyte domain as is necessary where the analyte domain is an analyte-coupling domain. This is because the protein domain portion of a fusion protein is, in essence, an analyte (or, at least, a close analogue of one) capable of competing with free analyte for analyte-binding proteins.

As in any enzyme assay for analyte contained in a sample or medium, an analyte-binding protein included as a reagent in the assay mixture must competitively interact or combine with both free analyte and with analyte coupled to or fused as part of the analyte domain of the enzyme-donor. Interaction of the analyte-binding protein with analyte coupled to or fused within the enzyme-donor (hereinafter termed "enzyme-donor conjugate") must inhibit the process of complementation of enzyme-donor and enzyme-acceptor. As defined herein, analyte-binding proteins include specific antibody molecules including conventional (polyclonal) and monoclonal antibodies (and fragments thereof), receptors, transport proteins, lectins, and other binding proteins, including but not limited to avidin, thyroxine binding globulin, etc. As defined herein, the term analyte-binding protein encompasses proteinaceous substances such as glycoproteins, lipoproteins, etc.

The improved enzyme assay methods of the present invention are based upon competitive binding mechanisms. According to the present invention, a known amount of enzyme-donor of the β-galactosidase system comprising a coupled or fused analyte (or an analogous analyte derivative) of interest (i.e., enzyme-donor conjugate) is combined with a known amount of a specific analyte-binding protein and a known amount of an enzyme-acceptor capable of complementation with the enzyme-donor. Competition between the analyte domain of the enzyme-donor conjugate and free unknown analyte in the sample for the known amount of specific analyte-binding protein frees the enzyme-donor conjugate so that it binds to the enzyme-acceptor. The association of enzyme-donor conjugate and enzyme-acceptor results in the formation of a catalytically active enzyme complex, thus modulating the amount of β-galactosidase enzyme activity detectable in the sample. As a result the amount of free analyte in the sample is determined as a direct function of the measureable enzyme activity. Enzyme activity is measured by monitoring the rate of substrate conversion by the enzyme catalyzed reaction by any of a variety of techniques including but not limited to spectrophotometric, and fluorometric methods. The competitive reactions of the present assay may be represented as follows:

where in the analyte, enzyme-donor conjugate, enzyme-acceptor, analyte-binding protein, and β-galactosidase enzyme are respectively: A; ED~A; EA; Abp and E

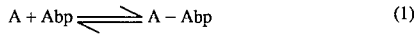  (1)

  (2)

where $k_{2a}$ and $k_{2d}$ represent constants of association and disassociation of enzyme-donor conjugate and analyte-binding protein;

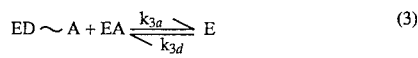  (3)

where $k_{3a}$ and $k_{3d}$ represent constants of association and disassociation of enzyme-donor conjugate and enzyme-acceptor polypeptides Binding of the analyte-binding protein (Abp) to an accessible determinant on the enzyme-donor conjugate (ED~A) inhibits the complementation reaction such that the enzyme-acceptor remains an inactive dimer.

Thus, reaction (2)

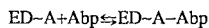

competes with reaction (3)

Using known concentrations of Abp, ED~A, and EA, the activity of the complexed β-galactosidase [E] will be directly proportional to the unknown concentration of free analyte of interest in the sample.

As in conventional enzyme assays, for satisfactory sensitivity, formation of active enzyme by complementation of the enzyme-donor conjugate coupled to analyte-binding protein together with the enzyme-acceptor must be minimal. Stated in other words, either or both reactions (4) and (5) below must proceed only minimally or not at all.

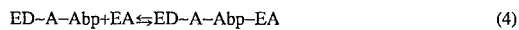  (4)

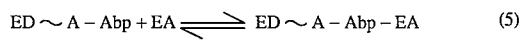  (5)

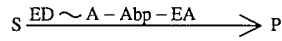

wherein ED~A; Abp; and EA are as described above; and substrate and product for the reaction catalyzed by active enzyme (E) are respectively: S and P.

A critical component for designing a particular assay with satisfactory sensitivity is the relationship among: (1) the association constant for the enzyme-donor conjugate and enzyme-acceptor ($k_{3a}$) (2) the concentration of specific analyte-binding protein ([Abp]); (3) the association constant for specific analyte-binding protein and enzyme-donor conjugate ($k_{2a}$); and the concentration of enzyme-acceptor ([EA]).

The following inequalities suggested by Farina and Golke (U.S. Pat. No. 4,378,428), may be used as a guide in designing a particular assay:

$$\frac{K_3 [Abp]}{K_1} \geq = [EA] \geq [ED \sim A] + K_3$$

where $K_1$ and $K_3$ represent the equilibrium constants for reactions (1) and (3), and [Abp], [EA] and [ED~A] are respectively the concentrations of analyte-binding protein, enzyme-acceptor and enzyme-donor coupled to analyte. This analysis assumes that the equilibrium constants for reactions (1) and (2) above are identical and that reactions (4) and (5) do not proceed at all.

As explained in greater detail by Farina and Golke (supra), it is generally desirable that the assay be designed such that the expression $$\frac{K_3 [Abp]}{K_1}$$

is approximately 2 to 100 times greater than [EA], preferably about 5 to 25 times. Further, the concentration of ED~A should be within a factor of about 10 to 100 times that of the anticipated unknown analyte concentration. This permits the amount of catalytically active enzyme formed in reaction (3) to respond satisfactorily to varying analyte concentrations in the samples to be assayed.

The components of the enzyme complementation assays of the present invention may be packaged in a kit either in aqueous medium or in lyophilized form. Each component or reagent can be packaged either separately or with another component so long as the sensitivity of the assay is not altered and the component is not adversely affected. One commercial embodiment of the kits is termed Cloned Enzyme-Donor Immunoassay [CEDIA™].

5.1 Enzyme-Donors

According to the present invention, improved enzyme assays are achieved by use of enzyme-donors and enzyme-acceptors prepared using recombinant DNA techniques and/or chemical polypeptide synthesis techniques. Such techniques permit improved chemistry for covalent coupling between enzyme-donors and analytes via insertion or substitution of amino acids having the appropriate reactive groups, e.g., amino, sulfhydryl, carboxyl, etc. Such techniques permit more precise control of the association constant between enzyme-acceptor and enzyme-donor by systematically determining the amino acid sequence of the complementing polypeptides. Additionally, such techniques yield inexpensive, reliable sources of these polypeptides.

5.1.1 Enzyme-Donors: Improved Coupling Chemistries

According to one embodiment of the present invention, enzyme-donors having an α-donor domain and an analyte-domain are prepared by the use of recombinant DNA techniques to improve the chemistry for coupling an analyte to the analyte-domain. These enzyme-donor polypeptides provide convenient coupling sites for the covalent attachment of analyte at varying distances from the α-donor domain sequence required for complementation.

To obtain enzyme-donor polypeptides of the type containing an analyte-coupling domain, the plasmid pUC13, known to persons skilled in the art, (see FIG. 2A) may be cleaved at different sites in the α-region with a variety of enzymes. For example cleavage with HaeII, BglI, MstI or PvuI yields H-series, B-series, M-series and P-series α-regions respectively. The B- and H-series are treated with T4 DNA polymerase and S1 nuclease. The M-series and P-series are not treated. Each series of DNA is digested with SacI in the multiple cloning site and the small DNAs encoding an α-complementing peptide purified by agarose gel purification, electrophoresed onto DEAE-cellulose paper eluted and ethanol precipitated.

Additionally, a plasmid may be genetically engineered to place the α-donor sequence under regulatory control of a temperature inducible promotor. This may be accomplished using a λPr promotor in combination with a λ repressor protein (coded by the λCI gene) which is temperature sensitive, and allows for temperature induction of protein expression. The λ mutant gene, CI857 codes for a temperature sensitive repressor protein, which is inactive at temperatures greater than 37° C. Hereinafter, references to λCI gene refer to the CI857 mutant gene.

According to another embodiment of the present invention, enzyme-donors having an α-donor domain and an analyte-coupling domain are prepared by the use of chemical polypeptide synthesis techniques to improve the chemistry for coupling an analyte to the analyte-domain. These enzyme-donor polypeptides provide convenient coupling sites for the covalent attachment of analyte at varying distances from the α-donor domain sequence required for complementation. Chemical peptide synthesis techniques may also be employed to prepare enzyme-donors comprising an α-domain and a protein domain. Enzyme-donor peptides are synthesized on an automated peptide synthesizer by standard synthetic techniques. Briefly, a protected amino acid representing the carboxy terminus amino acid of the desired peptide is attached to cross-linked polystyrene beads. The resin beads function as a solid phase to which additional amino acids may be coupled in a step-wise manner. The peptide is generated by growing the chain sequentially from the carboxy-terminus to the N-terminus. The solid phase facilitates driving the reaction rapidly to 100% completion by the use of excess reagents. The excess reagents can then be easily washed away. Upon completion of the synthetic steps, the peptide is removed from the resin and purified.

Enzyme-donor polypeptides prepared according to the methods of the present invention have superior coupling chemistry for attachment to analytes than do conventional polypeptides of the CNBr2/M15, CNBr2/M112 and CNBr 24/X90 complementation systems.

Coupling of analytes to M15, which has many amino, carboxylic acid and sulfhydryl groups, inactivated M15 in all cases, even with carefully controlled conditions. Kinetic experiments indicate a single hit to be sufficient to inactivate activity. Analogous results would be expected with M112 and X90.

Covalent attachment of analyte to the CNBr2 peptide via $NH_2$, COOH, and SH groups has in all cases tested, yielded polypeptides incapable of complementation. CNBr2 contains no internal lysines (no available $NH_2$ groups), a single sulfhydryl group and several carboxylic acid groups. Firstly, in agreement with Langley (Ph.D. thesis "The Molecular Nature of β-galactosidase α-complementation", UCLA, 1975) coupling to the N-termal α-amino group has been shown to inactivate complementation activity of CNBr2. In a series of experiments, a number of compounds of varying molecular weight were covalently attached to the single amino group located on the N-terminus of the CNBr2 peptide. The following compounds were reacted with the N-terminal amino group of the peptide: succinic anhydride (MW 100 daltons); biotin-N-hydroxysuccinimide ester (MW 342 daltons ); 4-phenylspiro [furan-2(3HO ,-1'-phthalon]-3,3'-dione (fluorescamine) (MW 278 daltons); and dichlorotriazinylamino fluoroscein-dihydrochloride (MW 568 daltons). Complementation by these enzyme-donor conjugates was compared to complementation by free CNBr2 peptide. The ability of CNBr2 to complement either M15 or EA23 enzyme-acceptor polypeptides was inhibited about 25%, 39%, 46% and 63%, respectively, by the attached compounds. It should be noted that analogous covalent attachment of these same compounds to the N-terminus amino group of enzyme-donor polypeptides prepared by recombinant DNA techniques similarly inhibited complementation. Thus, coupling of analytes, particularly those greater than about 500 daltons MW, to the amino group of the N terminus severely restricts complementation by the enzyme-donor polypeptides.

Secondly, there is no free sulfhydryl group available for covalent attachment of analytes in purified CNBr2 peptide. In the preparation of CNBr2 (Langley, Fowler and Zabin, 1975, J. Biol. Chem., 250:2587), the sulfhydryl at position 76 is reduced and alkylated with iodoacetic acid prior to cleavage by cyanogen bromide. If the sulfhydryl is not alkylated, CNBr2 activity can be retained early in the steps of purification but is lost prior to purification to homogeneity. Also, if the sulfhydryl is alkylated with a maleimide derivative of an analyte instead of iodoacetic acid, insolubility of the conjugate prevents purification.

Thirdly, in all cases tested, coupling to a COOH moiety of CNBr2 inactivated complementation activity. For example, theophylline-8-propylamine was used in an attempt to couple theophylline to CNBr2 with the water soluble carbodiimide 1-ethyl-3-(3-dimethyl-aminopropyl) carbodiimide (EDAC, Sigma Chemical Co., St. Louis, Mo.). Theophylline-8-butyrate was synthesized according to Cook et al. (1976, Res. Comm. Chem. Path. Pharm. 13:497–505) and converted to theophylline-8-propylamine by a modified Curtius rearrangement (Washborne and Peterson, Synthetic Comm. 1972, 2 (4):227–230). The structure of the purified product was confirmed by mass spectroscopy by Dr. T. Vanaman at Duke University. To several tubes containing $2 \times 10^{-11}$ moles of CNBr2 in 0.5 ml of 0.1M $NaPO_4$, pH 7.4 and $1\times10^{-5}$ moles theophylline-8-propylamine, was added decreasing amounts of EDAC. The resultant complementation activity was measured in 0.5M PM2 Buffer with M15 as enzyme-acceptor and o-nitrophynel-β-D-galactopyranoside as substrate. EDAC was dissolved and diluted in cold water just before use and 10 μl of various dilutions added to reaction tubes. Optical density (414 nm) of 1.403; 0.000; 0.000; 0.010; 0.018; 0.125; and 0.983; were measured using concentrations of EDAC respectively, 0; $1\times10^{-6}$; $1\times10^{-7}$; $1\times10^{-8}$; $1\times10^{-9}$; $1\times10^{-10}$; $1\times10^{-11}$ moles. These data show the rapid inactivation of CNBr2 attempted couplings with 1-ethyl-3-(3-dimethylaminopropyl) carbodiimide.

In contrast, the enzyme-donor polypeptides prepared according to the present invention are genetically engineered or chemically synthesized to provide sulfhydryl, amino or carboxyl groups sufficiently or chemically synthesized removed from the N-terminus so that analytes are covalently attached to these groups without interfering with the ability of the enzyme-donor conjugate to form catalytically active enzyme complex with an enzyme-acceptor. Sulfhydryl and amino groups are preferred.

When a free sulfhydryl is present, it can react with a reactive group that is present on the analyte. Such reactive groups include but are not limited to, reactive haloalkyl groups and acid/halo groups, p-mecuribenzoate groups and groups capable of Michael-type addition reactions (including, for example, maleimides and groups of the type described in Mitral and Lawton, 1979, J. Amer. Chem. Soc. 101:3097–3110). Haloalkyl as defined herein 10 comprises any alkyl group from one to three carbon atoms substituted with bromine, iodine or chlorine. If the analyte does not possess such reactive group for coupling to the free sulfhydryl of the enzyme-donor, a derivative of the analyte can be prepared to contain such reactive group.

5.1.2 Enzyme-Donors: Fusion Proteins

According to another embodiment of the present invention, an enzyme-donor polypeptide is prepared by ligating or fusing a gene encoding an α-donor domain with another gene encoding the protein analyte (or a portion thereof) to be assayed. The expression of the ligated genes in an appropriate host cell results in a fusion protein product that is capable both of complementation with an enzyme-acceptor and specific binding to the analyte-binding protein. Thus, fusion proteins prepared according to this embodiment of the present invention comprise two domains: (1) an α-donor domain, and (2) a protein domain, both encoded by a fused gene. As mentioned previously, the protein domains utilized in this invention comprise immunoreactive epitopes of protein antigens.

In order to construct a gene which encodes a fusion protein, the two genes in question must be joined with their coding sequences such that the translational reading frame is maintained and is uninterrupted by termination signals. Further, if the host cell is a strain which contains a repressor, the fusion protein will be produced only in response to inactivation of the repressor of induction. The fusion proteins are identified for their complementation activity by in vivo complementation of an enzyme-acceptor. Screening of genetic constructions for immunoreactivity and immunospecific inhibition of complementation by interaction of antibody with the protein domain are accomplished in vitro.

Fusion proteins can be constructed where the immunoreactive polypeptide is attached to the N-terminus of the α-donor domain or to the C-terminus of the enzyme-donor polypeptide (see FIG. 4). A spacer sequence between the α-donor domain and the protein domain can be used to enhance complementation, or enhance the inhibitory effect of interaction with specific binding protein on complementation.

Further, fusion of an entire gene coding for a particular protein analyte may not be required. For example, the related human glycoproteins leutropin (leuteininzing hormone; LH), follitropin (follicle-stimulating hormone; FSH), thyrotropin (thyroid-stimulating hormone; TSH) and human chorionic gonadotropin (hCG) are comprised of α and β-subunits. The α-subunits of all these hormones are identical. But in each case the β-subunit is distinct and confers the unique specificity and biologic activity of each hormone. Thus only the β-subunit may need to be fused to the α-donor domain sequence to construct an immunoassay specific for a particular hormone of this group.

Alternatively, the immunoreactive sequence coding for the protein domain which is fused to the α-donor coding gene sequence could represent a unique immunoreactive epitope. For example, only the unique carboxy-terminal 30 amino acid extension of the β-subunit of hCG (Birken et al. 1982, Endocrinology 110:1555) may be used as the protein domain in an assay for hCG.

As another illustrative example, the sequence for the entire Hepatitis B Virus surface antigen or only a small portion of this sequence could be used as the immunoreactive epitope for the Hepatitis B virus (Lernere et al., 1981, Proc. Natl. Acad. Sci. USA 78:3403).

The enzyme donors can be prepared by a variety of methods, including recombinant DNA technology including direct synthesis of DNA using a commercial DNA synthesizer and the like.

5.2 Enzyme-Acceptors

As mentioned previously, the constant of association between enzyme-donor and enzyme-acceptor polypeptides is an important parameter for achieving satisfactory sensitivity with any enzyme complementation assay system. According to the present invention, in order to adjust the constant of association between enzyme-donor and enzyme-acceptor, the amino acid sequence of either the enzyme-donor α-domain (see Section 5.1, supra) or the enzyme-acceptor is systematically altered.

Enzyme-acceptors with varied affinities for enzyme-donor are prepared using a variety of recombinant DNA techniques including, but not limited to deletion constructions or direct synthesis of DNA carrying the desired amino acid sequence followed by in frame ligation into the DNA sequence of the α-region of the lacZ gene which encodes native β-galactosidase.

Illustrative techniques for the preparation of enzyme-acceptors by deletion constructions are presented in detail in Section 6 (infra). Very briefly, deletion construction techniques entail introduction of sites specific for particular restriction enzymes into the α-region of the β-galactosidase Z gene, followed by site-specific digestion, e.g., Bal31 digestion, to afford the desired amino acid sequence. After digestion with appropriate restriction enzymes, the viable enzyme-acceptors are isolated using in vivo complementation ability. For example, complementation can be screened by transforming plasmids, bearing thermoinducible genes coding for an enzyme-donor as well as the enzyme-acceptor of interest, into a strain such as AMA1004 (AMA1004 is galU, galK, StrA$^r$, hsdR$^-$, leuB6, trpC, Δ (lacIPOZ)C29

(Casadaban et al., 1983, Methods in Enzymology 100:293) and selecting on plates containing the inducer isopropylthiogalactoside and the chromogenic substrate 5-bromo-4-chloro-3-indolyl-β-D-galactopyranoside. Colonies that are white at 30° C. but blue at 42° C. indicate creation of viable enzyme-acceptors. DNA from these enzyme-acceptors is cut with SalI, religated and transformed into AMA1004. The enzyme-acceptor polypeptides are then purified.

Alternatively, the enzyme-acceptors are prepared by direct synthesis of DNA using any commercial DNA synthesizer. The desired synthetic DNA sequence is then annealed and ligated into an appropriate plasmid vector. For example, plasmid p150 is digested with BamHI and XhoI restriction enzymes. The desired synthetic DNA sequence is then inserted into the BamHI/XhoI gap.

According to another embodiment of the invention, enzyme-acceptors of improved stability are prepared for use in enzyme complementation assays. The instability of enzyme-acceptors is effected most notably by oxidizing conditions. Ethylenediaminetetraacetic acid (EDTA) and reducing agents such as 2-mercaptoethanol or dithiothreitol dramatically improve the stability of enzyme-acceptors. These results point to exposed sulfhydryl groups on the enzyme-acceptors as the cause of instability. According to Jornvall, Fowler and Zabin (Biochemistry 1978, 17:5160–5164) two of the 16 cysteine residues of the monomer polypeptide chain of native β-galactosidase are located on the surface of the enzyme. However, the enzyme-acceptor M15 contains 5 cysteine residues on the surface. Therefore, to improve enzyme-acceptor stability, the exposed cysteine residues are systematically removed from the improved enzyme-acceptors described in Section 6.2. The genes encoding the enzyme-acceptors are cloned into the appropriate M13 bacteriophage, single-stranded DNA isolated and annealed to appropriate oligonucleotide primers synthesized on the Applied Biosystems, Inc. DNA synthesizer. Standard methods as described by Zoller and Smith (Methods in Enzymology 1983 100, 468–500, Academic Press) are used in these constructions.

5.3 Analytes

The improved methods and novel compositions of the present invention can be used to determine the presence and/or quantity of a variety of analytes including drugs and drug metabolites, biologically active molecules, steroids, vitamins, industrial pollutants, pesticides and their metabolites, food additives, herbicides and their metabolites, flavoring agents and food poisons, pathogens and toxins they produce, and other substances of interest. Analytes of relatively high molecular weight, e.g., proteins with MW greater than about 2,000 daltons, as well as smaller analytes can be detected and/or measured with the improved assays and compositions of this invention. Illustrative examples of such analytes include, but are not limited to, the following:

| HIGH MOLEUCLAR WEIGHT | LOW MOLECULAR WEIGHT |
| --- | --- |
| Carcinoembryonic antigen | Estriol |
| Ferritin | Digoxin |
| Human T-Cell Leukemia Virus | Thyroxine |
| Insulin | Propranolol |
| α-fetoprotein | Methotrexate |
| Rubella Virus | Phencyclidine |
| Herpesvirus | Methadone |
| Cytomegalovirus | Morphine |
| Follicle stimulating hormone | Diazepam |
| Thyroid stimulating hormone | Oxazepam |
| Leutinizing hormone | Quinidine |
| Hepatits Virus | Propoxyphen |
| Chorionic Gonadotropin | N-acetylprocainamide |
| Estrogen receptor | Secobarbital |
| Thyroid stimulating hormone receptor | Tobramycin |
| Poliovirus receptor | Gentamicin |
| Insulin trasnport protein | Theophylline |
| Protein A | Amphetamine |
| Con A lectin | Benzoyl ecogonine |
| Wheat Germ agglutinin lectin | Phenytoin |
| Secretory protein | Procainamide |
| Cholera toxin | Lidocaine |
| Avidin | Carbamazepine |
| | Primidene |
| | Valproic Acid |
| | Phenobarbital |
| | Ethosuxinimide |
| | Biotin |

5.4 Enzyme Substrates

In the improved enzyme assays of the present invention, the amount of unknown analyte in a sample mixture is measured as a direct function of the activity of the β-galactosidase enzymes. Enzyme activity is monitored by the appearance of a product of the enzymatically catalyzed reaction or by disappearance of the enzyme substrate. This is the rate of conversion of substrate. Substrates for β-galactosidase that are suitable for spectrophotometric or fluorometric analysis include, but are not limited to: p-aminophenyl-β-D-galactopyranoside; 2'-N-(hexadecanol)-N-(amino-4'-nitrophenyl)-β-D-galactopyranoside; 4-methylumbelliferyl-β-D-galactopyranoside; napthyl-AS-B1-β-D-galactopyranoside; 1-napthyl-β-D-galactopyranoside; 2-napthyl-β-D-galactopyranoside monohydrate; O-nitrophenyl-β-D-galactopyranoside; m-nitrophenyl-β-D-galactopyranoside; p-nitrophenyl-β-D-galactopyranoside; and phenyl-β-D-galactopyranoside, 5-bromo-4-chloro-3-indolyl-β-D-galactopynanoside, resorufin-β-D-galactopyranoside, 7-hydroxy-4-trifluoromethyl coumarin, ω-nitrostyryl-β-D-galactopyranoside, and flourescein-β-D-galactopyranoside.

5.5 Analyte-Binding Proteins

The enzyme assays of the present invention utilize competitive interaction for an analyte-binding protein between free analyte and enzyme-donor conjugate. Interaction of enzyme-donor conjugate inhibits the complementation reaction. As described in detail in examples in Sections 12 and 13 (infra), attachment of antibody or antibody fragment specific for the analyte-binding protein may be useful to enhance steric hinderance effects and thus contribute to the inhibition of complementation by the enzyme-donor conjugate bound to the analyte-binding protein.

According to one embodiment of the present invention, the analyte-binding protein is an antibody molecule. In such case, the assay is an enzyme immunoassay. The antibody molecules useful for such assays include both conventional (polyclonal) and monoclonal antibodies (and fragments of polyclonal or monoclonal antibodies) specific for the analyte to be measured.

According to another embodiment of the present invention, the analyte-binding protein is avidin, which has special affinity for biotin. In such case the enzyme assay is useful to measure not only biotin, but derivatives of biotin which retain affinity for avidin.

According to another embodiment of the present invention, the analyte-binding protein is a binding protein including, but not limited to receptors, lectins, transport proteins, etc.

6. EXAMPLES: PREPARATION OF ENZYME-DONORS AND ENZYME-ACCEPTORS BY RECOMBINANT METHODS

In all the following experiments, all DNA restriction and modification enzymes were obtained from New England Biolabs (Beverly, Mass.) and were used according to the manufacturer's instructions.

6.1 Enzyme-Donors

6.1.1 p125 Enzyme-Donor

The plasmid p125 was genetically engineered to place an α-donor sequence under regulatory control of a temperature inducible promotor (λPr). In addition, the expressed α-donor peptide contains a unique cysteine residue near the C-terminal end. This was accomplished by cleaving the plasmid pUC13 with BglI and the resultant single-stranded termini were removed by treatment with S1 nuclease. The plasmid was then digested with BamHI. The approximately 170 bp DNA fragment encoding the β-galactosidase α-gene was then purified by agarose gel electrophoresis. (See FIG. 2).

Figure 1:
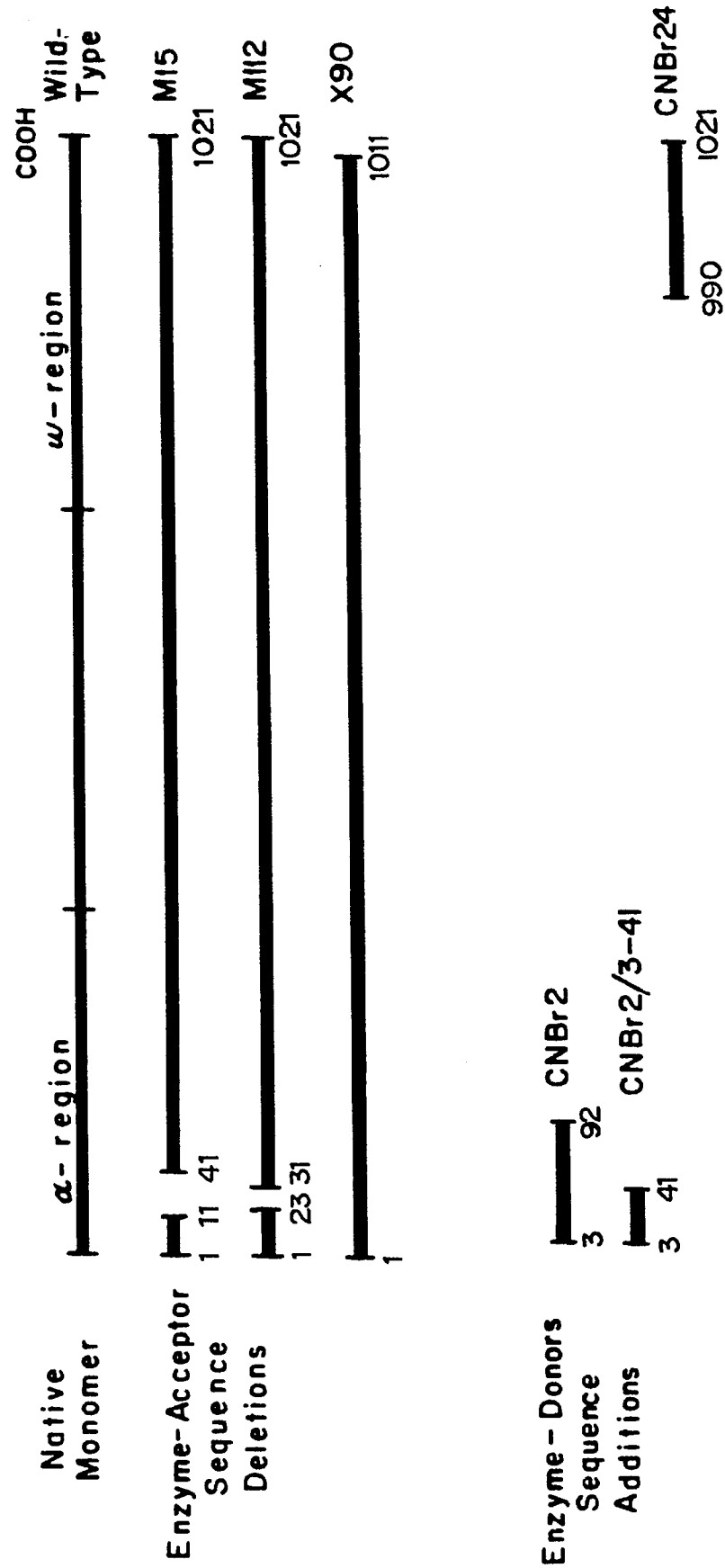
Figure 2A:
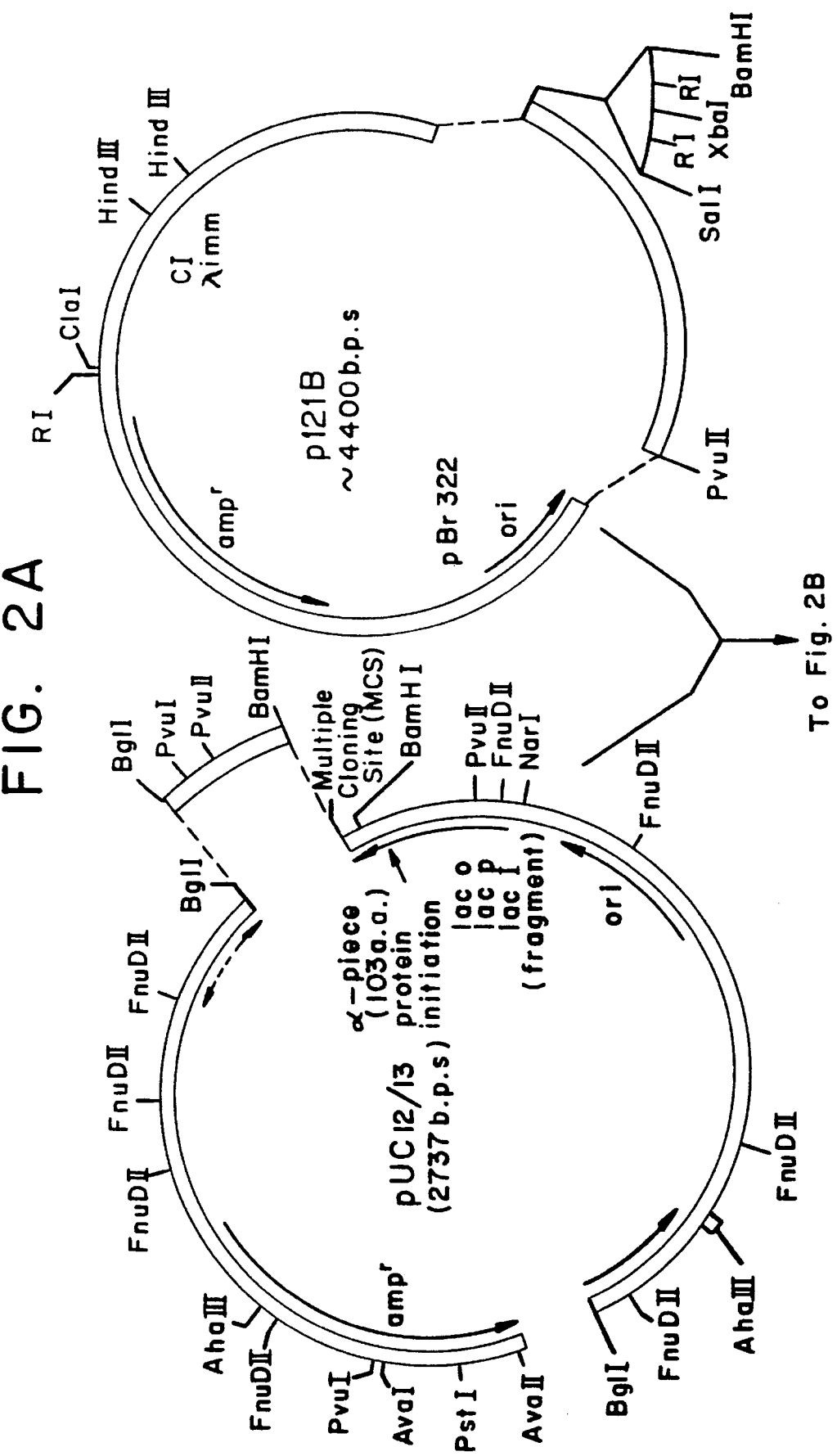
Figure 2B:
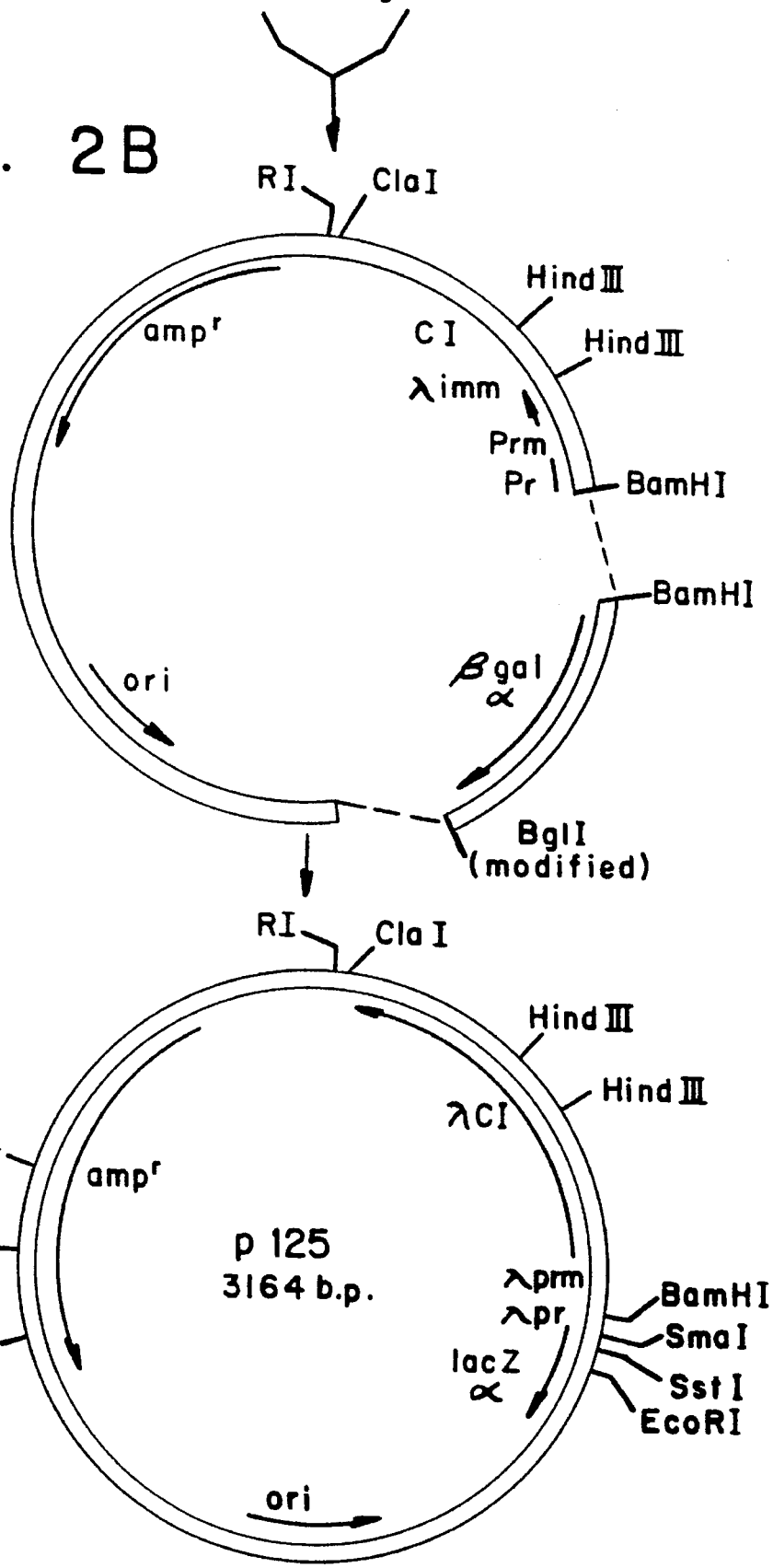
Figure 2C:
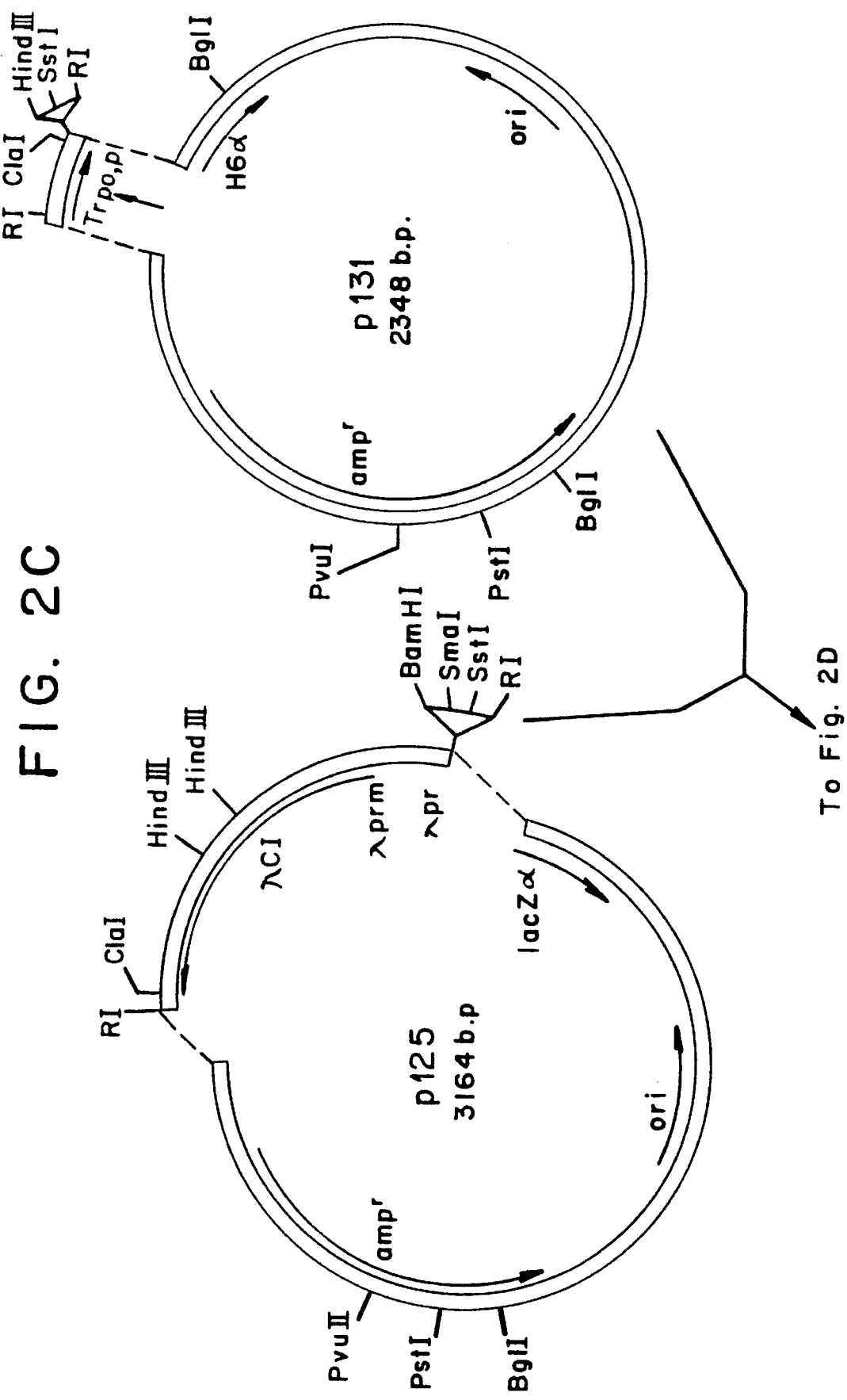
Figure 2D:
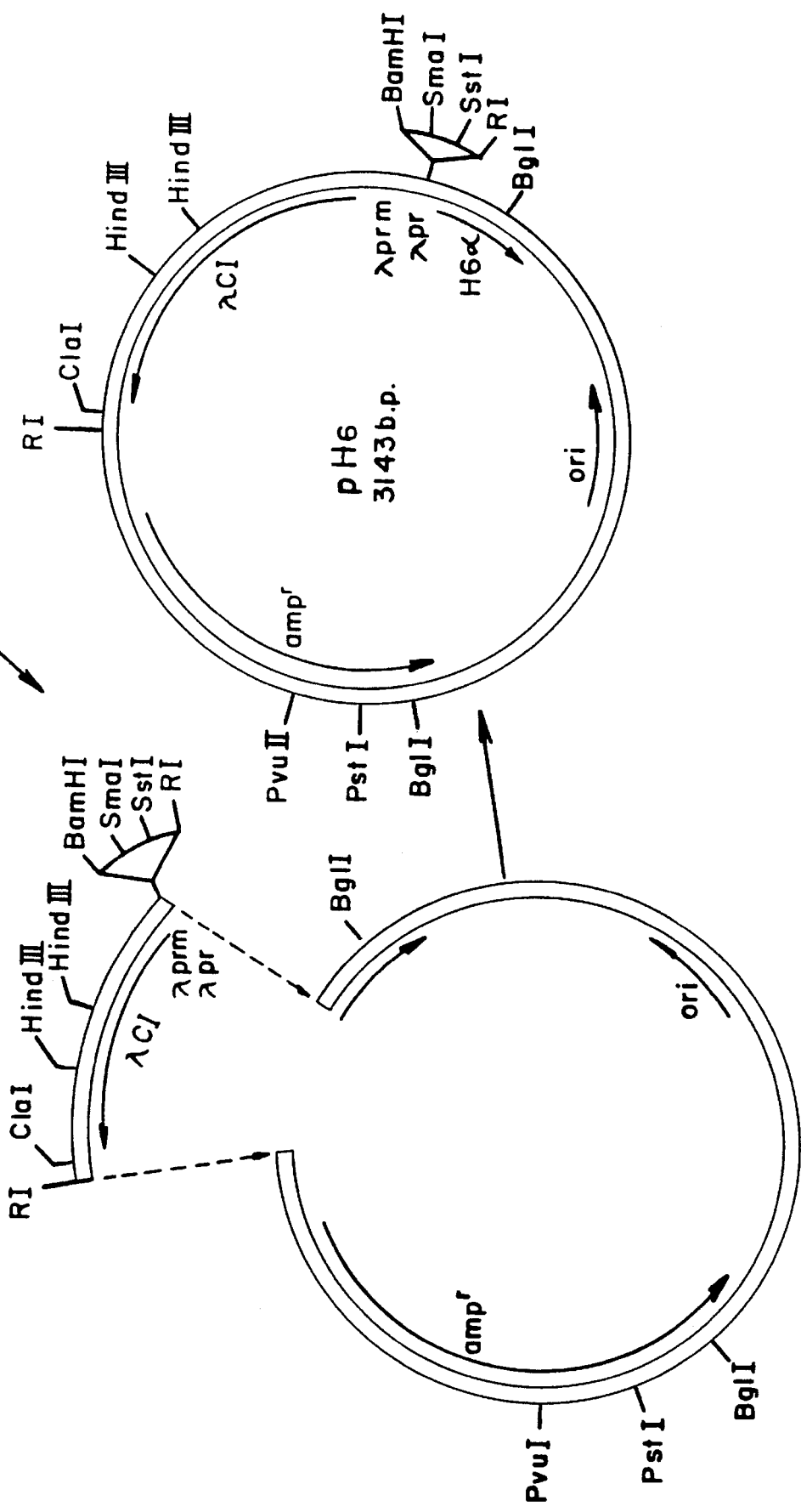

Plasmid pβgal2 is a derivative of plasmid pCVQ2 (Queen, 1983, J. Molec. Applied Genetics 2:1) which carries the lac operon under regulatory control of the temperature inducible λPr promotor. To make the λ regulatory sequences available for other genetic constructions the plasmid pβgal2 was modified. Plasmid pβgal2 was digested with BamHI and SalI and the DNA sequences encoding the lac operon were removed. The DNA fragment containing pBR322 sequences (including amp$^r$ and ori) and λCI were isolated by agarose gel electrophoresis. Synthetic DNA linkers containing recognition sequences for BamHI, EcoRI, HindIII, SalI and XbaI were ligated and then cleaved with BamHI and SalI to create shorter multi-linker segments with BamHI and SalI cohesive ends. These DNA fragments were ligated to the BamHI/SalI fragment isolated from pβgal2. The resultant plasmid, p121B contains EcoRI and XbaI recognition sites between the BamHI and SalI of the vector. Plasmid p121B was digested with BamHI and PvuII. The BamHI/PvuII DNA fragment containing the β-lactamase gene (which confers resistance to ampicillin, amp$^r$), the phage λCI gene (a temperature controlled repressor) and the plasmid origin of replication (ori) was purified by agarose gel electrophoresis. The BglI(–)/BamHI DNA fragment from pUC13 and the BamHI/PvuII DNA fragment from p121B were ligated using T4 DNA ligase as shown in FIG. 2A. The recombinant plasmid was transformed into 10 JM83, an *E. coli* bacterial host for growth of the single-stranded phage M13 and its recombinants which encodes the β-galactosidase mutant polypeptide M15 (Messing, 1979, Recombinant DNA Technical Bulletin, NIH Publication No. 79–99, 2, No. 2:43–48) and plasmid p125 was selected. In vivo complementation occurred at 42° C. but not at 32° C. demonstrating that plasmid p125 produces a temperature inducible β-galactosidase α-protein.

6.1.2 H, B, M and P Series Enzyme-Donors

In one series of experiments, to obtain enzyme-donor peptides of the type containing an analyte-coupling domain, (see Section 5.1.1.) various sized α-regions were isolated from pUC13 (Vieira and Messing, 1982, Gene 19:259–268; Messing, 1983, Methods in Enzymology 101:20–78; Bethesda Research Laboratories, Gaithersburg, Md.) digested with HaeII, BglI, MstI or PvuI yielding H-series, B-series, M-series and P-series respectively. The B-, P- and H-series were treated with T4 DNA polymerase and S1 nuclease. The M-series were not treated. Each series of DNA was digested with SacI which is located in the multiple cloning site, and the small DNAs encoding an α-complementing peptide were purified by agarose gel purification, electrophoresed onto DEAE-cellulose paper (Schleicher and Schuell, Keene, N.H.), eluted and ethanol precipitated as described by the manufacturer.

Plasmid p141 which carries an *E. coli* trp promotor (EcoRI-SStI, 120 bp) cloned in the 2.3 kb EcoRI-PvuII fragment of pBR322, was digested with NdeI and treated with DNA polymerase Klenow fragment and dATP and dTTP (PL Biochemicals, Milwaukee, Wis.). The resultant DNA was digested with SacI and used as a vector to receive the M, B, H and P series of DNAs. Following treatment with T4 DNA ligase, the DNAs were transformed into *E. coli* strain E9001 (Δlac pro, thi, SupE, F' proAB, lacI$^Q$, Z M15 also referred to as strain 71.18; Messing et al., 1977, Proc. Natl. Acad. Sci. USA 75; 3642–3646). The DNA constructions were sequenced by the methods of Maxam and Gilbert (1980, Methods in Enzymology 67:499) and are shown in FIG. 4. Also illustrated (*) are the sites for covalent attachment of an analyte.

The resultant strains encoding α-regions under Trp control in *E. coli* strain E9001 were for series B, strain MG130 carrying plasmid p130; for series M, strain MG129 carrying plasmid p129; and for series H, strain MG131 carrying plasmid p131.

To improve expression levels of the different cloned α-regions, the α-regions were transferred to new plasmids and placed under control of the λPr operator-promotor. For example, to construct MG141, the gene encoding the DNA sequences of H6 from the H-series was placed under Pr control, by replacement of the Trp promotor for the λPr and λCI genes as described below.

Plasmid p131, containing H6 under the Trp operator-promotor control was digested with EcoRI and the larger, approximately 2.1 kb fragment was isolated by agarose gel electrophoresis. The λPr and λCI genes were gel purified from the small fragment of an EcoRI digestion of p125. The 2.1 kb fragment of p131 was ligated to the small fragment from p125 in effect replacing the Trp promotor with the λPr and λCI promotor system. This protocol was also repeated with p130 and p129 to yield the following plasmids and strains under λPr control for series B, strain MG139 carrying plasmid p139; for series M, strain MG140 carrying plasmid p140; and for series H, strain MG141 carrying plasmid pH6. The DNA constructions were sequenced by the methods of Maxam and Gilbert, Methods in Enzymology 67:499 (1980), and are shown in FIG. 4.

6.1.3 p148 Enzyme-Donor

Utilizing the λPr sequence from p125, a new plasmid was constructed to provide a cysteine residue towards the N-terminal end of the peptide. This new plasmid, p148, also contained three cysteine residues located near the C-terminal end of the peptide. Plasmid p125 was digested with BamHI and EcoRI, an approximately 1100 bp fragment was cleaved from the vector and purified by agarose gel electrophoresis. This fragment, contains the λPr sequence which was ligated into the unique BamHI/EcoRI restriction sites of pUC12, (Messing, 1983, Methods in Enzymology 101:20–78). This recombinant plasmid was transformed into JM83 cells and found to complement in vivo at 42° C. in a manner analogous to the construction of-p125 described supra. The structure of the enzyme-donor p148 is also shown in FIG. 4, including the positions of amino and sulfhydryl group coupling sites which are utilized according to the present invention for the attachment of analyte.

6.1.4 Enzyme-Donor 3

Enzyme-donor 3 (ED3) was constructed from enzyme-donor 1 (ED1) which was constructed from H6. ED1 was constructed as follows:

Synthesis of DNA fragments was performed on an Applied Biosystems, Inc. (ABI, Foster City, Calif.) Model 380A DNA Synthesizer. Each sequence was entered into the program memory and the machine automatically manufactured the desired single strand of DNA, cleaved each fragment from the controlled pore glass support, and collected the DNA in a vial. DNA samples were treated with 1.5 ml of concentrated $NH_4OH$ for 6–24 hours at 55° C., and taken to dryness in a Savant Speed Vac Concentrator.

The dried pellet of each DNA fragment was dissolved in a small quantity of formamide (100–200 μl) and purified on a 12% acrylamide gel (BRL Model SO, 34–40 cm, 1.6 mm thickness) and was electrophoresed overnight at 200 volts. The desired band was visualized using Baker-flex silica gel 1B-F (J. T. Baker Chemical Co.) as a fluorescent background. The desired DNA band was cut out of the gel with a razor blade and the DNA electrophoresed from the acrylamide gel fragment in an International Biotechnologies, Inc. (IBI) Model UEA unit following the manufacturer's instructions. The DNA was collected in a small volume of buffer and ethanol precipitated. The fragments were treated with T4 polynucleotide kinase according to the manufacturer's instructions. Complementary DNA strands were combined, heated to 90° C. for 2 minutes, and slowly cooled to room temperature. The annealed DNAs were purified by agarose gel eclectrophoresis to remove unhybridized strands and used in ligation reactions.

Figure 11:
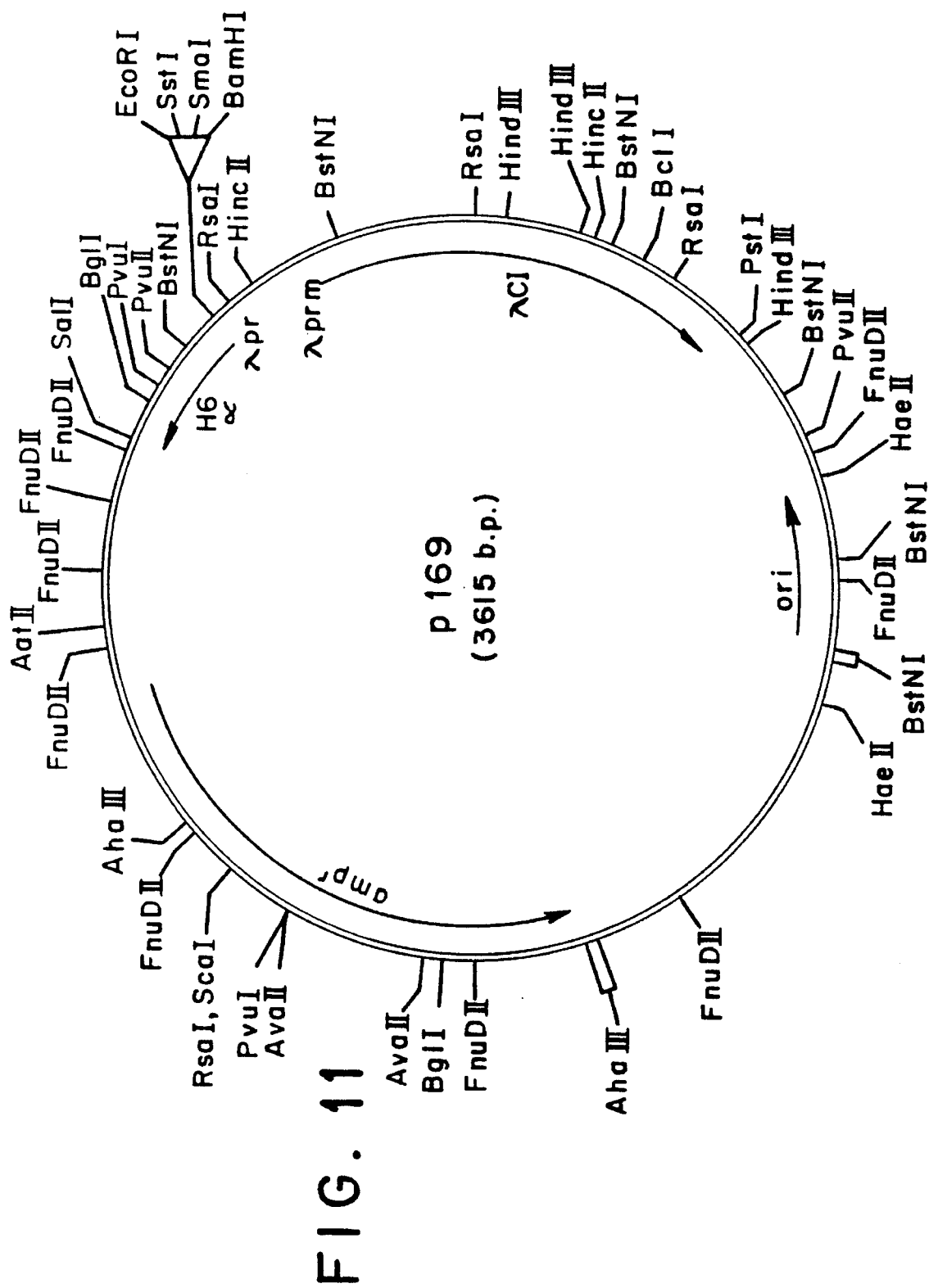

The starting plasmid was p169 which contains the H6 gene under λPr control inserted between restriction sites BamHI and SalI (see FIG. 11). The change from H6 to ED1 involved changing both the N-terminus and C-terminus of H6 while leaving the α-domain in between intact. Two aliquots of p169 were cut with restriction enzymes. The first aliquot was digested with EcoRI and BglI and the small 150 bp fragment was gel purified. The second aliquot of p169 was digested with BamHI and SalI. This cleaves the plasmid into vector and the α-donor gene region. The vector portion was gel purified.

The new N-terminal coding region of ED1 was a 75 bp DNA fragment synthesized by the Applied biosystem, Inc. machine (see FIG. 12). The new C-terminal coding region, a 50 bp DNA fragment, was also synthesized (see FIG. 12). The two (2) new DNA fragments were ligated to the small EcoRI-BglI H6 DNA fragment. This mix was cut with BamHI and SalI to yield the new ED gene of about 275 bps. This piece of DNA was gel purified and ligated into the vector BamHI-SalI DNA fragment.

Figure 13:
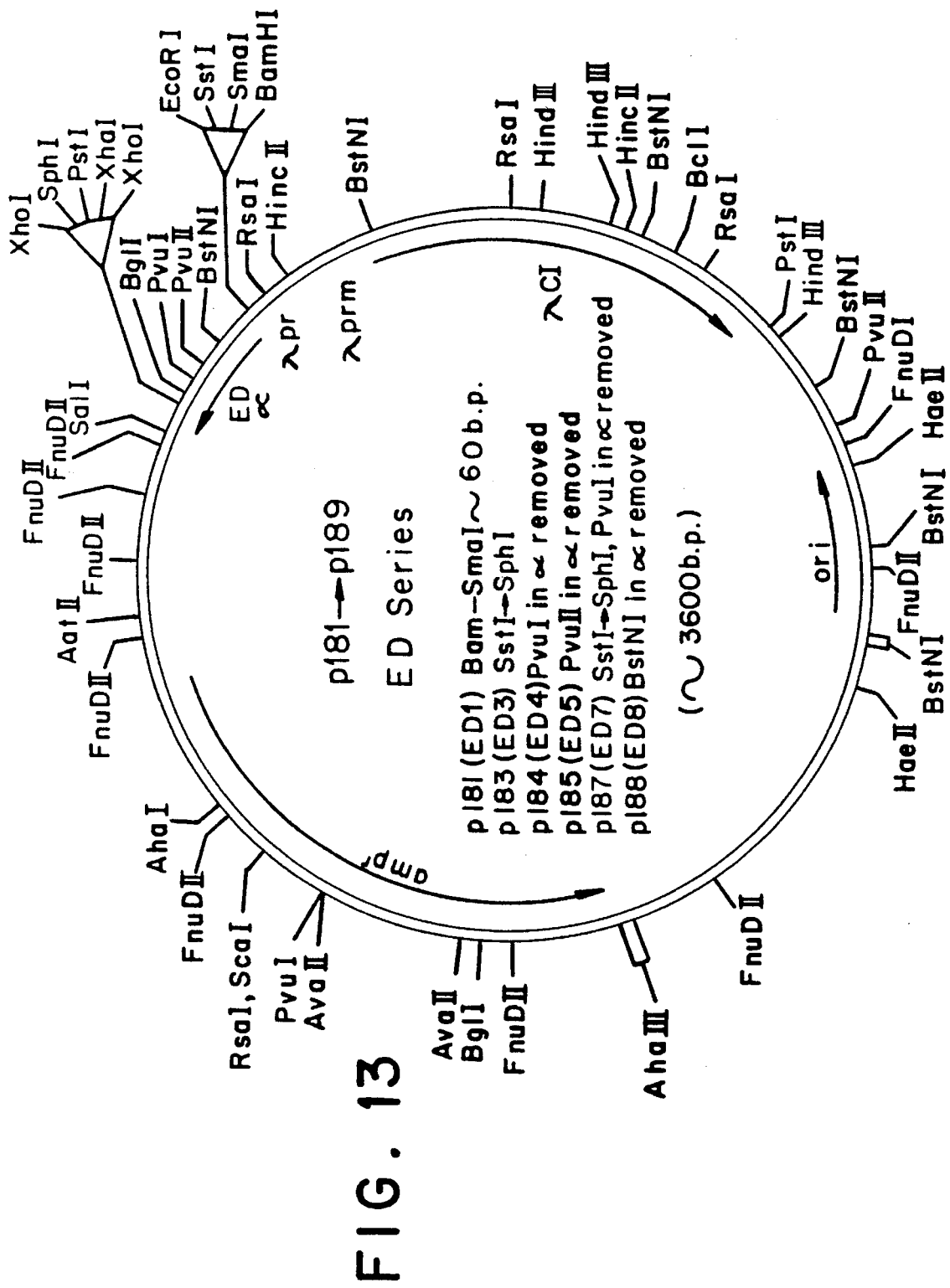
FIG. 13 (not drawn to scale) is a diagrammatic representation of plasmids of the p180 series, indicating various genetic regions and restriction enzyme cleavage sites.

After confirming the ED1 sequence, this plasmid (p181, see FIG. 13) was cut with BamHI and EcoRI which removes the 75 bp ED1 N-terminus. This region was replaced by a newly synthesized fragment of 30 bps (see FIG. 12) substituted into the BamHI-EcoRI space.

Thus, ED3 is 15 amino acids shorter than ED1 and has a cysteine residue near its N-term in us. ED1 has no cysteine or lysine in its sequence. FIG. 14 depicts the amino acid sequence of ED3.

6.1.5 Enzyme-Donor 3A

The amino acid sequence of enzyme-donor 3A (ED3A) is shown in FIG. 14. The peptide is synthesized on a Beckman (Palo Alto, Calif.) 990B Peptide Synthesizer. Methods for synthesis are as described by Stewart and Young (Solid Phase Peptide Synthesis, 176pp, Pierce Chemical Co., Rockford, Ill., 1984). General chemicals are from Aldrich (Milwaukee, Wis.). BOC-amino acids are from Peninsula Laboratories (Belmont, Calif.). Side chain protections are Boc-Thr (OBzl), Boc-Glu (OBzl), Boc-Ser (OBzl), Boc-Asp (OBzl), Cys (MeOBzl), Boc-Asn/HOBT, Boc-Arg (TOS) and Boc-His (TOS). Aminomethylpolystyrene solid phase resin beads from Bio-Rad Laboratories (Richmond, Calif.) are esterified to p-hydroxymethylphenyl acetic acid Boc-Thr (OBzl) with dicyclohexyl carbodiimide as described by Stewart and Young (1984). The synthesis scale used is 1 mmole Boc-Thr attached to the solid phase resin and 3 mmoles of each Boc amino acid. The synthesizer is then programmed to carry out the synthesis. The resultant peptide is cleaved from the resin with anhydrous hydrofluoric acid and extracted with acetic acid. Following hydrogenation, the peptide is purified by preparative reverse phase HPLC using a Waters phenyl column with a 0–80% acetonitrile gradient in water containing 0.1% TFA and 0.1% ethane thio. The partially purified peptide is dialyzed exhaustively into 1 mM $NH_4HCO_3$, 1 mM 2-mercaptoethanol and lyophilyzed. Amino acid analysis of the peptide is shown in Table I.

TABLE I

| AMINO ACID ANALYSIS OF ED3A | | |
|---|---|---|
| AMINO ACID | THEORETICAL | FOUND |
| ASP | 5 | 4.25 |
| THR | 3 | 2.13 |
| SER | 3 | 2.39 |
| GLU | 5 | 5.22 |
| PRO | 3 | 3.33 |
| GLY | 1 | 0.87 |
| ALA | 5 | 5.65 |
| CYS—PE | 1 | 1.10 |
| VAL | 3 | 2.27 |
| MET | 0 | 0 |
| ILE | 1 | 0.48 |
| LEU | 4 | 3.12 |
| TYR | 0 | 0 |
| PHE | 1 | 1.16 |
| HIS | 1 | 1.11 |
| TRP | 2 | 1.61 |
| LYS | 0 | 0 |
| ARG | 5 | 5.00 |

The molecular weight equals 4942.53 with the average molecular weight of an amino acid being 114.943.

In summary, the polypeptides shown in FIG. 4 provide convenient coupling side chains at varying distances from the required α-complementing sequence. The DNA sequences encoding the peptides made by recombinant methods were determined by standard Maxam and Gilbert techniques, confirming the predicted structures. The amino acid composition of H6 was confirmed by amino acid analysis.

6.1.6. ED Enzyme-Donor Series

A series of enzyme-donors called the ED series was constructed by recombinant DNA techniques. ED3 has already been described in Section 6.1.4. Other members of the series include ED4, ED5, ED7, ED8, ED13, ED15 and ED17. The amino acid sequences of the ED series of enzyme-donors appears in FIG. 15, A–I.

The gene coding for ED4 was constructed by first synthesizing a DNA fragment on an Applied Biosystems, Inc. Model 380A DNA Synthesizer (as described in Section 6.1.4.) of the following sequence:

```
         *                    50
      TGC CCT TCC CAA CAG TTG CGC AGC CTG AAT
      TA ACG GGA AGG GTT GTC AAC GCG TCG GAC TTA
     Pvu I

60
     GGC CTC GAG TCT AGA TCT GCA GGC ATG    (57 mer)
     CCG GAG CTC AGA TCT AGA CGT CC         (55 mer)
                                      Sph I
```

The "T" marked with an asterisk represents a change from a "C". This fragment was ligated to the BamHI-PvuI piece from plasmid p181 (ED1) (see FIG. 13). The resultant piece was ligated back into the vector (from ED1-p181) having removed the BamHI-SphI region. The C to T change creates a cysteine (cys) residue and destroys the PvuI site after ligation. (The sticky ends remain the same for ligation).

The gene coding for ED5 was constructed by first synthesizing a DNA fragment of the folowing sequence:

```
      *           **      40              45
     T TGG CGT AAT  TGC GAA GAG GCC CGC ACC GAT  (31 mer)
     A ACC GCA TTA  ACG CTT CTC CGG GCG TGG C    (29 mer)
     Pvu                                  Pvu I
```

The "T" marked with an asterisk represents a change from a "C". The "T" marked with a double asterisk represents a change from an "A". The C to T change destroys the PvuII site. The A to T change changes a serine residue to cysteine residue. This fragment was ligated to the BamHI-PvuII piece and PvuI-SalI pieces from plasmid p182 (ED2 or M15) DNA. (See FIG. 13). The ligated material was cut with BamHI and SalI and inserted into p182 with the BamHI-SalI region removed.

The gene coding for ED7 was constructed by cutting p183 (ED3) and p184(ED4) plasmids (see FIG. 13) with both EcoRI and SalI. The vector from p183 was gel purified (effectively removing the EcoRI-SalI (α) region. In contrast, the small EcoRI-SalI (α) region from p184 was gel purified. The p184 EcoRI-SalI region was then inserted and ligated into the p183 EcoRI-SalI vector.

The gene coding for ED8 was made using site specific mutagenesis in M13 mp11 phage DNA. A primer was made (sequence GGT AAC GCA AGG GRT TTC CCA GTC). This primer is complementary to the sense strand of the αregion coding for amino acids 15–22. The desired change was a G to T in codon 20 which changed a Gly to Cys at amino acid 20 in the aregion of the M13 mp11 DNA. This was accomplished by hybridizing the primer to single-stranded M13 mp11 phage DNA and extending the primer using DNA polymerase I "Klenow fragment" and T4 DNA ligase overnight at room temperature. This DNA was treated with S1 nuclease to eliminate non-double-stranded DNA and then transformed into JM103 cells. Phage from this transformation were isolated; the DNA was purified and the primer extension and transformation was repeated a total of 3 times. Each repeat enriched for the desired product. Finally, mini-prepanalysis was performed on M13 RF DNA from individual plaques. The desired base change eliminated the BstNI site. Restriction analysis of mini-prep DNA with BstNI identified candidates. From the double-stranded M13 RF DNA carrying the desired change, a BamHI-BglI piece was cut out and exchanged for a BamHI-BglI piece in the plasmid coding for ED2.

Figure 16:
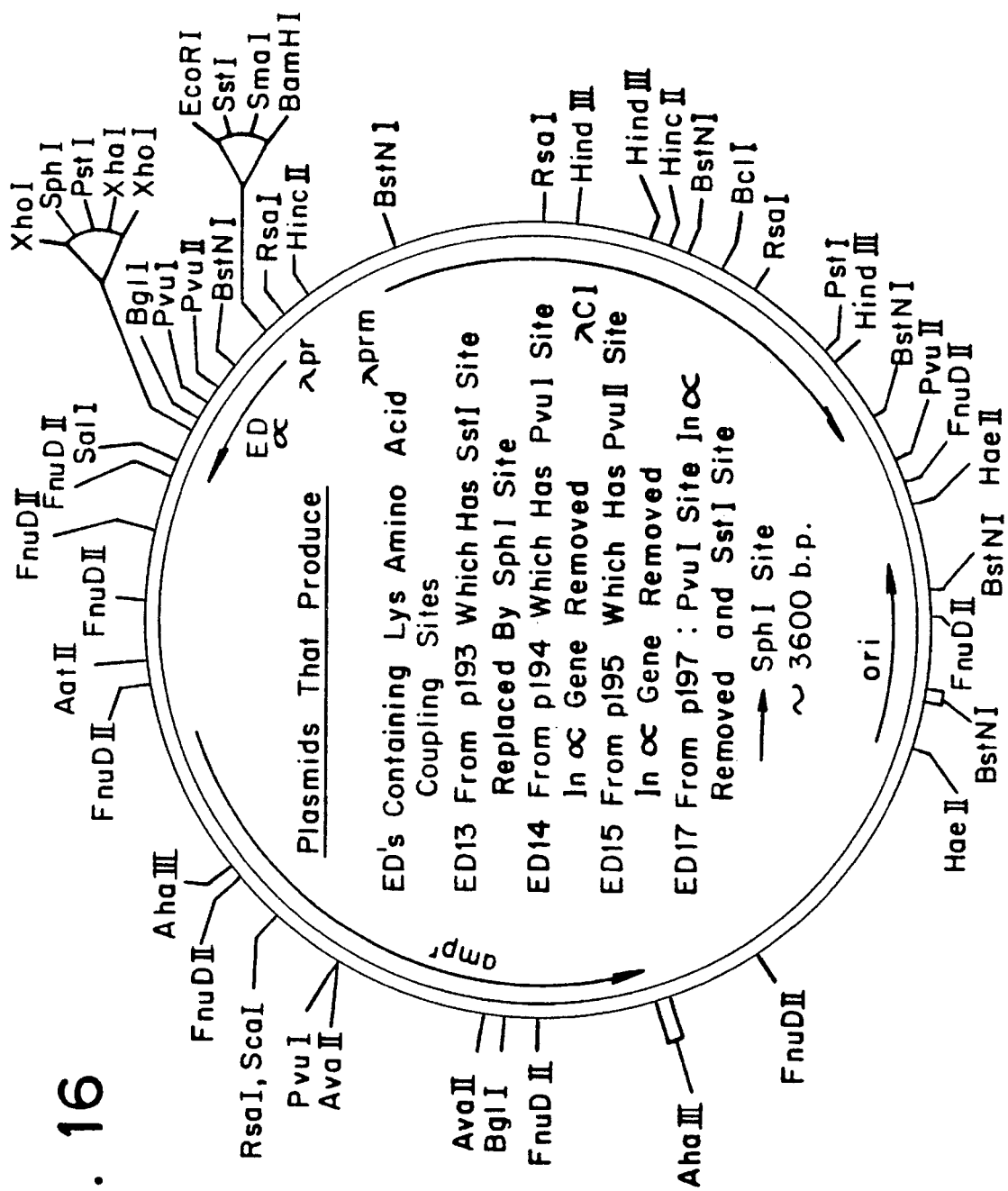
FIG. 16 (not down to scale) is a diagrammatic representation of plasmids of the p190 series, indicating various genetic regions and restriction enzyme cleavage sites.

The gene coding for ED13 (p193, see FIG. 16) was constructed by first synthesizing (as above) a DNA fragment of the following sequence:

```
                                    Lys
     Bam HI   -3              0     change    Eco  RI
     GAT CCC AGC GGC GAT CCC CGG GCA AAA TCG          (30 mer)
         GG TCG CCG CTA GGG GCC CAT TTT AGC TTA A     (30 mer)
```

This synthesized fragment was substituted into p182 (ED2) as described in Section 6.1.4. for constructing ED3.

The gene coding for ED14 (p194, see FIG. 16) was constructed by first synthesizing (as above) a DNA fragment of the following sequence:

```
     Lys
     change              50                    55
     AAA CCT TCC CAA CAG TTG CGC AGC CTG AAT
     TA TTT GGA AGG GTT GTC AAC GCG TCG GAC TTA Pvu I         60
     GGC CTC GAG TCT AGA TCT GCA GGC ATG    (57 mer)
     CCG GAG CTC AGA TCT AGA CGT GC         (55 mer)
                                     Sph I
```

This synthesized fragment was constructed with the same strategy used for ED4, but resulting in a lysine residue instead of a cysteine substitution.

The gene coding for ED15 (p195, see FIG. 16) was constructed by first synthesizing (as above) a DNA fragment of the following sequence:

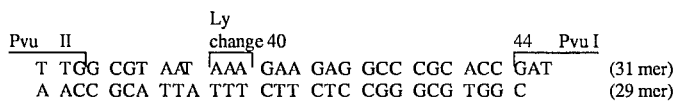

```
    Pvu II         Ly
                   change 40                    44  Pvu I
    T TGG CGT AAT  AAA  GAA GAG GCC CGC ACC GAT     (31 mer)
    A ACC GCA TTA  TTT  CTT CTC CGG GCG TGG C       (29 mer)
```

This fragment was inserted into p182 (ED2 or M15) in the same way used to construct ED5.

The gene coding for ED17 (p197, see FIG. 16) is a combination of the ED 13 and ED14 genes, constructed in the same way that the gene coding for ED7 was.

The following is a listing of the enzyme acceptors which may be used with the ED series of enzyme donors.

| ENZYME DONOR | ENZYME-ACCEPTOR* |
|---|---|
| ED3  | M15,EA1,EA14,EA20,EA22 |
| ED4  | M15,EA1,EA14,EA20,EA22 |
| ED5  | M15,EA1,EA14,EA20,EA22 |
| ED7  | M15,EA1,EA14,EA20,EA22 |
| ED8  | M15,EA1,EA14,EA20,EA22 |
| ED13 | M15,EA1,EA14,EA20,EA22 |
| ED14 | M15,EA1,EA14,EA20,EA22 |
| ED15 | M15,EA1,EA14,EA20,EA22 |
| ED17 | M15,EA1,EA14,EA20,EA22 |

*Other enzyme-acceptors have not been tested.

Of the foregoing enzyme-donor and enzyme-acceptor pairs, the ED5 and EA22 combination is a most preferred pair for use in the complementation assays of this invention.

6.2 Enzyme-Acceptors

In one group of experiments, a series of in-frame sequence deletions of the β-galactosidase gene were constructed to prepare a series of enzyme-acceptors according to methods described supra in Section 6.1. pUC13 was digested with PvuII (yielding a blunt end) and ligated to an 8 bp synthetic DNA linker containing an XhoI restriction site to create a new plasmid, pUC13X.

The α-region containing the XhoI restriction site was then replaced into the entire lacZ gene, which encodes native β-galactosidase without disrupting the remainder of the lacZ gene or the background plasmid. The Z gene contains two BglI sites. The first of these BglI sites is contained within the α-region in pUC13 downstream from the PvuII site where the XhoI linker was inserted. Thus the α-region from pUC13X was removed from the rest of the plasmid by digesting with BamHI and BglI and the 170 bp fragments designated B1X.

The remainder of the lacZ gene which encodes β-galactosidase was obtained from the plasmid pβga12 (Queen, 1983, J. Mol. Appl. Genet. 2:1). This plasmid was digested with BglI and EcoRI and two DNA fragments representing 93% of the Z gene were isolated. The termini of each fragment was different from any other termini used in this construction. The isolated fragments were 2115 bp (hereinafter referred to as B2) and the 737 bp (hereinafter referred to as B3). The EcoRI restriction site in the Z gene is near the C-terminal end of the gene. This terminus must be present when the Z gene containing an XhoI site is constructed.

The mutant Z gene was inserted in pF29. Plasmid pF29 contains a Z gene α-region fused to the C-terminal end of the Z gene at the EcoRI site. This α-region is controlled by the λPr promotor inserted at a BamHI site. To construct pF29 two intermediate plasmids, pF15 and pF16 were constructed. pβga12 was digested with AvaI and the cohesive 3' end filled in using the Klenow fragment and the four dNTPs to create blunt ends. A SalI linker (GGTCGACC) (New England BioLabs, Beverly, Mass.) was ligated to the linearized plasmid using T4 DNA ligase. The resultant DNA was digested with EcoRI and SalI, and a 300 bp DNA fragment representing the omega (ω) end of the β-galactosidase Z-gene purified by agarose gel electrophoresis. This ω-region was fused to an α-region under control of λPr as follows. pUC12 DNA (Bethesda Research Laboratories, Gaithersburg, Md.) was digested with BglI and blunt ends created by treatment with Klenow fragment and the four dNTPs. EcoRI linkers (GGAATTCC) (New England BioLabs, Beverly, Mass.) were ligated to the blunt ends with T4 DNA ligase. The DNA was digested with BamHI and EcoRI and a 180 bp fragment representing the α-region of the Z-gene was purified by agarose gel electrophoresis. The vector used to accept the α- and ω-gene fragments was pβga12 digested with BamHI and SalI and purified by agarose gel electrophoresis to remove the lac operon sequences. The vector, α-gene and ω-gene fragments were ligated together using T4 DNA ligase. The unique ends of the DNA fragments direct the order in which these fragments were cloned. The product plasmid was designated pF15.

pF15 was further modified by converting the unique PvuII site into the vector SalI site using SalI linkers ligated to the blunt ends created by digesting pF15 with PvuII. This modified pF15 was then digested with BamHI and SalI, and the largest DNA fragment was purified by agarose gel electrophoresis which removes the α-ωgene sequence and a DNA fragment located between the SalI site and the PvuII site. Unmodified pF15 was also digested with BamHI and SalI and the α-ωfragment purified. When the large fragment from the modified pF15 was ligated to the α-ωfragment, the plasmid pF16 was generated.

pF16 is about 1350 base pairs smaller than pF15 and has the effect of moving a unique NdeI site much closer to the SalI site. This maneuver eliminates the unnecessary DNA sequences from being carried through subsequent contructions.

To construct pF29, pF16 was digested with ClaI and NdeI and the 1400 bp DNA fragment encoding the λCI, λPr, and the α- and ω-regions of β-galactosidase was purified by agarose gel electrophoresis. pUC13 was digested with AccI and NdeI and the vector was purified by agarose gel electrophoresis. Since the AccI and ClaI restriction sites have identical cohesive ends and the NdeI restriction sites share identical termini, ligation of the DNA insert from pF16 and the pUC13 vector can occur only in one orientation. Ligation with T4 DNA ligase yielded pF29. pF29 contains one EcoRI site and no ClaI sites which was desirable since a second EcoRI and the ClaI site would have interfered with the construction of modified plasmids (e.g., p149 and subsequent analysis of the deletion routants created from p150 described below).

pF29 was digested with BamHI and EcoRI, the intervening α-donor was removed and this vector was filled-in using B1X plus B2, plus B3 (B1X+B2+B3). The unique single-stranded end of each piece defines the order in which the pieces can be ligated together. The B1X, B2 and B3 were ligated into the pF29 vector digested with BamHI and EcoRI described above, thus reconstructing a Z gene with an XhoI linker at bp 102 encoding amino acid 34 under λPr control. The resultant plasmid was designated p149.

Figure 5B:
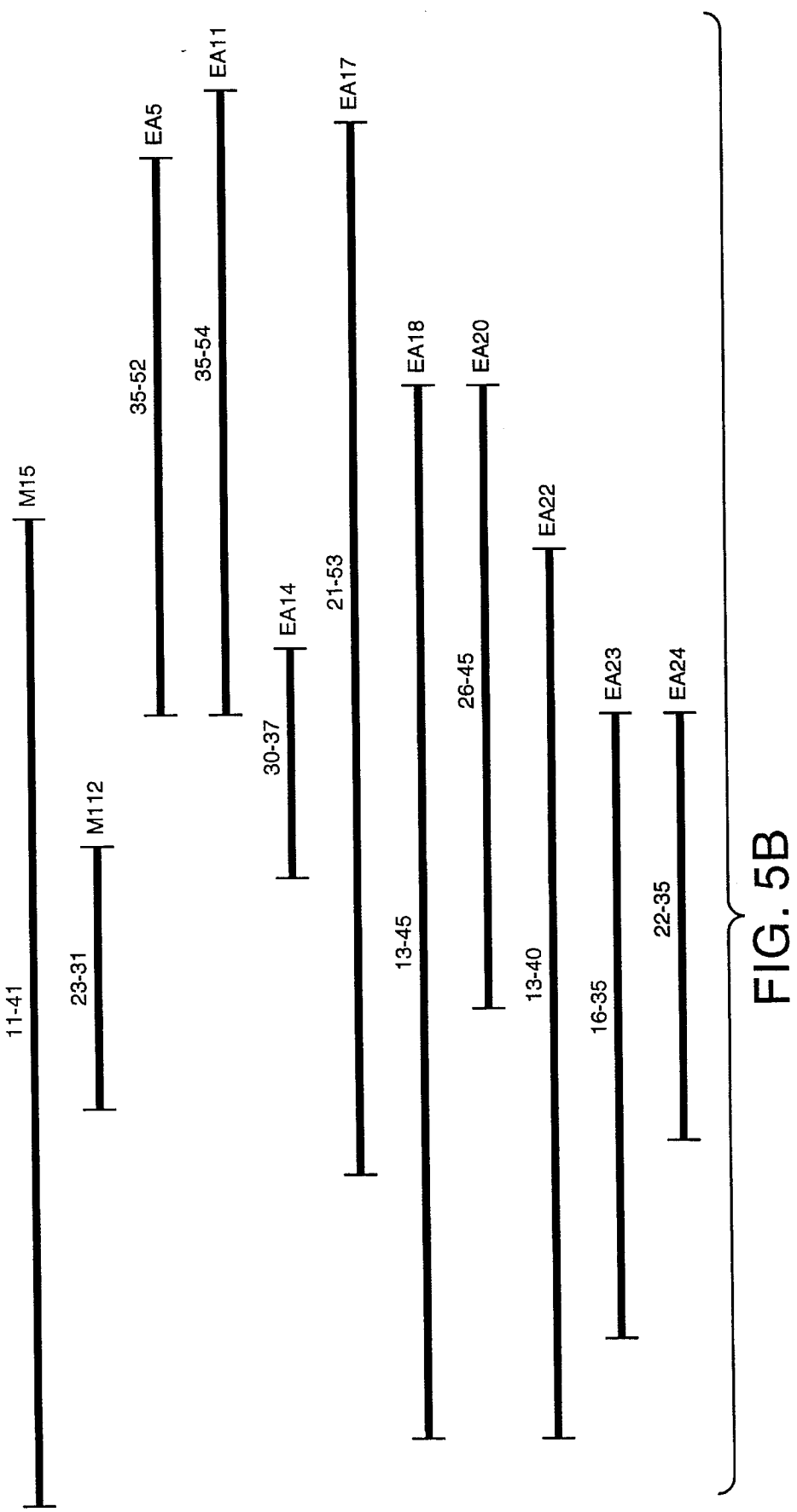

To create a method for screening for the creation of viable enzyme-acceptors following digesting with XhoI and Bal 31 digestion, a separate α-donor without the XhoI site was inserted into p149. An FnuDII digestion fragment from pUC13 containing the lacz operator, promotor and α-donor was inserted into the SalI site of p149 which had been filled in with Klenow fragment. The resultant plasmid was designated p150. Deletions were created by digesting p150 with XhoI and then digesting the DNA with Bal 31 exonuclease. After Bal 31 treatment, the plasmid was ligated with T4 DNA ligase and transformed into AMA1004 host cells (AMA1004 is galU, galK, strA$^r$, hsdR$^-$, leuB6, trpC 9830, Δ(lacIPOZ) C29, (Casadaban et al., 1983, Methods in Enzymology, 100:293), and screened on luria-Bertani plates containing the inducer isopropylthiogalactoside (IPTG) and the chromogenic substrate 5-bromo-4-chloro-3-indolyl-β-D-galactopyranoside (Xgal, Sigma Chemical Co., St. Louis, Mo.). Colonies that were white at 30° C. but blue at 42° C. indicated creation of viable enzyme-acceptors. Colonies were selected and plasmid DNAs prepared. Plasmid DNAs were digested with SalI, to remove the α-donor, religated and transformed into AMA1004 host cells. The sequence deletions were confirmed by Maxam and Gilbert sequencing and the enzyme-acceptor proteins purified as described in Section 7.1. The resultant strains are shown in FIG. 5.

Enzyme-acceptors have been constructed utilizing DNA synthesis techniques. For example, enzyme-acceptor 1 (EA1) was constructed from p149 except that the α-region which contains the XhoI linker was replaced with the following synthesized DNA fragments (5'→3'):
(1) CAA CAG TTG CGC AGC CTG AA
(2) AGG CTG CGC AAC TGT TGG GAA GGG CGA TCG
(3) ACC CAA CTT AAT ACC GAT CGC CCT TCC
(4) GTA TAA AGT TGG GTA ACG CCA GGG CCT TCC CA
(5) CAA CGT CGT GAC TGG GAA GGC CCT GGC GTT
(6) GTC ACG ACG TTG TAA AAC GAC GGC CAG TGA ATT CGA GCT CGC CCG GG
(7) GAT CCC CGG GCG AGC TCG AAT TCA CTG GCC GTC GTT TTA These fragments encode an in-frame deletion of amino acids 26–43 of the lac Z gene and carry BamHI and BglI sticky ends. These fragments were annealed, purified by gel electrophoresis, treated with BamHI and ligated to B2 plus B3 and the pF29 vector. A positive colony was selected and confirmed by DNA sequence analysis.

6.2.1 Comparison of Complementation Efficiency

In order to assess complementation efficiency of the enzyme-acceptors prepared as described in Section 6.2, representative enzyme-acceptor preparations were compared using H6 as the enzyme-donor.

A microtiter plate format was used comprising a total volume of 200 μl of PM2 buffer (0.5M Na$_2$HPO$_4$, pH 7.0, 1 mM MgSO$_4$, 0.18 mM MnSO$_4$, 1 mM EDTA, 0.02% NAN$_3$, 0.05% Tween 20) containing 2.5×10$^{-8}$M of the apppropriate enzyme-acceptor preparation and 1.25 mg/ml O-nitrophenol-β-D-galactopyranoside substrate. A series of dilutions of H6 (1:20; 1:40; 1:80) were added to initiate complementation. The optical density (414 nm) was measured at 30 and 45 minutes incubation at 37° C. The results are illustrated in Table II.

TABLE II

| H6 Dilution | EA23 | EA14 | EA22 | EA24 | EA20 |
|---|---|---|---|---|---|
| A. OD$_{414}$ After 30 Minutes Incubation at 37° C. | | | | | |
| 1/20 | .118 | .736 | .708 | .273 | .526 |
| 1/40 | .062 | .351 | .361 | .142 | .277 |
| 1/80 | .030 | .171 | .174 | .071 | .128 |
| B. OD$_{414}$ After 45 Minutes Incubation at 37° C. | | | | | |
| 1/20 | .299 | 1.585 | 1.402 | .579 | 1.148 |
| 1/40 | .154 | .776 | .715 | .299 | .610 |
| 1/80 | .068 | .365 | .345 | .147 | .294 |

As demonstrated in Table I, the complementation efficiency of the various enzyme-acceptors varied considerably. The relative complementation efficiencies were: EA14=EA22>EA20>EA24>EA23.

7. EXAMPLE: ENZYME IMMUNOASSAY FOR THYROXINE

This example illustrates an immunoassay for thyroxine using an antibody specific for thyroxine as the analyte-binding protein. The enzyme-donor-antigen utilized is ED4 and the enzyme-acceptor is EA22.

7.1 Preparation of Enzyme-Acceptor

The deletion mutant polypeptides of β-galactosidase was prepared by growing the desired enzyme-acceptor strain in TY broth (1 liter contains Bacto tryptone 10 g, yeast extract 5 g, NaCl 5 g and glucose 1 g, pH 7.5). Cells were grown at 42° C. Cells were harvested by centrifugation, washed with breaking buffer (BB) (0.2M Tris®-HCl pH 7.6, 0.2M NaCl, 0.01M Mg acetate, 0.01M 2-mercaptoethanol, 5% glycerol) then pelleted by centrifugation and frozen.

Cell pellets (15 g) were suspended in 40 ml BB. Lysozyme (Sigma Chemical St. Louis, Mo.) was added to a final concentration of 0.20 mg/ml and the suspension incubated on ice for 30 minutes. Following incubation, the suspension was frozen in a −70° C. alcohol bath and quickly thawed in a 37° C. water bath. Care was taken to maintain the temperature of the thawing suspension below 4° C. The viscosity of the lysate was reduced by sonic treatment with a Virsonic cell disruptor (Model 16-850, Virtis Co., Gardiner, N.Y.). Phenylmethylsulfonyl fluoride (PMSF, Sigma Chemical) was added to a final concentration of 0.1 mM, and insoluble material was removed by centrifugation (16,000× g, 30 minutes). One-tenth volume of a 30% streptomycin sulfate solution was slowly added to the supernatant. After 15 minutes on ice the precipitated nucleic acids were removed by centrifugation at 16,000×g for 20 minutes. The cleared lysate was brought to 40% saturation with (NH$_4$)$_2$SO$_4$ by slowly adding an equal volume of an 80% saturated solution. Following a 2-hour period of stirring at 4° C., precipitated material was collected by centrifugation at 16,000×g for 30 minutes.

The pellet was redissolved in BB and dialyzed against 1000 volumes of 0.1M NaH$_2$PO$_4$, pH 7.2, 50 mM NaCl, 1 mM MgSO$_4$, 10 mM 2-mercaptoethanol in water, with one change after 6 hours. The dialyzed enzyme-acceptor extract was applied to a 2.5×6cm column of p-aminophenyl-1-thio-β-D-galactopyranoside covalently attached to agarose in the same buffer. The column was washed, first with 0.1M $NaPO_4$, pH 7.2, 50 mM NaCl, 10 mM 2-mercaptoethanol, then with 0.1M $NaPO_4$, pH 7.2, 50 mM NaCl, 10 mM 2-mercaptoethanol, and finally with 0.1M $NaPO_4$, pH 7.2, 50 mM Na borate pH 9.0, 10 mM 2-mercaptoethanol into an equal volume of 2.5M Tris®-HCl pH 7.0. All column operations were performed at 4° C.

The eluted enzyme-acceptor was immediately dialyzed extensively against 0.1M $NaH_2PO_4$ pH 7.2, 70 mM NaCl, 1 mM MgSO ($MgSO_4$) and 10 mM 2-mercaptoethanol. After dialysis glycerol was added to 10% and the extract stored at −20° C. These preparations yielded a single band in the Laemmli discontinuous polyacrylamide gel system (Laemmli, 1970, Nature 227:690).

7.2 Preparation of Enzyme-Donors

The various enzyme-donor polypeptides described previously could not be purified from host cells directly. For example, the levels of these peptides found in *E. coli* strain AMA1004 were insignificant. In contrast when the plasmids coding for the complementing peptides were transferred to strain E9001 (Δlac-pro, thi, surE, F' proAB, $lacI^Q$, Z M15 also referred to as 71.18; Messing et al., 1977, Pro. Natl. Acad. Sci. USA 75:3642–3646). Active β-galactosidase was formed by in vivo complementation. β-galactosidase was purified and the complementing peptides recovered by denaturation of the enzyme complex with 6M urea.

Cells were grown in Luria Bertani media supplemented with 0.1% glucose, 50 μg/ml ampicillin, and 0.3 mM IPTG, at 42° C. for 16 hours. Cells were harvested by centrifugation. All the following steps were carried out at 4° C. unless otherwise noted.

Approximately 40 g of cells from a total culture volume of 12 L were resuspended in 80 ml buffer A (50 mM Tris®, pH 7.5, 50 mM NaCl, 10 mM $MgCl_2$, 10 mM 2-mercaptoethanol). Lysozyme (Sigma Chemical, St. Louis, Mo.) was added to a final concentration of 0.20 mg/ml and the suspension was frozen in a −70° C. alcohol bath and quickly thawed in a 37° C. water bath. Care was taken to maintain the temperature of the thawing suspension below 4° C. The viscosity of the lysate was reduced by sonic treatment with a Virsonic cell disruptor (Model 16-850). Phenylmethylsulfonyl fluoride (PMSF, Sigma Chemical) was added to a final concentration of 0.1 mM, and insoluble material was removed by centrifugation at 16,000×g for 30 minutes. One-tenth volume of a 30% streptomycin sulfate solution was slowly added to the supernatant. After 15 minutes on ice the precipitated nucleic acids were removed by centrifugation at 16,000×g for 20 minutes. The cleared lysate was brought to 40% saturation with $(NH_4)_2SO_4$ by slowly adding an equal volume of a 80% saturated solution. Following a 2-hour period of stirring at 4° C., precipitated material was collected by centrifugation at 16,000×g for 30 minutes. The pellet was dissolved in a minimal volume of buffer B (40 mM Tris®, pH 7.5, 0.1M NaCl, 10 mM $MgCl_2$, 10 mM 2-mercaptoethanol) and dialyzed overnight against 200 volumes of the same buffer.

The dialyzed solution was loaded on a 2.5×20 cm column packed with 30 ml of DEAE-cellulose (Whatman DE-52), equilibrated with buffer B. The column was washed with 150 ml of buffer B to remove unabsorbed material. Enzyme was eluted with a linear NaCl gradient: 0.01 to 0.50M NaCl in 40 mM Tris®, pH 7.5, 10 mM $MgCl_2$, 10 mM 2-mercaptoethanol. The volume of each buffer component was 75 ml and the flow rate was 0.50 ml/minute. Fractions were assayed for enzyme activity as described. Peak activity appeared at about 0.3M NaCl. Fractions containing enzyme activity were pooled, and the pool was brought to 40% saturation with $(NH_4)_2SO_4$. After stirring 2 hours precipitated material was collected by centrifugation at 12,000×g for 30 minutes. The pellet was dissolved in a minimal volume of buffer B, then loaded on a 1.0×120 cm column packed with Bio-Gel A-1.5m (bed volume 86 ml, Bio-Rad Laboratories, Richmond, Calif.). The column was developed with buffer B at a rate of 0.10 ml/minute. Fractions were assayed for enzyme activity, and fractions containing peak activity pooled. An equal volume of 100% saturated $(NH_4)_2SO_4$ solution was slowly added. After 2 hours on ice, precipitated material was collected by centrifugation at 12,000×g for 30 minutes.

The pellet was dissolved in a minimal volume of 50 mM $KH_2PO_4$, pH 7.3, 1 mM EDTA. 0.496 g of solid electrophoresis purity urea (Bio-Rad, Richmond, Calif.) per ml of solution was slowly added, bringing the final urea concentration of the pool to 6.0M. The pool was kept on ice until no enzyme activity was visible for five minutes after adding substrate. The denatured enzyme pool was then loaded on a 1.0×120 cm column packed with Sephadex G-75 (bed volume 84 ml, Pharmacia Fine Chemicals, Piscataway, N.J.). The column was developed with 6.0M urea, 50 mM Tris®, pH 7.6, 0.15M NaCl, 1 mM EDTA, at a flow rate of 0.10 ml minute. Fractions were assayed for complementation activity with M15. Fractions containing complementation activity were pooled. The fraction pool was dialyzed 3 times against 4 L of 1 mM $NH_4HCO_3$ and lyophilized.

7.3 Thyoxine Immunoassay

The enzyme-donor conjugate of m-maleimide-benzoyl-L-Thyroxine-H6 was prepared as follows.

L-Thyroxine, free acid (680 mg) was covered with anhydrous methyl alcohol (6.0 ml) and the solution saturated with a vigorous stream of dry hydrogen chloride. After cooling, the saturation procedure was repeated and the solvent removed under reduced pressure. The resultant crystalline precipitate was filtered off, washed with absolute ethyl alcohol, then diethyl ether, and finally dried. The dried Thyroxine methyl ester hydrochloride was dissolved in 50% aqueous ethyl alcohol and the solution treated with 2N sodium hydroxide (one equivalent). A copious white precipitate formed immediately and additional water was added to complete the precipitation. After allowing the precipitated L-Thyroxine methyl ester free base to stand in the cold for one hour, the product was recovered by centrifugation and dried in vacuo. L-Thyroxine methyl ester free base (10 mg) and m-maleimidobenzoyl-N-hydroxysuccinimide ester (MBSE), 5 mg, (Pierce Chemical Co., Rockford, Ill.) were dissolved in 1.0 ml of anhydrous tetrahydrofuran followed by the addition of 10 mg of anhydrous powdered sodium carbonate. The mixture was refluxed for 30 minutes. Examination of the reaction mixture by thin-layer chromatography (TLC) using silica gel G using Siα 250F TLC plates 50×20 cm (Baker, Phillipsburg, N.J.) containing a fluorescent indicator and ethyl acetate as the solvent system showed the reaction to be approximately 70% complete. The product of L-Thyroxine methyl ester free base and MBSE, m-maelimide-benzoyl-L-thyroxine (MBTM) was purified by silica gel column using chloroform:methanol mixtures as eluting solvents. The isolated pale yellow powder of MBTM was approximately 80% pure as assessed by TLC and had an $R_f$ completely distinct from either MBSE or L-Thyroxine methyl ester. The MBTM gave the characteristic orange color for thyroxine upon irradiation with short wave length UV light on silica gel G containing a fluorescent indicator, was ninhydrin negative and the presence of the maleimide group confirmed by its ability to react with cysteines using 5,5'-dithiobis-(2-nitrobenzoic acid) (Sigma Chemical, St. Louis, Mo.).

H6 enzyme-donor polypeptide (10 μg) was dissolved in 0.15 ml of 0.1M sodium phosphate buffer, pH 7.0. To the above stirred solution were added two 5 μl aliquots of m-maleimidibenzoyl-L-Thyroxine methyl ester 0.3 mg in 1.0 ml tetrahydrofuran. After stirring for 1 hour at room temperature the reaction mixture was purified on a Bio-Gel P-2 column (Bio-Rad, Richmond, Calif.) 0.6×16.0 cm, eluting with 0.1M sodium borate buffer, pH 9.0. Ten drop fractions were collected. Aliquots of each fraction were assayed for complementation activity in the presence of the EA23 dimer and O-nitrophenyl-β-D-galactopyranoside. Fractions 10 and 11 contained the highest complementation activity and were pooled.

This example illustrates an immunoasay for thyroxine as analyte using H6-Thyroxine conjugate as enzyme-donor, EA23 as enzyme-acceptor, anti-thyroxine antibody and a series of concentrations of thyroxine.

Reagents for the assay were prepared as follows:

L-Thyroxine standard: 2.6 mg L-thyroxine (Sigma Chemical, St. Louis, Mo.) was dissolved in 200 μl absolute ethanol. Then 800 μl 0.15M NaHCO$_3$ was added and the mixture stored at 25° C. Two fold dilutions of thyroxine were prepared in ethanol: 0.15M NaHCO$_3$ (1:4).

L-Thyroxine antibody: Antisera to thyroxine (T4) was purchased from Western Chemical Research Corp., Denver, Colo. Several lots were tested for titer and an equilibrium constant determined in a radio-immunoassay with IgM Sorb (Enzyme Center, Malden, Mass.). Lots varied with titers of 1:100 to 1:8000. Equilibrium constants varied from 4.5×10$^8$ L/M to 1×10$^{10}$ L/M. Lot #A420, titer 1:8000 (zero binding= 67%) and Keq=2×10$^{10}$ L/M was used.

EA23 acceptor-enzyme: 6.3×10$^{-7}$M in storage buffer. Substrate: O-nitrophenyl-β-D-galactopyranoside (ONPG) was dissolved in 2.5×Z buffer to a final concentration 10 mg/ml solution.

The assay was performed in microtiter plates (Dynatech Cat #001-012-9200 American Scientific Products, Sunnyvale, Calif.) and read on a Titertak Multiscan microtiter plate reader fitted with a 414 nm filter (Flow Laboratories, Rockville, Md.). To each well was added 100 μl of PM2 buffer containing 0.05% Tween 20 (polyoxyethylene sorbitan monolaurate (Sigma Chemical Co., St. Louis, Mo.). To each well was added sequentially 2.5 μl H6-thyroxine conjugate, 2.5 μl of anti-thyroxine antibody, 2.5 μl of the thyroxine standards and 40 μl of EA23. Results are illustrated in Table III.

TABLE III

ENZYME IMMUNOASSAY FOR THYROXINE

| Well | H6-T4[a] (μl) | Antibody (μl) | Thyroxine (μg/μl) | EA2[b] (μl) | OD$_{415}$ |
|---|---|---|---|---|---|
| 1 | — | — | — | 40 | 0.002 |
| 2 | 2.5 | — | — | — | 0.0001 |
| 3 | 2.5 | — | — | 40 | 0.595 |
| 4 | 2.5 | 2.5 | — | 40 | 0.300 |

TABLE III-continued

ENZYME IMMUNOASSAY FOR THYROXINE

| Well | H6-T4[a] (μl) | Antibody (μl) | Thyroxine (μg/μl) | EA2[b] (μl) | OD$_{415}$ |
|---|---|---|---|---|---|
| 5 | 2.5 | 2.5 | 6.25 | 40 | 0.312 |
| 6 | 2.5 | 2.5 | 12.5 | 40 | 0.320 |
| 7 | 2.5 | 2.5 | 25 | 40 | 0.364 |

[a]H6-T4 designates the m-maleimide-benzoyl-L-Thyroxine-H6 conjugate.
[b]EA23 designates the enzyme-acceptor polypeptide (see FIG. 5).

8. EXAMPLE: HEPATITIS B VIRUS SURFACE ANTIGEN ASSAY

This example illustrates an immunoassay for measuring hepatitis B virus surface antigen (HBV-SAg) using N-terminal or C-terminal fusion proteins as enzyme-donors.

8.1 N-Terminal Fusion

Plasmid pBR322 containing the entire genome of HBV inserted in the unique EcoRI site was cleaved with HincII. Fragment B (Sninskey et al., 1979, supra) was cloned into the unique HincII site of pUC13 (Messing, 1983, supra). From this clone a BamHI-AhaIII fragment containing most of the HBV-SAg gene was inserted into pUC13 digested with BamHI and SmaI. This recombinant DNA plasmid 122 was transformed into the JM83 strain of E. coli and light blue colonies, indicating in vivo complementation by a HBV-SAg enzyme-donor, on Xgal plates selected. This clone, MG122, was found to contain HBV-SAg by cross-reaction in the Abbott Auszyme II (1) test (Abbott Laboratories, Chicago, Ill.). This HBV-SAg α-donor fusion can be transferred to another expression vector to yield large quantities of fusion product.

8.2 C-Terminal Fusion

For example, the Hepatitis B Virus surface antigen (HBV-SAg) could be cloned at the carboxy terminus of an enzyme-donor polypeptide. One protocol that could be utilized is briefly outlined below as an illustrative example.

A 1.2 kb FnuDII fragment is isolated from a clone of the entire HBV genome and inserted in pBR322. A PvuI partial digest of p125, treated with S1 nuclease and calf intestinal phosphatase, is then agarose gel purified to isolate full length linear molecules. Following ligation of the FnuDII fragment to the linear DNA of p125, the DNA is transformed into an E. coli (e.g., JM83). Ampicillin resistant colonies, white at 30° C. and blue at 42° C. on Xgal plates, are then selected and screened for production on HBV-SAg (e.g., by the Abbott Auszyme II test). The fusion proteins are then purified by standard ion-exchange and affinity column techniques assaying for complementation.

8.3. Enzyme Immunoassay for HBV-SAg

An immunoassay to measure the presence or quantity pf HBV-SAg in a sample can be prepared by competing unknown HBV-SAg in the sample of interest with an α-HBV-SAg fusion protein for homologous antibody. The amount of free α-HBV-SAg protein available to complement EA23 producing active β-galactosidase will be inversely proportional to the amount of unknown free HBV-SAg measured.

9. EXAMPLE: HEPATITIS B VIRUS CORE ANTIGEN ASSAY

The Hepatitis B virus (HBV) genome DNA was cleaved with restriction enzymes BamHI and EcoRI to produce 2 large DNA fragments. One of these large fragments carries the core gene which encodes the core antigen (HBV-CAg). This fragment was inserted into the multiple cloning site of M13 mp10 RF DNA. After selecting and screening for an M13 phage which carries this HBV insert, a small preparation of phage was purified. Single-stranded DNA which carries the (−) polarity strand (opposite polarity to messenger RNA) of the core gene was isolated from the phage.

Like most genes, the core gene begins with an ATG codon. Since the expression vector in which the core gene was cloned already supplied an ATG codon, it was necessary to obtain a DNA fragment which began at the second core codon. This was accomplished by synthesizing a twelve (12) base pair single strand olingomer which represents the (+) strand (the same polarity as messenger RNA) of codons 2–5 of the core gene (GACATTGACCCT). This oligomer was hybridized to the single-stranded M13 phage DNA and extended in vitro by E. coli DNA polymerase I (Klenow fragment). This preparation was digested with HincII, which cleaved the HBV DNA outside of the core gene 3' to the translation termination codon. Thereafter, nuclease S1 was used to digest the single-stranded DNA 5' to the second codon of the core gene. This leaves a 686 base pair fragment and many smaller double-stranded fragments of various lengths. The 686 base pair fragment was purified by agarose gel electrophoresis. The plasmid expression vector used carried a λPr promotor and ATG start codon next to a BamHI restriction. The vector was digested with BamHI and treated with nuclease S1 to render blunt-ended vector.

The blunt-ended expression vector and the core gene fragment were then ligated together, using T4 DNA ligase, and transformed into competent bacteria. The resultant colonies were screened, and a plasmid identified, carrying the core gene inserted in the proper orientation. Colonies were tested for the presence of core antigen protein in the cell lysate by the Abbott Core Antigen ELISA test (Abbott Laboratories). A strongly immunoreactive positive clone, designated MG152 containing plasmid p152, was selected and the DNA sequence confirmed by Maxam and Gilbert DNA sequencing. Core antigen will be purified and used to reproduce antibody.

Since none of the restriction sites at the amino terminal end of the α-region of pF29 were compatible for fusion of the core gene to the α-region, it was necessary to construct a second plasmid with different restriction sites in the multiple-cloning region at the amino terminal end of the α-gene. pUC13 was digested with EcoRI and the cohesive ends filled-in with DNA polymerase Large Fragment (Klenow fragment) plus all four dNTPs. A PvuII 8 bp (GCAGCTGC) linker DNA was ligated into this site. This modified plasmid was digested with BamHI and PvuII and the N-terminus of the α-piece with the addition of the PvuII linker in the multiple-cloning site isolated. pF29 plasmid DNA was also digested with BamHI and PvuI and the pF29 α-region was removed and replaced with α-region containing the new sequence in the multiple-cloning region of the N-terminus of the α-region. This new plasmid was designated p154.

To construct a core-α fusion protein, the core gene from p152 under λPr control was inserted into the multiple-cloning site of the α-gene of p154. p154 DNA was digested with restriction enzymes BclI and AvaI. The intervening DNA fragment created by this cleavage carries most of the λCI gene and the λPr promotor plus the core gene but without the four 3'-terminal codons of the core gene. This DNA fragment was purified by agarose gel electrophoresis. Plasmid p154 was digested with restriction enzymes BclI and XmaI and the intervening piece was removed and replaced by the BclI–AvaI DNA fragment from p152 (XmaI and AvaI have compatible cohesive ends). Thus, the core gene under λPr control minus the four terminal 3' codons was inserted into the multiple-cloning site of the α-region in p154 creating an in-frame gene fusion expressing an HBV core antigen-α fusion peptide. This new core-α expressing plasmid is referred to as plasmid p157. The fusion peptide will be purified and used with antibody to construct an immunoassay for Hepatitis core antigen in a procedure analogous to that outlined in Section 8.3.

10. EXAMPLE: IMMUNOASSAY FOR HUMAN CHORIONIC GONADOTROPIN

10.1. Preparation of Human Chorionic Gonadotropin Enzyme Donor Fusion Peptides by Recombinant Methods This example illustrates the construction of β-human chorionic gonadotropin (β-hCG) fusion peptides for use in an immunoassay for β-hCG.

hCG is a glycoprotein composed of two noncovalently bound subunits designated α(16,000 daltons MW) and β(22,000 daltons MW). The α subunit is common to hCG and the related glycoproteins, leutropin (LH), thyrotropin (TSH) and follitropin (FSH). The β subunits of these hormones although distinct contain a high degree of amino acid homology. The β subunit of hCG, however, contains a unique 30 amino extension at the carboxy terminus.

This unique sequence was constructed by recombinant DNA techniques. Four DNA fragments were synthesized on an Applied Biosystems, Inc. Model 380A DNA Synthesizer (as described in Section 6.1.4) and have the following sequences:

(a) hCGS1 (62 mer) 5'AATTCCAGGACTCCTTCTCCT-TCAAAGGCCCCTCCCCCCAGCCTTC-CAAGCCCATCCCGACTC3'

(b) hCGS2 (37 mer) 5'CCGGGGCCCTCGGACAC-CCGATCCTCCCACAATAAG3'

(c) hCGNI (62 mer) 5'CCCGGAGTCGGGATGGGCTTG-GAAGGCTGGGGGGAGGGGCCTTTGAG-GAAGAGGAGTCCTGG3'

(d) hCGN2 (37 mer) 5'TCGACTTATTGTCGGGAG-GATCGGGGTGTCCGAGGGCC3'

DNA fragments (a) and (b) were ligated and fragments (c) and (d) were ligated. These two complementary DNA strands were annealed to form a DNA fragment which codes for the 30 amino acids carboxy terminus extension of the β-hGG subunit shown below:

```
                Eco  RI
            AAT TCCAGGACTCCTCTTCCTCAAAGGCCCCTCCCCCCAGCCTTCCAAGCCCATCCCGACT
                GGTCCTGAGGAGAAGGAGT TTCCGGGGAGGGGGGTCGGAAGGT TCGGGTAGGGCTGA

ApaI
            Sma I       I                                          Sal I
            CCCGGGGCCCTCGGACACCCCGATCCTCCCACAAT AAG
            GGGCCCCGCGGGAGCCTGTGGGGTAGGAGGGT GTTATTCAGCT
            Ava  I
```

The DNA fragment contains a 5' EcoRI restriction enzyme site and a SalI restriction enzyme site at the 3' end following the translation termination codon TAA.

This DNA fragment was inserted into plasmid p154, described in Section 9. Plasmid p154 was cleaved with EcoRI and SalI to remove the ωJ-region from the enzyme-donor (ED) gene and agarose gel purified. The EcoRI-SalI β-hCG DNA fragment was ligated to the gel purified p154 vector. The resultant plasmid, designated p166, contains a gene which codes for an ED-βhCG carboxy terminus fusion peptide (See FIG. 20). Enzyme-donor peptide ED166 contains 93 amino acids; amino acids 1–63 code for the α-donor domain and amino acids 64(*)–93 code for the β-hCG carboxy terminus as shown below:

```
                 5                  10                  15
Met Asp Pro Arg Ala Ser Ser Asn Cys Ser Cys Asn Ser Leu Ala
                20                  25                  30
Val Val Leu Gln Arg Arg Asp Trp Glu Asn Pro Gly Val Thr Glu
                35                  40                  45
Leu Asn Arg Leu Ala Ala His Pro Pro Phe Ala Ser Trp Arg Asn
                50                  55                  60
Ser Glu Glu Ala Arg Thr Asp Arg Pro Ser Gln Gln Leu Arg Ser
               *64 65              70                  75
Leu Glu Phe Gln Asp Ser Ser Ser Ser Lys Ala Pro Pro Pro Ser
                80                  85                  90
Leu Pro Ser Pro Ser Arg Leu Pro Gly Pro Ser Asp Thr Pro Ile
Leu Pro Gln
```

A second β-hCG fusion peptide was constructed by first synthesizing a DNA fragment of the following sequence:

```
       CGCGAAT TCTAGAT AAAT GAG          (21 mer)
       TAGCGCTTAAGATCTATTTACTCAGCT       (27 mer)
       Pvu I    Eco RI            Sal I
```

Plasmid p154 was cleaved with BamHI and PvuI and the small α-donor region was gel purified. The BamHI-PvuI fragment was ligated to the DNA synthesized fragment. This fragment was cleaved with BamHI-EcoRI and the reduced α-region domain was substituted for the BamHI-EcoRI α-domain in p166. The resultant plasmid, designated p175, coded for an enzyme-donor (ED175) of 85 amino acids. As shown below, amino acids 1–55 encode the α-donor domain and amino acids 56(*)–85 code for a portion of the β-hCG peptide:

```
                 5                  10                  15
Met Asp Pro Arg Ala Ser Ser Asn Cys Ser Cys Asn Ser Leu Ala
                20                  25                  30
Val Val Leu Gln Arg Arg Asp Trp Glu Asn Pro Gly Val Thr Glu
                35                  40                  45
Leu Asn Arg Leu Ala Ala His Pro Pro Phe Ala Ser Trp Arg Asn
                50                  55 *56              60
Ser Glu Glu Ala Arg Thr Asp Arg Glu Phe Gln Asp Ser Ser Ser
                65                  70                  75
Ser Lys Ala Pro Pro Pro Ser Leu Pro Ser Pro Ser Arg Leu Pro
                80                  85
Gly Pro Ser Asp Thr Pro Ile Leu Pro Glu
```

Another α-donor domain which was fused to the β-hCG carboxy terminus sequence shares the same amino terminus as the H6 α-donor domain described in Section 6.1.4 and FIG. 11. Plasmid p169 which contains ED H6 was cleaved with BamHI and EcoRI and the linear vector was gel purified. A synthetic DNA fragment, H6PM, of the following sequence:

```
                SmaI       SacI
            GATCCCCGGGCGAGCTCC
                GGGCCCGCTCGAGGTTAA
            Bam  HI           Base ↑Change
``` was inserted into the plasmid p169. Insertion of this synthetic DNA fragment destroyed the EcoRI site, but did not result in a change in the amino acid sequence. The resultant plasmid therefore has no EcoRI site. The α-domain was removed from this plasmid by digestion with BamHI and PvuI and substituted into p154 after digestion of p154 with BamHI and PvuI (as described above for the construction of p175), to create p174.

Plasmid p174 encodes an α-donor domain of 51 amino acids and contains an EcoRI site between the enzyme donor α and ω regions. The α-donor domain was removed from p174 by digestion with BamHI and EcoRI and gel purified. Plasmid p166 was digested with BamHI and EcoRI and the α-donor domain from p174 was inserted into p166. The resultant plasmid, p177 contains an α-donor domain fused to the carboxy terminus β-hCG DNA fragment. This enzyme-donor peptide, ED 177, has 81 amino acids. Thus, ED177 is 4 amino acids shorter than ED175.

10.2 Human Chorionic Gonadotropin Assay

This example demonstrates a highly sensitive homogeneous cloned enzyme donor immunoassay for human chorionic gonadotropin (hCG). Furthermore, in this example attachment of a secondary antibody (rabbit anti-hCG) enhances inhibition of complementation with EA22 (see infra Section 14).

The β-hCG enzyme-donor was constructed as described in Section 10.1. In this experiment, ED175 was used as the enzyme donor.

The immunoassay was performed using a microtiter format. Assays were performed by adding 50 μl of the appropriate concentration of hCG ($1\times10^3$, $3\times10^3$ and $5\times10^3$ mIU); 50 μl of a 1:100 dilution of polyclonal rabbit anti-hCG antibody (Lot #01-302-57 Immunosearch, Toms River, N.J.); and 50 µl of ED175 (1×10⁻⁸M). All dilutions were in PM2 buffer. The reaction mixture was incubated for 30 minutes at 37° C. Fifty µl of a 1:10 dilution of goat-anti-rabbit antibody was added (Antibodies, Inc., Davis, Calif.), and the reaction mixture was incubated for 30 minutes at 37° C. The mixture was then reacted with 50 µl of the enzyme-acceptor EA22 (1×10⁻⁷M) and ONPG substrate (5 mg/ml). The microtiter plates were incubated at 37° C. and $OD_{414}$ was measured.

Results are graphically illustrated in FIG. 21. This example demonstrates a dose-response curve suitable for use in a homogeneous immunoassay. This assay can be used to test for hCG either as a tumor marker or as an indicator of pregnancy.

11. EXAMPLE: ASSAY FOR BIOTIN

This example illustrates a competitive binding assay for biotin utilizing the glycoprotein avidin as the analyte-binding protein.

Avid in (MW=67,000 daltons) binds biotin (MW=244 daltons) with an association constant of $10^{15}$ L/M. Biotin was bound to the lysine at position 65 and the N-terminal α-amino group of H6. Avidin in solution was used as the analyte binding protein to determine whether the avidin coupled to the enzyme-donor inhibited complementation with EA23.

Coupling of biotin to the enzyme-donor H6 was performed as follows. Lyophilized H6, prepared as described in Section 6, was dissolved in 0.15 ml of 0.1M Na phosphate, pH 7.5 and stirred at room temperature. Two 5 µl aliquots of N-hydroxysuccinimidobiotin (Sigma Chemical, St. Louis, Mo.) at 10 mg/ml in N,N-dimethylformamide (DMF) were added. After one hour at room temperature the solution was centrifuged and the supernatant applied to a Bio-Gel P-2 (0.6×16 cm) sizing (BioRad Labs, Richmond, Calif.) column equilibrated with 0.1M Na borate pH 9.0 and eluted with the same buffer. Ten drop fractions were collected and fractions containing the biotinyl-H6 conjugate (i.e., complementation activity) were pooled.

In a preliminary experiment, a titration was performed to determine the concentration of avidin required to inhibit complementation. PM2 Buffer, a biotinylated-H6, avidin, EA23 and substrate O-nitrophenyl-β-D-galactopyranoside were added to microtiter plate. After 15 minutes at 37° C., the optical density at 414 nm ($OD_{414}$) was determined. Table IV shows the results. This data demonstrates that 0.5 µg avidin (7.5×10⁻¹² moles) inhibits 75% of the complementation reaction.

TABLE IV

INHIBITION OF COMPLEMENTATION BY BINDING TO AVIDIN[a]

| Well | Avidin (µg) | $OD_{414}$ |
|---|---|---|
| 1 | 0 | 0.545 |
| 2 | 0.1 | 0.499 |
| 3 | 0.2 | 0.438 |
| 4 | 0.3 | 0.370 |
| 5 | 0.5 | 0.133 |
| 6 | 1.0 | 0.123 |

[a]2.5 µl of Biotinylated-H6, prepared as described; 20 µl EA23 (3.6 × 10⁷M); and 100 µl substrate O-nitrophenyl-β-D-galactopyranoside (ONPG) (10 mg/ml) were used/well. Sufficient PM2 Buffer was added to each well to bring the final volume to 200 µl.

Figure 6:
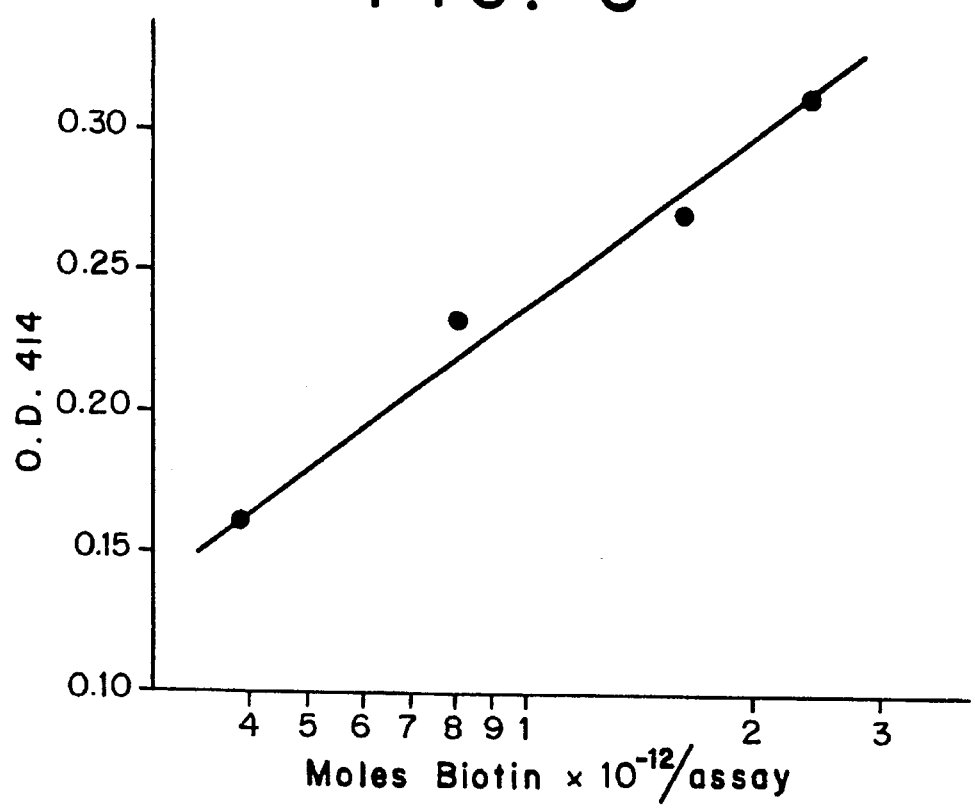

A competitive binding assay for biotin was performed as described for the preliminary experiment, except that varying concentrations of free D-biotin (Sigma Chemical, St. Louis, Mo.) were added to generate a competitive binding curve. Thus, each well contained: 5 µl Biotin-H6; 0.5 µg avidin; 20 µl EA23 (3.6×10⁻⁷M); 100 µl ONPG (10 mg/ml) substrate; and from 1 to 8 µl D-Biotin (1 µg/ml) with sufficient PM2 Buffer to bring the total volume to about 200 µl. The optical density (414 nm) was measured after 15 minutes. Data are graphically illustrated in FIG. 6. As demonstrated, this assay system provides a good assay for biotin over the range of 1 to 8 mg or 4–32×10⁻¹²M biotin. The avidin-biotin system ($k_a=2\times10^{15}$ L/M) has sufficient affinity to control complementation ($k_a=1-2\times10^5$ L/M) within a 15 minute assay.

12. EXAMPLE: HETEROGENEOUS COMPLEMENTATION ASSAY FOR BIOTIN

This example illustrates a heterogenous assay system for biotin utilizing avidin as the specific analyte-binding protein. The enzyme-acceptor is EA23, and the enzyme-donor is CNBr2 coupled to biotin (hereinafter, CNBr2-biotin conjugate).

CNBr2-biotin conjugate was synthesized as follows: 900 µg of lyophilized CNBr2 polypeptide was dissolved in 300 µl of 0.1M sodium phosphate buffer, pH 7.5. A 200 µl aliquot of N,N-dimethylformamide (DMF) containing 2.1 mg of [N-hydroxy-(d-biotin succinimide ester, or N-hydroxysuccinimidobiotin) succinimide activated biotin (Sigma Chemical Co., St. Louis, Mo.)] was added in 20 µl aliquots with stirring at room temperature. After 2 hours, the reaction mixture was chromatographed on a Biogel P-2 column (1.5×48 cm) using 0.1M sodium borate buffer, pH 9.0. The fractions containing the CNBr2-biotin conjugate were identified by the complementation reaction with EA23.

Avidin immobilized agarose (avidin-agarose, Sigma Chemical Co., St. Louis, Mo.) 17.5 units per µl suspension, where 1 unit binds 1 µg of biotin) stock was diluted in a low gelling temperature agarose suspension (6 mg/ml) to give the desired level of avidin-agarose.

12.1 Inhibition of CNBr2-Biotin Complementation Activity by Avidin-Agarose

Figure 7:
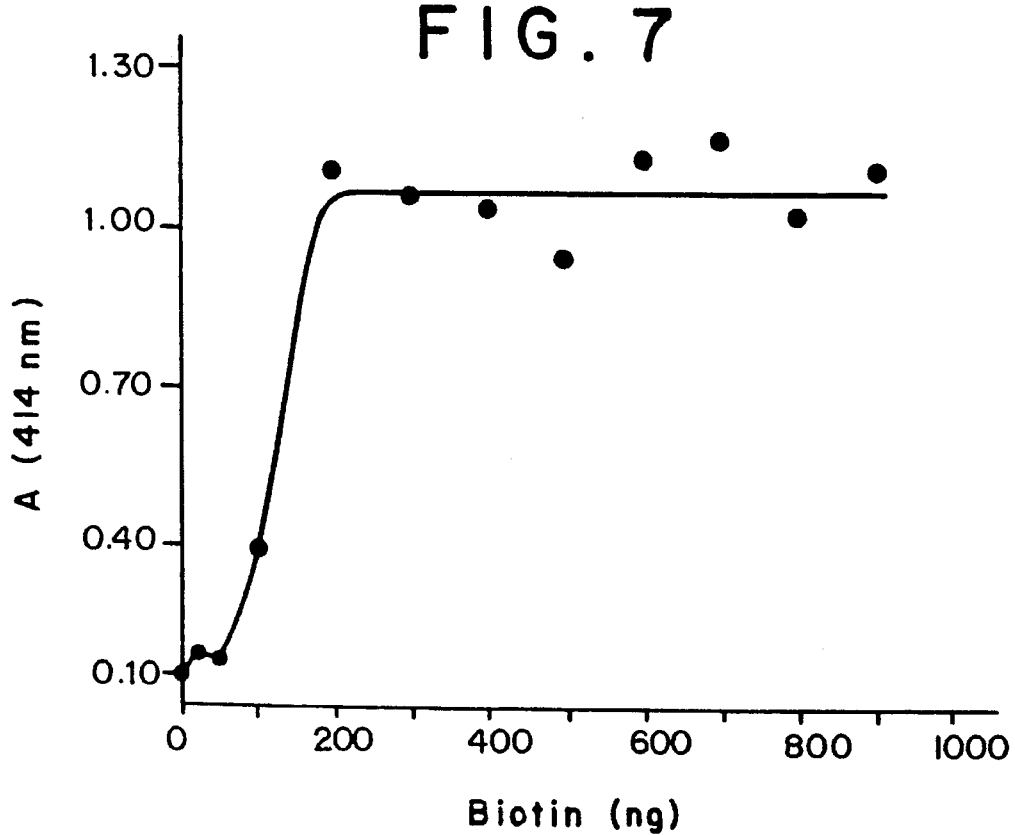

20 µl of CNBr2-biotin conjugate stock (5×10⁻⁷M), 90 µl of PM2 Buffer and 20 µl of avidin-agarose of various dilutions were mixed well in eppendorf vials and incubated at room temperature for 10 minutes. The vials were then centrifuged for 5 minutes and 100 µl of the supernatant was removed from each vial into microtiter wells, each containing 10 µl EA23 stock (1.5×10⁻⁶M) and incubated at 37° C. for 15 minutes. The substrate ONPG (100 µl of 10 mg/ml) was then added and the absorption of each well at 414 nm was measured after 30 minutes at 37° C. The results are graphically illustrated in FIG. 7.

Figure 8:
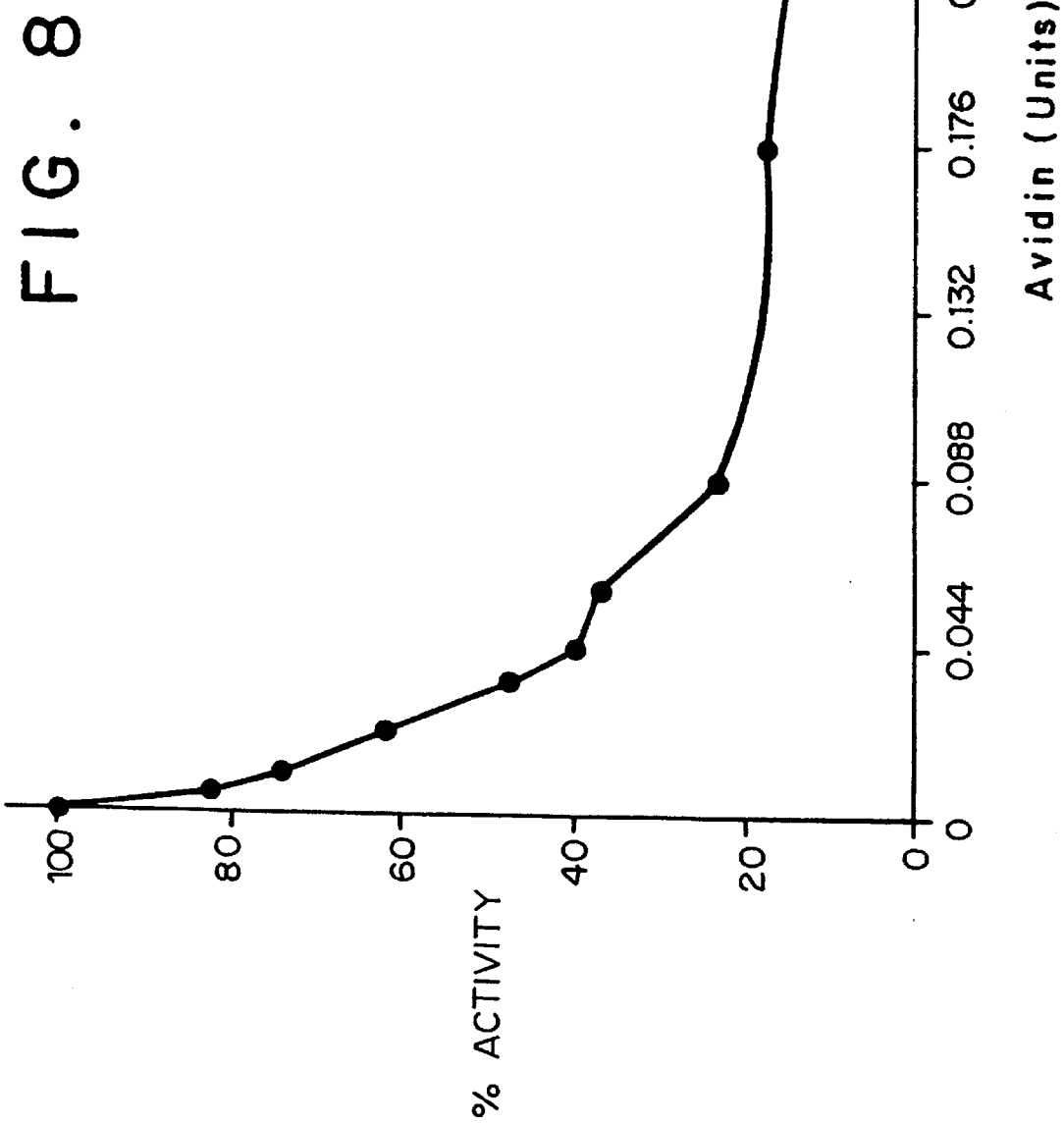

12.2 Competition of Biotin with CNBr2-Biotin Conjugate for Immobilized Avidin Using the titer value determined above, the biotin dose response curve is obtained as follows. 20 µl of avidin-agarose suspension (total 0.35 units), and 90 µl of PM2 Buffer containing various levels of biotin were mixed well in eppendorf vials and incubated at room temperature for 10 minutes. Then 20 µl of CNBr2-biotin conjugate stock (5×10⁻⁷M) was added, mixed well and incubated at room temperature for 10 minutes. The vials were then centrifuged for 5 minutes and 100 µl of the supernatant was removed from each vial into microtiter wells, each containing 10 µl EA23 stock (1.5×10⁻⁶M) and incubated at 37° C. for 15 minutes. Substrate ONPG (100 μl of 10 mg/ml) was added and the absorption of each well at 414 nm was measured after 30 minutes incubation at 37° C. The dose response curve is graphically illustrated in FIG. 8. Such a curve can be used to quantitate the amount of biotin in an unknown sample.

13. EXAMPLE: ENZYME IMMUNOASSAY FOR DIGOXIN

This example illustrates an enzyme immunoassay wherein the analyte is the cardiotonic digitalis glycoside digoxin. The analyte-binding protein is an antibody specific for digoxin. The example further demonstrates that the mechanism of action of the assay is not analogous to the steric hinderance enzyme immunoassay using β-galactosidase described by Castro and Monji (1981, Methods in Enzymology 73:523–42).

13.1 Preparation of Digoxin-H6 Conjugate

A urethane derivative of digoxigenin specifically 3-O[m-maleimidophenylcarbamyl] digoxigenin which is represented by the formula:

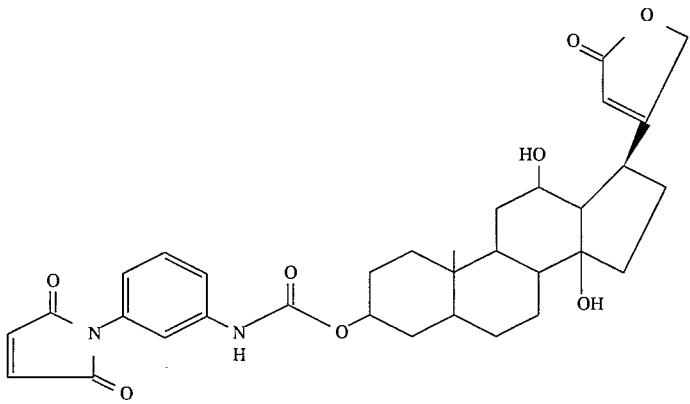

[hereinafter termed "digoxin-malemide adduct"] was prepared as follows:

To a dry 10 ml round bottom flask equipped with a magnetic stirring device, an argon inlet, and a reflux condenser, was added 3-carboxylphenylmaleimide (67 mg or 0.307 mmole), dry benzene (3 ml), and dry triethylamine (0.043 ml or 0.307 mmole). The mixture was refluxed for 30 minutes. An infrared spectra analysis (IR) of an aliquot showed conversion to carbonyl azide (2150 cm⁻¹). Digoxigenin (80 mg or 0.205 mmole) and dry tetrahydrofuran (2 ml) were then added to the reaction mixture. After 3.5 hours of refluxing, the reaction mixture was diluted with ethyl acetate (100 ml), washed once with 50 ml cold 1% aqueous NaOH, and once with 50 ml saturated aqueous NaHCO₃. The organic layer was then dried over anhydrous MgSO₄, filtered, and the solvent removed by rotary evaporation. The residue was dissolved in approximately 1–2 ml acetone and applied to two preparatve thin layer chromatography (TLC) plates (1500 micron silica gel Analtech uniplate, Analtech, Newark, Del.). When the acetone evaporated, the plates were eluted with 80/20 ethyl acetate/benzene. Unreacted digoxigenin was removed from the plate by scraping the correct UV active band from the plate and washing it 3 times with 30 ml of ethyl acetate. This process was repeated for the next two spots above digoxigenin. This purification afforded digoxigenin (26 mg), the desired product digoxin-maleimide adduct (31 mg or 37% yield based on unreacted starting material), and 12-O-(m-maleimidophenylcarbamyl)-digoxigenin (28 mg or 33% yield based on unreacted starting material).

Thin layer chromatography was performed in 2.5% MeOH-CH₂Cl₂ to ascertain the purity of the digoxin-maleimide adduct. If further purification is desired, this is best accomplished by preparative TLC with 3% MeOH/CH₂Cl₂ (2 elutions). The digoxin-maleimide adduct had the following spectral characteristics: Infrared (nujol mull): 3490, 3350, 1805, 1760, 1725, 1700, 1615, 1550, 1460, 1305, 1240, 1160, 960, 935, 905, 880, 840, 810, 790, 710 cm⁻¹. (NMR, Nuclear Magnetic resonance acetone d₆): 0.8 (3 H, s), 0.93 (3 H, s), 3.38 (1 H, brs), 3.40 (1 H, q, J=4.78 Hz(, 4.84 (2 H, t, J=1.5 Hz), 5.00 (1 H, m), 5.78 (1 H, t, J=1.5 Hz), 6.98 (s, 2 HO), 6.8–7.7 (4 H, m), 8.75 (1 H, br s). Mass Spectrum (CDI-NH₃): 622 (M+NH₄⁺), 605 (M+H⁺), 587 (M+H⁺-H₂O), 391, 373, 355, 337, 214, 191, 189.

The digoxin-maleimide adduct was then further purified on a RP-8 SynChropak 250×10 mm I.D. (SynChrom, Inc., Linden, Id.) using a Beckman Model 332 high performance liquid chromatography system (Beckman Instruments, Inc., Palo Alto, Calif.). Gradient elution was performed from 0–80% acetonitrile in H₂O over 60 minutes at a 1.5 ml/minute flow rate. The digoxin-maleimide adduct was pooled and lyophilized.

The purified digoxin-maleimide adduct was then coupled to the enzyme-donor H6, prepared as described supra, to form digoxin-H6, an enzyme-donor analyte conjugate. H6 (1.5 mg) was dissolved in 240 μl acetonitrile-50 mM sodium phosphate (3:2) at pH 6.0. Digoxin-maleimide adduct (1.0 mg) was added directly to the reaction mixture which was maintained at 37° C. for two hours. Upon completion of the coupling reaction, 60 μl aliquots of the mixture were injected onto a Bondapak® Phenyl column 10×30 cm (Waters Associates, Milford, Mass.). The column was developed with a 60 minute gradient 0–80% acetonitrile in H₂O, 0.1% trifluoroacetic acid. Samples containing enzyme-donor activity were pooled.

13.2 Immunoassay for Digoxin

In enzyme immunoassay systems prepared according to the methods of the present invention, varying combinations of concentrations of enzyme-acceptor and enzyme-donor conjugate (i.e., enzyme-donor coupled to analyte) can be used to produce a given β-galactosidase concentration via the complementation process. The law of mass action requires that at relatively high concentrations of enzyme-acceptor, the inhibitory influence of the antibody on the complementation process is mitigated. This is evidenced by flat or absent dose-response characteristics with varying concentrations of analyte e.g., digoxin. Conversely, at relatively high concentrations of enzyme-donor conjugate (compared to antibody), the inhibitory influence of the antibody on the complementation process is also lost. The latter situation is also evidenced by flat or absent dose-response characteristics and an elevated background.

This example illustrates that just as in conventional enzyme immunoassays, the relative concentrations of enzyme-acceptor, enzyme-donor and specific antibody must be defined to produce an assay with dose-response characteristics having suitable precision (slope) and sensitivity for use in a diagnostic assay for analyte.

In one series of experiments using a microtiter format, the sensitivity of the system was determined using different combinations of digoxin-H6 enzyme-donor and EA23 enzyme-acceptor concentrations.

Assays were performed by adding four sequential additions of 50 µl each, digoxin (analyte), enzyme-donor H6 digoxin conjugate, antibody specific for digoxin (anti-digoxin) and solution containing both enzyme, enzyme-acceptor (EA23) and O-nitrophenyl-β-D-galactopyranoside (ONPG) 5 mg/l as substrate. All dilutions were performed in PM2 Buffer [0.5M $Na_2HPO_4$, 1 mM $MgSO_4$, 0.18 mM $MnSO_4$, 1 mM EDTA, 0.02% $NaN_3$ and 0.05% Tween 20 (polyoxyethylene sorbitan monolaurate, Sigma Chemical Co., St. Louis, Mo.)]. The concentrations of the digoxin analyte were: 0, 1, 10, 100, 200, 500 and 1000 ng/ml. Antibody specific for digoxin was obtained by injection of digoxin conjugate into rabbits as follows: Primary intramuscular injections were made using 50 µg of conjugate in a total volume of 2.0 ml complete Freund's adjuvant. Boosters (intramuscular) were administered at 4-week intervals with 25 µg of conjugate in a volume of 1.0 ml complete Freund's adjuvant. 50 ml bleeds were collected every two weeks starting 90 days following primary injection. Collections were made by phlebotomy of the medial artery or lancing of the marginal ear veins. Blood was allowed to coagulate and 25 ml serum/50 ml blood recovered as supernatant following 30 minutes centrifugation at 1000×g.

Results are graphically illustrated in FIG. 9 (A and B). Comparison of the dose-response curves in FIG. 9A and FIG. 9B shows that selective reduction of the concentration of either enzyme-acceptor or enzyme-donor conjugate produces a steeper, and hence more sensitive dose-response curve.

13.3 Mechanism of Digoxin Immunoassay

In order to determine whether reacting the anti-digoxin antibody with the enzyme-donor digoxin conjugate was interfering with the complementation process rather than with conversion of substrate by polymerized β-galactosidase enzyme, the complementation process was allowed to proceed to completion prior to addition of antibody in one series of experiments.

The protocol of the experiments was as follows: 300 µl of PM2 Buffer and the digoxin-H6 conjugate were reacted for 60 minutes with 150 µl of the enzyme-acceptor EA23 ($4.1 \times 10^{-6}$M). This permitted the complementation to proceed to completion. An aliquot (125 µl) of the above reaction mixtured was removed and added to an aliquot (50 µl) of rabbit anti-digoxin antibody (diluted 1:100 with PM2 Buffer). The reaction mixture was then incubated for 30 minutes. At the end of this time period, the ONPG substrate (final concentration 1 mg/ml) was added and the reaction mixture incubated at 37° C. The optical density of the reaction mixture was determined at 7 and 16 minutes following incubation at 37° C. Control tubes were treated similarly except that 50 µl of either normal rabbit serum diluted 1:100 with (PM2 Buffer) or PM2 Buffer was added instead of rabbit anti-digoxin antiserum. Results are illustrated in Table V.

TABLE V

| Sample | Optical Density Incubation Time | |
|---|---|---|
| | 7 Minutes | 16 Minutes |
| Anti-digoxin[a] | .475 | .947 |
| NRS[b] | .466 | .954 |
| PM2[c] | .457 | .936 |
| Substrate blank | .050 | .057 |

[a]Antidigoxin designates, rabbit 539 (50 µl, 1:100 dilution in PM2 Buffer).
[b]NRS designates normal rabbit serum (50 µl, 1:100 dilution in PM2 BUffer).
[c]PM2 Buffer: 0.5M $Na_2HPO_4$, pH 7.0, 1 mM $MgSO_4$, 0.18 mM $MnSO_4$, 1 mM EDTA, 0.02% $NaN_3$, 0.05% Tween 20).

As demonstrated in Table V, antibody did not inhibit conversion of substrate by the previously polymerized β-galactosidase (complete complementation of Digoxin-H6 and EA23 enzyme-acceptor). Thus, the decreased substrate conversion observed using the enzyme assay is the result of antibody-inhibited complementation, not reduced enzyme substrate conversion. Therefore, the mechanism of action of the assay of the present invention is not analogous to the steric hinderance enzyme immunoassay using β-galactosidase described by Castro and Monji (1981, Methods in Enzymology 73:523–542).

13.3.1 Effect of Anti-Digoxin Antibody on Complementation Using a variety of Enzyme-Acceptors In one series of experiments, the inhibitory effect of specific antibody against digoxin was determined using three enzyme-acceptors and the enzyme-donor digoxin-H6 conjugate prepared as described in Sections 7.2 and 13.1.

The reaction mixture was prepared as follows: 50 µl PM2 Buffer, 50 µl of the appropriate dilution (1:20, 1:40, 1:80) of digoxin-H6 conjugate in PM2 Buffer; 50 µl of the appropriate antibody (i.e., either anti-digoxin antibody or normal rabbit serum) and 50 µl of the appropriate mixture of enzyme-acceptor ($1 \times 10^{-7}$M EA14, EA20 or EA22) and substrate O-nitrophenol-β-D-galactopyranoside (ONPG) (5 mg/ml) were added to a microtiter plate. The plates were then incubated at 37° C. for specified time periods. The optical density at 414 nm was determined at 5 minute intervals for 45 minutes.

The inhibitory effect of antibody on complementation in this system appears to relate to the size of the deletion in the enzyme-acceptor. Enzyme-acceptor EA22 which deletes amino acids 13–40 (see FIG. 5) and is the largest deletion tested in this experiment was inhibited least by antibody. Enzyme-acceptor, EA14 which deletes amino acids 30–37 (see FIG. 5) is the smallest of the tested group and was inhibited the most by antibody. EA20 which comprises amino acids 26–45 (see FIG. 5) and is intermediate in size between EA22 and EA14 was relatively moderately inhibited. The native complementation efficiency of EA20 is, however, lower than that of either EA14 or EA22. The enzyme-acceptor must satisfy two criteria: (a) native complementation efficiency (e.g., EA14 and EA22 are more efficient than others illustrated in FIG. 5 based on equimolar concentrations; and (b) the ability of specific analyte-binding protein to inhibit complementation.

14. EXAMPLE: EFFECT OF A SECOND ANTIBODY ON THE DIGOXIN ENZYME IMMUNOASSAY

The results presented supra in Section 12.3 suggest that coupling of anti-digoxin antibody to the enzyme-donor-digoxin conjugates of the present invention slows down the rate of complementation of enzyme-acceptor and enzyme-donor conjugate. Such coupling, however, does not completely prevent complementation. Thus, as stated in Section 13.3, the system has greatest sensitivity at approximately 15 minutes incubation of enzyme-acceptor and enzyme-donor conjugate.

The system reaches maximum absorbance differential at approximately 15 minutes. At that time the concentration of β-galactosidase in a system with anti-digoxin antibody present is the same as that in a system in which the antibody is absent, or in which digoxin antibody is neutralized (e.g., high digoxin levels). Since the β-galactosidase concentration is the same, the rate of substrate conversion is the same. No additional absorbance differential occurs. This phenomenon, which limits the effectiveness of the antibody on complementation produces a narrow absorbance range for a dose-response curve, flat slope characteristics and inadequate sensitivity of the assay for some diagnostic applications.

The following example demonstrates that attachment of a secondary antibody, specific for the anti-digoxin conjugate antibody, enhances the inhibition of complementation.

14.1 Attachment of Whole Secondary Antibody

In one series of experiments, 50 µl of rabbit anti-digoxin antibody (diluted 1:1000) was combined in a set of microtiter wells with 50 µl of digoxin-H6 (diluted 1:50 in PM2 buffer), and 50 µl of digoxin, ranging from 0, 1, 2.5, 5, 7.5, 10, 100 ng/ml. A 50 µl aliquot of a secondary antibody preparation (Bethyl Lab, Montgomery, Tex., goat anti-rabbit serum 1:50–1:800) was added to each well. Results are tabulated in Tables VI and VII.

TABLE VI

EFFECT OF SECONDARY ANTIBODY ON RATE OF SUBSTRATE CONVERSION

| | Rate of Substrate Conversion ($OD_{414}$/Time)[a] | | | | | | | |
|---|---|---|---|---|---|---|---|---|
| Dilution | 0–16 Minutes | | 16–30 Minutes | | 35–40 Minutes | | 45–60 Minutes | |
| Secondary Antibody[b] | OD/Time | % Prim. | OD/Time | % Prim. | OD/Time | % Prim. | OD/Time | % Prim. |
| 1:50 | .002 | 67 | .004 | 57 | .005 | 39 | .006 | 40 |
| 1:75 | .002 | 67 | .004 | 57 | .007 | 54 | .009 | 60 |
| 1:100 | .002 | 67 | .006 | 86 | .009 | 69 | .011 | 73 |
| 1:200 | .003 | 100 | .007 | 100 | .012 | 92 | .013 | 87 |
| 1:300 | .003 | 100 | .007 | 100 | .012 | 92 | .014 | 93 |
| 1:400 | .003 | 100 | .007 | 100 | .013 | 100 | .014 | 93 |
| 1:800 | .003 | 100 | .007 | 100 | .013 | 100 | .014 | 93 |

[a]In all cases the rate of substrate conversion by the assay system using primary antibody without the secondary antibody was designated 100%. The measured rate for this preparation ($OD_{414}$/Time) was: .003, .007, .013, .015 at 0–16; 16–30; 30–45; and 45–60 minutes, respectively.
[b]Secondary antibody used was goat anti-rabbit antibody (Bethyl Labs, Montgomery TX). All dilutions were prepared using PM2 Buffer. The primary antibody was rabbit anti-digoxin antibody diluted in all cases 1:1000.

As demonstrated in Table VI, the inhibitory effect on complementation achieved by attaching a secondary antibody to the antibody-digoxin H6 conjugate is optimal at a 1:50 dilution or less of the secondary antibody. At a dilution of 200 to 1:300 of the secondary antibody, all synergistic inhibition is lost. Thus, inhibition of complementation with or without secondary antibody is the same at this dilution or greater.

TABLE VII

EFFECT OF SECONDARY ANTIBODY ON SUBSTRATE CONVERSION

| | | Rate of Substrate Conversion | | | | | | |
|---|---|---|---|---|---|---|---|---|
| Primary | Dilution | 0–16 Min | | 16–30 Min | | 30–45 Min | | 45–60 Min | |
| Antibody[a] | Secondary Antibody[b] | OD/Time | % Max. | OD/Time | % Max. | OD/Time | % Max. | OD/Time | % Max. |
| Rα Dg | — | .002 | 50 | .007 | 70 | .010 | 71 | .010 | 77 |
| NRS | — | .004 | 100 | .010 | 100 | .014 | 100 | .013 | 100 |
| Rα Dg* | 1:5 | .004 | 100 | .007 | 54 | .003 | 23 | .003 | 23 |
| NRS | 1:5 | .004 | 100 | .013 | 100 | .013 | 100 | .013 | 100 |
| Rα Dg* | 1:10 | .004 | 100 | .005 | 39 | .003 | 21 | .003 | 21 |
| NRS | 1:10 | .004 | 100 | .013 | 100 | .014 | 100 | .014 | 100 |

TABLE VII-continued

EFFECT OF SECONDARY ANTIBODY ON SUBSTRATE CONVERSION

| Primary Antibody[a] | Dilution Secondary Antibody[b] | Rate of Substrate Conversion | | | | | | | |
|---|---|---|---|---|---|---|---|---|---|
| | | 0–16 Min | | 16–30 Min | | 30–45 Min | | 45–60 Min | |
| | | OD/ Time | % Max. | OD/ Time | % Max. | OD/ Time | % Max. | OD/ Time | % Max. |
| Rα Dg* | 1:20 | .003 | 60 | .003 | 25 | .003 | 21 | .003 | 21 |
| NRS | 1:20 | .005 | 100 | .012 | 100 | .014 | 100 | .014 | 100 |
| Rα Dg | 1:40 | .002 | 40 | .003 | 25 | .003 | 21 | .004 | 29 |
| NRS | 1:40 | .005 | 100 | .012 | 100 | .014 | 100 | .014 | 100 |
| Rα Dg | 1:80 | .001 | 20 | .004 | 36 | .006 | 43 | .006 | 43 |
| NRS | 1:80 | .005 | 100 | .011 | 100 | .014 | 100 | .014 | 100 |
| Rα Dg | 1:160 | .002 | 50 | .006 | 50 | .009 | 60 | .009 | 60 |
| NRS | 1:160 | .004 | 100 | .012 | 100 | .015 | 100 | .015 | 100 |

*Precipitation noted in wells.
[a]Primary antibody was either rabbit anti-digoxin (Rα Dg) or normal rabbit serum (NRS) diluted 1:1000 with PM2 Buffer.
[b]Secondary antibody designates goat anti-rabbit antibody.

As demonstrated in Table VII, with no secondary antibody, the rate of substrate conversion (i.e., β-galactosidase concentration) reached 70% of maximum within 30 minutes. With secondary antibody at a 1:40 dilution, the rate of substrate conversion was approximately 25% of maximum. At greater than 1:40 dilutions of secondary antibody, the inhibitory effect on complementation diminished as evidenced by increasing rates of substrate conversion over time.

At dilutions equal to or greater than 1:40, the effect is an increase in the rate of substrate conversion.

At all concentrations of secondary antibody tested, the rate of substrate conversion (i.e., β-galactosidase concentration) became linear (i.e., no new β-galactosidase produced) at levels below the maximum concentration of β-galactosidase the system would permit (e.g., NRS replaces secondary antibody). This indicates that binding of secondary antibody enhances steric interference of the primary antibody and may completely prevent complementation by that enzyme-donor population which is bound.

14.1.1 Dose Response: EA14 and Digoxin-P6

In another series of experiments, the sensitivity of the enzyme immunoassay was determined using digoxin (analyte) concentrations ranging from 0, 1, 10, 100, 1000 ng/ml, enzyme-acceptor EA14, rabbit anti-digoxin antibody and goat anti-rabbit antibody as secondary antibody. In these experiments different combinations of concentrations of the enzyme-donor digoxin-P6 prepared in an analogous manner to that described for digoxin-H6 conjugate (Section 13) and EA14 enzyme-acceptor were used. In each case the following protocol was used: in a microtiter format, 50 μl each of digoxin-P6, free digoxin analyte, and anti-digoxin antibody were added sequentially. Then 50 μl goat anti-rabbit (1:80) was added. The plates were then incubated at room temperature for 10 minutes. Then 50 μl each of the appropriate dilution of stock EA14 ($2.64 \times 10^{-5}$M) and O-nitrophenol-β-D-galactopyranoside substrate (5 mg/ml) were added. The plates were reincubated at 37° C., and absorbance of the reaction mixture was determined at 15 and 30 minutes. Absorbance of the substrate blank was subtracted from all samples.

Figure 10:
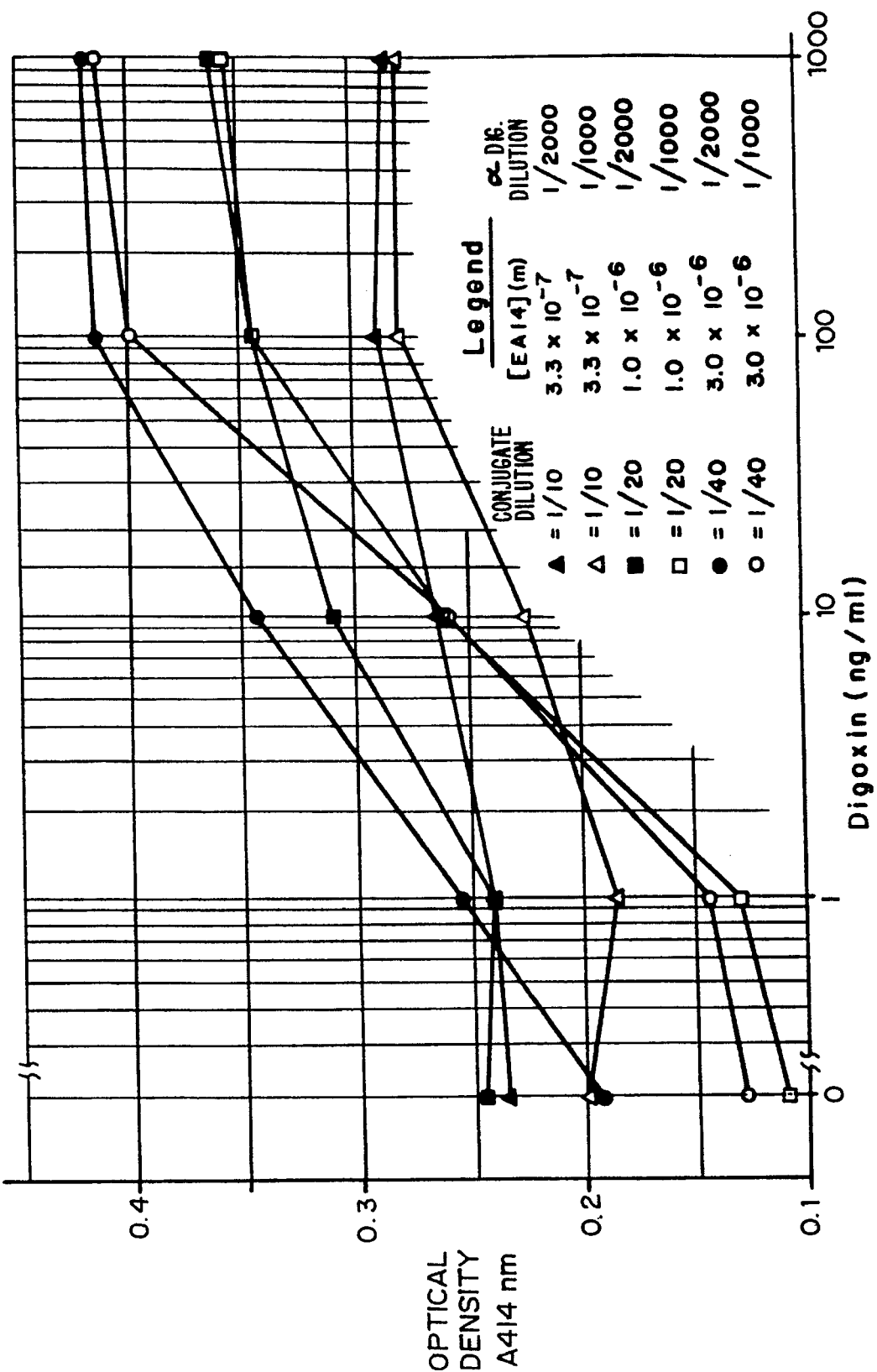

Results graphically illustrated in FIG. 10 demonstrate dose-response curves suitable for use in the digoxin assay.

14.2 Attachment of Fragment of Secondary Antibody

In order to determine whether the enhanced inhibition, observed when a secondary antibody was coupled to the primary antibody-enzyme-donor conjugate, could be attributed to steric hindrance or entrapment of enzyme-donor conjugate in a precipitin complex, monovalent Fab fragments (antigen binding fragments about 50,000 daltons MW) of goat anti-rabbit immunoglobulin were used as the secondary antibody. Because Fab fragments cannot cross link antigen they are not capable of inducing a precipitin or an agglutination reaction. Any inhibition of complementation observed in this preparation is due to enhanced steric effects on complementation and not to enhanced entrapment of conjugate.

In a microtiter plate format, five equal additions of 50 μl each sequentially of digoxin (0, 1, 4, 10, 1000 ng/ml); digoxin-H6 conjugate; rabbit anti-digoxin primary antibody (1:4000) and secondary goat anti-rabbit antibody (Bethyl Labs, Montgomery, Tex.) at 1:80 dilution. All dilutions were in PM2 Buffer. The secondary antibody was replaced by normal rabbit serum (1:80) and the Fab fragment of goat anti-rabbit serum (Cappel Laboratories, West Chester, Pa.) at dilutions of 1:10, 1:20, 1:40, 1:80, 1:160, 1:320. After 10 minutes at room temperature 50 μl of $1 \times 10^{-6}$M EA14 and 5 mg/ml the substrate ONPG was added and incubations continued 30 minutes at 37° C. $OD_{414}$ was measured and Bound/Maximum Bound (B/Bmax) determined.

The results are demonstrated in Table VIII.

TABLE VIII

EFFECT OF FAB FRAGMENTS

| Dilution of Secondary Antibody Preparation[a] | Rate of Substrate Conversion (B/B MAX) Concentration Digoxin (ng/ml) | | | | |
|---|---|---|---|---|---|
| | 0 | 1 | 4 | 10 | 1,000 |
| Goat anti-rabbit IgG[b] | 56.7 | 66.3 | 81.9 | 94.0 | 100 |
| None[c] | 95.4 | 91.3 | 88.7 | 97.1 | 100 |
| Fab 1:10 Goat anti-rabbit IgG[d] | 62.8 | 68.1 | 75.2 | 89.4 | 100 |
| Fab 1:20 Goat anti-rabbit IgG[d] | 57.6 | 67.6 | 75.5 | 87.1 | 100 |
| Fab 1:40 Goat anti- | 66.2 | 73.8 | 80.0 | 90.3 | 100 |

TABLE VIII-continued

EFFECT OF FAB FRAGMENTS

| Dilution of Secondary Antibody Preparation[a] | Rate of Substrate Conversion (B/B MAX) Concentration Digoxin (ng/ml) | | | | |
|---|---|---|---|---|---|
| | 0 | 1 | 4 | 10 | 1,000 |
| rabbit IgG[d] Fab 1:80 Goat anti-rabbit IgG[d] | 69.7 | 75.6 | 82.3 | 91.5 | 100 |
| Fab 1:160 Goat anti-rabbit IgG[d] | 77.4 | 78.5 | 83.1 | 92.1 | 100 |
| Fab 1:320 Goat anti-rabbit IgG[d] | 81.6 | 83.5 | 85.1 | 94.8 | 100 |

[a] All secondary antibody preparations were tested using primary antibody at 1:4000 dilution.
[b] Goat anti-rabbit immunoglobulin antiserum (Bethyl Labs, Montgomery, TX).
[c] None designates that no secondary antibody was used. A 1:80 dilution of normal rabbit serum replaced the secondary antibody in these samples.
[d] Fab Goat anti-rabbit IgG desinates the Fab fragment obtained from H and L Sp (Cappel 0412-0081 Lot #23167) (Cappel Laboratories, West Chester, PA).

As demonstrated in Table VIII, decreased complementation is evident when the goat anti-rabbit immunoglobulin (Fab fragment)is coupled to the primary antibody enzyme-donor conjugate. The inhibition of complementation induced by the Fab fragment is approximately equivalent to that inhibition observed when using whole antibody.

As shown in Table VIII, the secondary antibody had a greater inhibition effect on complementation at low dose (i.e., greater antibody/enzyme-donor interaction) than at high dose (i.e., less antibody enzyme-donor interaction be caused by excess free analyte).

Decreasing Fab concentration did produce a linear decline in complementation inhibition. In Table VI intact molecules demonstrated a decreased in secondary antibody effectiveness with dilution greater than 1:40. Likewise, the same phenomenon is seen beginning with 1:40 dilution of the Fab preparation.

14.3 Inhibition of Complementation by Analyte-Specific Antibodies: A Comparison of ED-Digoxin Conjugates Comparison of various ED-digoxin conjugates for specific inhibition of complementation activity by specific analyte antibodies was performed. In the experiment shown below, the complementation activity of the enzyme-donor coupled with EA22 was normalized. Digoxin-conjugates of the various ED's were prepared as previously described except for ED4 (2-digoxin) where the pH of coupling was raised to pH 9.5 to couple the digoxin-maleimide to both the α-amino group and the cysteine distal to the α-region. Anti-digoxin antibody and goat anti-rabbit antibody concentrations were both normalized. The results are shown in Table IX.

TABLE IX

INHIBITION OF COMPLEMENTATION BY ANALYTE-SPECIFIC ANTIBODIES

| Enzyme-Donor | % Inhibition of Complementation |
|---|---|
| ED5 | 66 |
| ED4 (2-digoxin) | 68 |
| ED4 | 51 |
| H6 | 37 |

15. IMPROVED THYROXINE AND DIGOXIN ASSAYS UTILIZING SECONDARY ANTIBODY

Thyroxine and digoxin enzyme complementation immounoassays were performed with secondary antibody.

The thyroxine (T4) assay was further refined with EA22 and ED4 on a centrifugal analyzer, the ENCORE® from Baker Instruments (Allentown, Pa.). The assay system consisted of 10 µl of patient sample, 100 µl of enzyme-acceptor reagent which also contained anti-T4 antibody and salicylate, and 290 µl of enzyme-donor reagent which also contained secondary goat anti-rabbit antibody and the substrate o-nitrophenyl-β-D-galactopyranoside (ONPG). The final system concentrations were as follows:

| | |
|---|---|
| enzyme-acceptor (EA22) | $0.625 \times 10^{-7}$M |
| 1° T4 antibody | 1/1200 |
| salicylate | 10 mM |
| enzyme-donor (ED4-T4) | 1/276 |
| 2° goat anti-rabbit antibody | 1/200 |
| ONPG | 0.51 mg/ml |

Readings were taken at 900 seconds. When various patient T4 samples are used, changes in O.D./minute must be plotted due to ±50m O.D. input at $O.D._{405}$ from individual patient samples. FIG. 18 shows a T4 assay with calibrators prepared in whole human serum. Changes in absorbance between calibrators at 900 seconds are plotted versus serum T4 concentration.

The digoxin assay was refined using ED5 and EA22 and the Baker ENCORE® centrifugal analyzer. Digoxin standards were prepared in human serum. The assay consisted of 30 µl of sera, 200 µl of ED5-digoxin reagent and 100 µl of the EA22 reagent. The ED5-digoxin reagent also contained substrate o-nitrophenyl-β-D-galactopyranoside and goat anti-rabbit antibody. The EA22 reagent contained rabbit anti-digoxin antibody. The final system concentrations were as follows:

| | |
|---|---|
| serum | 9.1% |
| EA22 | $2 \times 10^{-7}$ |
| ED5-digoxin | 1:1500 |
| 1° digoxin antibody | 1:59,400 |
| 2° goat anti-rabbit antibody | 1:200 |
| ONPG | 0.5 mg/ml |

A standard curve for this assay is presented in FIG. 19.

16. COMPARISON OF PERFORMANCE OF GENETICALLY ENGINEERED AND CHEMICALLY SYNTHESIZED ENZYME-DONORS IN DIGOXIN IMMUNOASSAY

To compare enzyme immunoassays performed with chemically synthesized versus genetically engineered components, two analogous enzyme-donors were prepared, one by recombinant DNA techinques and the other by chemical peptide synthesis. The amino acid sequences of ED3 created by genetic engineering (see Section 6.1.4) and ED3A created by polypeptide synthesis (see Section 6.1.5.) are shown in FIG. 14. The salient features of these two peptides are the analogous cysteine residue (Cys), marked with an asterisk in FIG. 14, used for chemical coupling to analyte and the analogous α-donor domain, which in ED3 is located between amino acids number 12 and 50, inclusive, and in ED3A is located between amino acids number 5 and 43, inclusive, and correspond to amino acids 6 through 44 of wild-type β-galactosidase.

Conjugation of digoxin to ED3 and ED3A was performed with 3-O[m-maleimidophenylcarbamyl] digoxigenin as described in Section 13.1. Preparations of ED3, ED3A, digoxin-ED3 and digoxin-ED3A were subjected to high performance liquid chromatography (HPLC) on a preparative HPLC henyl column (Waters μBondapak, Waters Assoc., Milford, Mass.) using a gradient of 0–80% acetonitrile in water containing 0.1% TFA as eluent. Column fractions of each enzyme-donor were assayed for complementation as described in Section 6.2.1 using M15 as enzyme acceptor. The relative complementation efficiency of ED3-digoxin was four times greater than ED3A-digoxin.

Column fractions corresponding to digoxin-ED3 and digoxin-ED3A were pooled separately and compared in a competitive enzyme immunoassay for digoxin.

A 96-well microtiter plate was used for the assay. The asay comprised 25 μl of human serum standards 0,0.5, 1, 2, 4, 10, 100 and 1000 ng/ml digoxin, 100 μl of reagent I which contains $4 \times 10^{-7}$M M15 enzyme-acceptor and digoxin antibody, and 130 μl of reagent II. Reagent II contained various dilutions of digoxin-ED3 or digoxin-ED3A, secondary goat anti-rabbit antibody and 1.1 mg/ml of o-nitrophenyl-β-D-galactopyranoside. The results following a 30-minute incubation at 37° C. and reading at 405 nm in a Titertek microtiter plate reader are shown in Table X. As seen in Table X, competitive immunoassays were created with both digoxin-ED3 and digoxin-ED3A. A curve for digoxin using digoxin-ED3A is shown in FIG. 17. The digoxin immunoassay with digoxin-ED3 gave better signal discrimination at the low doses of 0.5 and 1 mg/ml than digoxin-ED3A. This discrepancy may be due to the presence of impurities in the ED3A preparation which were detected during HPLC analysis.

These experiments demonstrate the applicability of synthesized polypeptides, as well as genetically engineered polypeptides, in the control of the complementation of β-galactosidase polypeptides by antigen-antibody reaction.

Hence, chemical polypeptide synthesis can be used to create enzyme-donors for the purpose of detecting high molecular weight proteins. Gene fusions that encode immunologically reactive polypeptide epitopes fused to the α-donor domain can also be synthesized. The limits on this approach include not only the state-of-the-art capabiity to synthesize ever larger polypeptides but also knowledge of the sequence of both the required α-donor domain and the immunologically reactive protein domain.

TABLE X

DIGOXIN ASSAY WITH ED3 AND ED3A

| Conjugate Dilution | Digoxin dose ng/ml | | | | | | | |
|---|---|---|---|---|---|---|---|---|
| | 0 | 0.5 | 1 | 2 | 4 | 10 | 100 | 1K |
| ED3 (Absolute OD) | | | | | | | | |
| 1/100 | .810 | .821 | .855 | .916 | .980 | 1.088 | 1.159 | 1.218 |
| 1/200 | .350 | .368 | .386 | .420 | .444 | .508 | .566 | .586 |
| 1/400 | .154 | .149 | .163 | .178 | .189 | .230 | .249 | .264 |
| 1/800 | .080 | .078 | .084 | .095 | .090 | .114 | .133 | .121 |
| ED3A (Absolute OD) | | | | | | | | |
| 1/100 | .668 | .656 | .660 | .660 | .668 | .719 | .757 | .777 |
| 1/200 | .310 | .306 | .309 | .322 | .329 | .352 | .372 | .375 |
| 1/400 | .146 | .146 | .153 | .152 | .151 | .192 | .180 | .180 |
| 1/800 | .043 | .039 | .047 | .043 | .048 | .060 | .064 | .052 |
| ED3 (ΔOD) | | | | | | | | |
| 1/100 | 0 | .011 | .045 | .106 | .170 | .278 | .349 | .408 |
| 1/200 | 0 | .018 | .036 | .070 | .094 | .158 | .216 | .236 |
| 1/400 | 0 | .005 | .009 | .024 | .035 | .076 | .095 | .110 |
| 1/800 | 0 | .002 | .004 | .015 | .010 | .034 | .053 | .041 |
| ED3A (ΔOD) | | | | | | | | |
| 1/100 | | −.012 | −.008 | −.008 | 0 | .051 | .089 | .104 |
| 1/200 | | −.004 | −.001 | −.012 | .019 | .042 | .062 | .065 |
| 1/400 | | 0 | .007 | .006 | .005 | .046 | .034 | .034 |

17. DEPOSIT OF MICROORGANISMS

The following *E. coli* strains carrying the listed plasmids have been deposited with In Vitro International, Inc. (IVI), Ann Arbor, Mich. or the Agricultural Research Culture Collection (NRRL), Peoria, Ill. and have been assigned the following accession numbers:

| *E. Coli* Strain | Plasmid | Accession Numbers |
|---|---|---|
| E9001 | p122 | IVI 10034 |
| E9001 | p125 | IVI 10035 |
| E9001 | pF29 | IVI 10038 |
| JM83 | p150 | IVI 10036 |
| JM83 | p157 | IVI 10037 |
| AMA 1004 | pMG14 | IVI 10050 |
| AMA 1004 | pMG22 | IVI 10051 |
| E9001 | p169 | IVI 10052 |
| E9001 | p183 | IVI 10053 |
| E9001 | p185 | IVI 10054 |
| AMA 1004 | p175 | NRRL-B18006 |

*E. coli* strain E9001, IVI 10034 and strain JM83, IVI 10037 contain plasmids p122 and p157, respectively, carrying genes coding for fusion proteins of part of the hepatitis B virus surface antigen and an α-donor as described in Section 8.1 and 9. *E. coli* strain E9001, IVI 10035 contains plasmid p125, as described in Section 6.1.1, carrying a gene coding for an enzyme-donor. *E. coli* strain E9001, IVI 10038 and strain JM83, IVI 10036 contain plasmids pF29 and p150, respectively, as described in Section 6.2, p150 carrying a gene which codes for an enzyme-acceptor. *E. coli* strain AMA 1004, IVI 10050 contains a plasmid, pMG14, which carries a gene for a β-galactosidase protein (enzyme-acceptor) with amino acids 30–37 deleted. See FIG. 5. *E. coli* strain AMA 1004, IVI 10051 contains a plasmid, pMG22, which carries a gene for a β-galactosidase protein (enzyme-acceptor) with amino acids 13–40 deleted. See FIG. 5. *E. coli* strain E9001, IVI 10052 contains p169, a plasmid which carries a gene coding for a fragment (ED H6) of β-galactosidase which has a cysteine residue at amino acid 62 and a lysine residue at amino acid 64. See Section 6.1.2. *E. coli* strain E9001, IVI 10053 contains p183, a plasmid which carries a gene coding for a fragment (ED3) of β-galactosidase which has a cysteine residue at amino acid 3. See Section 6.1.4. *E. coli* strain E9001, IVI 10054 contains p185, a plasmid which carries a gene coding for a fragment (ED5) of β-galactosidase which has a cysteine residue at amino acid 39. See Section 6.1.6. *E. coli* strain AMA 1004,NRRL B-18006 contains plasmid p175, carrying a gene coding for a fusion protein of the carboxy terminis of the B-hCG protein and an α-donor as described in Section 11 and FIG. 20.

The present invention is not to be limited in scope by the microorganisms deposited, since the deposited embodiments are intended as single illustrations of certain aspects of the invention and any microorganisms which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claim.

It is also to be understood that all base pair (bp) sizes given for nucleotides are approximate and are used for purpose of description.

What is claimed is:

1. An enzyme donor (ED) polypeptide having an amino acid sequence:

```
   (-5)                          (0)  (+1)
Met Asp Pro Ser Gly Asp         Pro  Arg  Ala  Ser (5)                         (10)
Ser Asn Ser Leu Ala Val         Val  Leu  Gln  Arg

(15)                        (20)
Arg Asp Trp Glu Asn Pro         Gly  Val  Thr  Gln

(25)                        (30)
Leu Asn Arg Leu Ala Ala         His  Pro  Pro  Phe

(35)                        (40)
Ala Ser Trp Arg Asn Ser         Glu  Glu  Ala  Arg

(45)                        (50)
Thr Asp Cys Pro Ser Gln         Gln  Leu  Arg  Ser

(55)                        (60)
Leu Asn Gly Leu Glu Ser         Arg  Ser  Ala  Gly

(65)
Met Pro Leu Glu
``` wherein one amino acid, at position 3, 20 or 39 above, is replaced with either cysteine or lysine.

2. An ED polypeptide of claim 1 wherein said amino acid at position 3, and one additional amino acid at position 46, are replaced with either cysteine or lysine.

3. An ED polypeptide having an amino acid sequence:

```
      (-20)                  (-15)
Met Asp Pro Ser Gly Asn Pro Tyr Gly Ile

Asp Pro Thr Gln Ser Ser Pro Gly Asn Ile (0)                    (5)
Asp Pro Arg Ala Ser Ser Asn Ser Leu Ala

(10)                   (15)
Val Val Leu Gln Arg Arg Asp Trp Glu Asn

(20)                   (25)
Pro Gly Val Thr Glu Leu Asn Arg Leu Ala

(30)                   (35)
Ala His Pro Pro Phe Ala Ser Trp Arg Asn

(40)                   (45)
Ser Glu Glu Ala Arg Thr Asp  X   Pro Ser

(50)                   (55)
Gln Gln Leu Arg Ser Leu Asn Gly Leu Glu

(60)                   (65)
Ser Arg Ser Ala Gly Met Pro Leu Glu
``` wherein X at position 46 equals cysteine or lysine.

4. An ED polypeptide having an amino acid sequence:

```
            (5)                    (10)
Met Asp Pro Arg Ala Ser Ser Asn Cys Ser

(15)                    (20)
Cys Asn Ser Leu Ala Val Val Leu Gln Arg

(25)                    (30)
Arg Asp Trp Glu Asn Pro Gly Val Thr Glu

(35)                    (40)
Leu Asn Arg Leu Ala Ala His Pro Pro Phe

(45)                    (50)
Ala Ser Trp Arg Asn Ser Glu Glu Ala Arg

(55)                    (60)
Thr Asp Arg Pro Ser Gln Gln Leu Arg Ser

(63)
Leu Glu Phe
```

5. An ED polypeptide of claim 4 wherein the amino acids at position 54 through 61 are deleted.

6. An enzyme complementation assay method for determining the amount of a suspected analyte in a sample which comprises the steps of:

(a) forming a reaction mixture by combining in a medium (1) the sample; (2) an ED polypeptide conjugate prepared by recombinant DNA techniques wherein said polypeptide conjugate is a fusion protein having an α-donor domain comprising an ED polypeptide of claims 4 or 5 capable of interacting with an enzyme-acceptor to form an active enzyme-complex and a protein domain comprising said analyte or an epitope of said analyte and wherein said analyte is a molecule with a molecular weight of about 2000 daltons or greater; (3) an analyte-binding protein specific for said analyte; (4) an enzyme-acceptor polypeptide capable of interacting with said ED polypeptide conjugate to form an active enzyme complex having the catalytic activity of β-galactosidase; and (5) a substrate capable of reacting with said active enzyme complex such that its rate of conversion by active enzyme can be monitored, wherein said enzyme-donor polypeptide conjugate is capable of binding to said analyte-binding protein, whereby said analyte-binding protein inhibits the formation of an active enzyme complex in the absence of analyte, the concentrations of analyte-binding protein, enzyme-acceptor and enzyme-donor conjugate being such that the amount of analyte detected in the system varies directly with the rate of conversion of the substrate;

(b) measuring the rate of conversion of substrate in the reaction mixture; and (c) determining the amount of analyte in the sample by comparing the rate of conversion of substrate to rates of conversion of substrate obtained using a known concentration of the analyte.

7. The method of claim 6, further comprising the step of: adding to the reaction mixture an antibody or antibody fragment specific for the analyte-binding protein, the effect of said antibody or antibody fragment being to increase the sensitivity of the method via enhanced steric hinderance effects on the interaction between the enzyme-donor conjugate and enzyme acceptor.

8. The method of to claim 6, wherein the rate is determined spectrophotometrically or fluorometrically.

9. The method of to claim 6, the analyte-binding protein is selected from the group consisting of antibody molecules, receptors, and transport proteins.

10. The method of to claim 6, wherein the analyte-binding protein is a polyclonal antibody or a monoclonal antibody.

11. The method of to claim 6, wherein the substrate is selected from the group consisting of p-aminophenyl-$\beta$-D-galactopyranoside; 2'-N-(hexadecanol-N(amino-1'-nitrophenyl-$\beta$-D-galactopyranoside; 4-methylumbelli-$\beta$-D galactopyranoside; napthyl-AS-B1-$\beta$-D-galactopyranoside; 1-napthyl-$\beta$-D-galactopyranoside; 2-napthyl-$\beta$-D-galactopyranoside monohydrate; O-nitrophenyl-$\beta$-D-galactopyranoside; m-nitrophenyl-$\beta$-D-galactopyranoside; p-nitrophenyl-$\beta$-D-galactopyranoside; 2-phenylethyl-$\beta$-D-galactopyranoside; phenyl-$\beta$-D-galactopyranoside, 5-bromo-4-chloro-3-indolyl-$\beta$-D-galactopyranoside, resorufin-$\beta$-D-galactopyranoside, 7-hydroxy-4-trifluoromethyl coumarin, $\omega$-nitrostyryl-$\beta$-D-galactopyranoside and fluorescein-$\beta$-D-galactopyranoside.

12. A method of claim 6 wherein the protein domain is selected from the group consisting of human chorionic gonadotropin or a fragment thereof, Hepatitis B Virus surface antigen or an epitope thereof, and Hepatitis B Virus core antigen or an epitope thereof.

* * * * *